US010407692B2

(12) United States Patent
Stein et al.

(10) Patent No.: US 10,407,692 B2
(45) **Date of Patent: *Sep. 10, 2019**

(54) BACTERIAL RESISTANT TRANSGENIC PLANTS HAVING DYSFUNCTIONAL T3SS PROTEINS

(71) Applicant: Futuragene Israel Ltd., Rehovot (IL)

(72) Inventors: Hanan Stein, Nes-Ziona (IL); Dror Avisar, Kochav Yair (IL)

(73) Assignee: Futuragene Israel Ltd., Rehovot (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/607,498

(22) Filed: May 28, 2017

(65) Prior Publication Data

US 2017/0260542 A1 Sep. 14, 2017

Related U.S. Application Data

(63) Continuation of application No. 14/002,751, filed as application No. PCT/IL2012/050069 on Mar. 1, 2012, now Pat. No. 9,856,492.

(60) Provisional application No. 61/448,223, filed on Mar. 2, 2011.

(51) Int. Cl.

| | |
|---|---|
| ***C12N 15/82*** | (2006.01) |
| ***C07K 14/19*** | (2006.01) |
| ***C07K 14/195*** | (2006.01) |

(52) U.S. Cl.

CPC ........ *C12N 15/8281* (2013.01); *C07K 14/195* (2013.01)

(58) Field of Classification Search

None

See application file for complete search history.

(56) References Cited

U.S. PATENT DOCUMENTS

| | | | | |
|---|---|---|---|---|
| 9,856,492 | B2 * | 1/2018 | Stein .................. | C12N 15/8281 |
| 2004/0034888 | A1 | 2/2004 | Liu et al. | |
| 2005/0076406 | A1 | 4/2005 | Gebhardt et al. | |
| 2009/0044296 | A1 | 2/2009 | Beer et al. | |
| 2009/0258825 | A1 | 10/2009 | He et al. | |
| 2010/0099674 | A1 | 4/2010 | Elofsson | |
| 2010/0249234 | A1 | 9/2010 | Yang et al. | |
| 2013/0347141 | A1 | 12/2013 | Stein et al. | |

FOREIGN PATENT DOCUMENTS

| | | |
|---|---|---|
| WO | WO 2012/117406 | 9/2012 |

OTHER PUBLICATIONS

Gijsegem et al (Ralstonia solanacearum produces Hrp-dependent pili that are required for PopA secretion but not for attachment of bacteria to plant cells. Molecular Microbiology (2000) 36(2), 249-260).*

Davis et al (A dominant-negative needle mutant blocks type III secretion of early but not late substrates in Yersinia. Mol Microbiol, 76(1): 236-259, Apr. 2010).*

Block et al (The *Pseudomonas syringae* type III effector HopG1 targets mitochondria, alters plant development and suppresses plant innate immunity. Cellular Microbiology, 1-12, 2009).*

Taira et al (Mutational analysis of the *Pseudomonas syringae* pv. tomato hrpA gene encoding Hrp pilus subunit. Molecular Microbiology 34(4), 736-744, 1999).*

Lee et al (Use of Dominant-negative HrpA Mutants to Dissect Hrp Pilus Assembly and Type III Secretion in *Pseudomonas syringae* pv. Tomato. The Journal of Biological Chemistry vol. 280, No. 22, Issue of Jun. 3, pp. 21409-21417, 2005).*

Spreter et al (A conserved structural motif mediates formation of the periplasmic rings in the Type III Secretion System. Nat Struct Mol Biol. 16(5): 468-476, 2009).*

Gabriel et al (Identification of Open Reading Frames Unique to a Select Agent: Ralstonia solanacearum Race 3 Biovar 2. Molecular Plant-Microbe Interactions. vol. 1, pp. 69-79, 2006).*

Summary of Expert Meeting Initiated by the Examiner dated Aug. 2, 2017 From the Rospatent, Federal Government Institution, Federal Institute of Industrial Property of the Federal Service for Intellectual Property, Patent and Trademarks of the Russian Federation Re. Application No. 2013143539 and Its Translation Into English. (3 Pages).

Communication Relating to the Results of the Partial International Search dated Jul. 17, 2012 From the International Searching Authority Re. Application No. PCT/IL2012/050069.

International Preliminary Report on Patentability dated Sep. 12, 2013 From the International Bureau of WIPO Re. Application No. PCT/IL2012/050069.

International Search Report and the Written Opinion dated Sep. 24, 2012 From the International Searching Authority Re. Application No. PCT/IL2012/050069.

Notification of Office Action and Search Report dated Feb. 26, 2016 From the State Intellectual Property Office of the People's Republic of China Re. Application No. 201280021463.5 and Its Translation Into English.

(Continued)

*Primary Examiner* — Medina A Ibrahim
*Assistant Examiner* — Wayne Zhong

(57) ABSTRACT

A nucleic acid expression vector comprising a nucleic acid sequence encoding a dominant negative T3SS protein is disclosed. The nucleic acid expression vector further comprising a cis acting regulatory element capable of driving transcription of the nucleic acid sequence in a plant cell. Moreover, the dominant negative T3SS protein mediates assembly of a dysfunctional needle complex.

9 Claims, 14 Drawing Sheets
(9 of 14 Drawing Sheet(s) Filed in Color)

Specification includes a Sequence Listing.

(56) References Cited

OTHER PUBLICATIONS

Notification of Office Action and Search Report dated Nov. 26, 2014 From the State Intellectual Property Office of the People's Republic of China Re. Application No. 201280021463.5.
Notification of Office Action dated Aug. 18, 2015 From the State Intellectual Property Office of the People's Republic of China Re. Application No. 201280021463.5.
Official Action dated Feb. 1, 2016 From the US Patent and Trademark Office Re. U.S. Appl. No. 14/002,751.
Official Action dated Jul. 22, 2016 From the US Patent and Trademark Office Re. U.S. Appl. No. 14/002,751.
Official Action dated Feb. 27, 2017 From the US Patent and Trademark Office Re. U.S. Appl. No. 14/002,751. (28 pages).
Preliminary Report on Patentability dated Oct. 21, 2016 From the State Intellectual Property Service of Ukraine, State Enterprise 'Ukrainian Institute for Industrial Property Re. Application No. a 2013 11593 and Its Translation Into English. (5 Pages).
Preliminary Report on Patentability dated Apr. 28, 2016 From the State Intellectual Property Service of Ukraine, State Enterprise 'Ukrainian Institute for Industrial Property Re. Application No. a 2013 11593 and Its Translation Into English.
Request for Examination dated Feb. 8, 2017 From the Rospatent, Federal Government Institution, Federal Institute of Industrial Property of the Federal Service for Intellectual Property, Patent and Trademarks of the Russian Federation Re. Application No. 2013143539 and Its Translation Into English. (9 Pages).
Request for Examination dated Mar. 11, 2016 From the Rospatent, Federal Government Institution, Federal Institute of Industrial Property of the Federal Service for Intellectual Property, Patent and Trademarks of the Russian Federation Re. Application No. 2013143539 and Its Translation Into English.
Restriction Official Action dated Sep. 21, 2015 From the US Patent and Trademark Office Re. U.S. Appl. No. 14/002,751.
Translation Dated Sep. 9, 2015 of Notification of Office Action dated Aug. 18, 2015 From the State Intellectual Property Office of the People's Republic of China Re. Application No. 201280021463. 5.
Translation Dated Dec. 21, 2014 of Notification of Office Action and Search Report dated Nov. 26, 2014 From the State Intellectual Property Office of the People's Republic of China Re. Application No. 201280021463.5.
Anderson et al. "A Defective Replicase Gene Induces Resistance to Cucumber Mosaic Virus in Transgenic Tobacco Plants", Proc.Natl. Acad.Sci.(PNAS), USA, 89(18): 8759-8763, Sep. 1992.
Davis et al. "A dominant-Negative Needle Mutant Blocks Type III Secretion of Early But Not Late Substrates in Yersinia", Molecular Microbiology, 76(1): 236-259, Apr. 2010.
Gijsegem et al. "Ralstonia Solanacearum Produces Hrp-Dependent Pili That are Required for PopA Secretion But Not for Attachment of Bacteria to Plant Cells", Molecular Microbiology, 36(2): 249-260, Apr. 1, 2000.
Guo et al. "Protein Tolerance to Random Amino Acid Change", Proc.Natl.Acad.Sci (PNAS), USA, 101(25): 9205-9210, Jun. 22, 2004.
Hill et al. "Functional Analysis of Conserved Histidines in ADP-Glucose Pyrophosphorylase From *Escherichia coli*", Biochemical and Biophysical Research Communications, 244(2): 573-577, Mar. 17, 1998.
Lee et al. "Use of Dominant-Negative HrpA Mutants to Dissect Hrp Pilus Assembly and Type III Secretion in *Pseudomonas syringae* Pv.Tomato", The Journal of Biological Chemistry, 280(22): 21409-21417, Jun. 3, 2005. Abstract, p. 21409.
Meyer et al. "PopF1 and PopF2, Two Proteins Secreted by the Type III Protein Secretion System of Ralstonia Solanacearum, Are Translocators Belonging to the HrpF/NopX Family", Journal of Bacteriology, 188(13): 4903-4917, Jul. 2006.
Morello et al. "*Pseudomonas syringae* HrpP Is a Type III Secretion Substrate Specificity Switch Domain Protein That Is Translocated into Plant Cells But Functions Atypically for a Substrate-Switching Protein",Journal of Bacteriology, 191(9): 3120-3131, May 2009.
Mukaihara et al. "Genetic Screening of Hrp Type III-Related Pathogenicity Genes Controlled by the HrpB Transcriptional Activator in Ralstonia Solanacearum", Molecular Microbiology, 54(4): 863-875, Nov. 2004.
Mukaihara et al. "Ralstonia Solanacearum Hpx1 Gene for Hypothetical Protein, Complete CDs, Strain:RS1000", GenBank [Online], XP008134953, GenBank Accession No. AB177893, Nov. 18, 2004.
"Genetic Screening of Hrp Type III-Related Pathogenicity Genes Controlled by the HrpB Transcriptional Activator in Ralstonia Solanacearum", Molecular Microbiology, 54(4): 863-875, 2004. p. 866-869.
Oh et al. "*Pseudomonas syringae* Lytic Transglycosylases Coregulated with the Type III Secretion System Contribute to the Translocation of Effector Proteins into Plant Cells", Journal of Bacteriology, 189(22): 8277-8289, Published Online Sep. 7, 2007.
Poueymiro et al. "Secreted Proteins From Ralstonia Solanacearum: A Hundred Tricks to Kill a Plant", Current Opinion in Microbiology, 12: 44-52, 2009.
Roine et al. "Purified HrpA of *Pseudomonas syringae* Pv. Tomato DC3000 Reassembles Into Pili", FEBS Letters, 417: 168-172, 1997.
Taira et al. "Mutational Analysis of the *Pseudomonas syringae* Pv. Tomato HrpA Gene Encoding Hrp Pilus Subunit", Molecular Microbiology, XP002903858, 34(4): 736-744, Jan. 1, 1999. p. 739, Table 1.
Takabatake et al. "Extracts From Ralstonia Solanacearum Induce Effective Resistance to the Pathogen in Both Arabidopsis and Solanaceous Plants", Journal of General Plant Pathology, XP019855481, 77(1): 33-42, Nov. 11, 2010. Abstract, p. 35, Right Col., 2nd, 3rd Para, p. 36, Figs.1-2.
Van Gijsegem et al. "The HRP Gene Locus of Psudonomas Solanacearum, Which Controls the Production of A Type III Secretion System, Encodes Eight Proteins Related to Components of the Bacterial Flagellar Biogenesis Complex", Molecular Microbiology, 15(6): 1095-1114, 1995.
Veitia "Exploring the Molecular Etiology of Dominant-Negative Mutations", The Plant Cell, 19(12): 3843-3851, Dec. 14, 2007.
Weber et al. "Domain Structure of HrpE, the Hrp Pilus Subunit of Xanthomonas Campestris Pv. Vesicatoria", Journal of Bacteriology, XP055032199, 187(17): 6175-6186, Sep. 1, 2005.
Wei et al. "The Gene Coding for the Hrp Pilus Structural Protein Is Required for Type III Secretion of Hrp and Avr Proteins in *Pseudomonas syringae* Pv. Tomato", Proc. Natl. Acad. Sci. USA, PNAS, 97(5): 2247-2252, Feb. 29, 2000.
Xiang et al. "Cloning of Promoter Wun 1 and Mel 3' Untranslated Region and Construction of Hrp Gene Plant Expression Vector", Journal of Gansu Agricultural University, 39(2): 124-130, Apr. 30, 2004. Abstract, p. 124.
Examination Report Under Sections 12 & 13 of the Patents Act, 1970 and the Patents Rules, 2003 dated Jul. 5, 2018 From the Government of India, Intellectual Property India, Patents, Designs, Trade Marks, Geographical Indications Re. Application No. 1623/MUMNP/2013. (6 Pages).

* cited by examiner

FIG. 3A SEQ ID NO: 2

>T3SS Blocking element 1
MESFRRFSLLSFIALLAYFAFLASAEHHVHQFVITPMAG
VPKFNTTNTTSTTSTFQSFANGVDDAASRTGFQAQYQAITA
QGQQDMLDAAKMQNALNRTQMLAKLMEAGPKAAKDLIS*

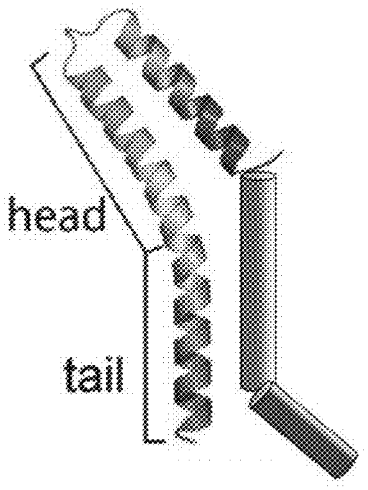

FIG. 3B

FIG. 3C SEQ ID NO: 4

>T3SS Blocking element 2
MGLQQGLVTWFVGVLFLSTLLLSNADVHHYEFFVRPNGV
DDAASRTGFQAQYQAITAQGQQDMLDAAKMQNALNRTQMLA
KLMEAGPKAAKDLIS*

FIG. 3E

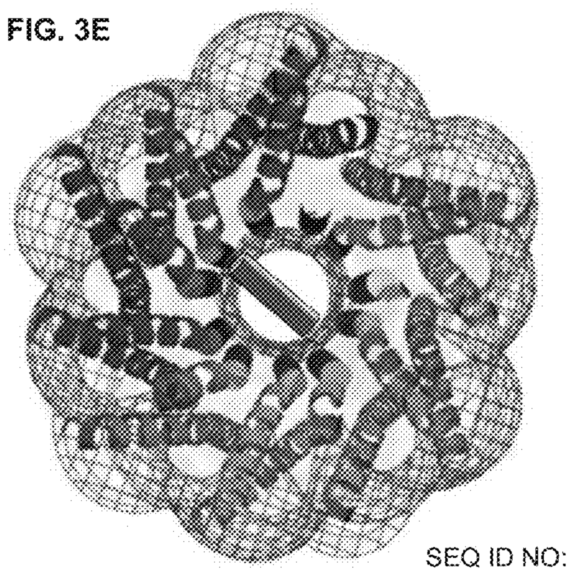

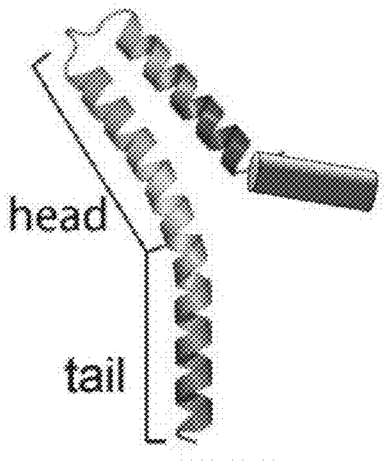

FIG. 3D

SEQ ID NO: 16

>sp|Q56YT0|LAC3_ARATH Laccase
MESFRRFSLLSFIALLAYFAFLASA EHHVHQ

SEQ ID NO: 17

>tr|Q6TDS6|Q6TDS6_GOSAR Secretory laccase Gossypium arboreum
MGLQQGLVTWFVGVLFLSTLLLSNA DVHHYE

FIG. 4A SEQ ID NO: 6

>T3SS Blocking element 3
MESFRRFSLLSFIALLAYFAFLASAMAGVPKPNTTNTTSTTS
TFQSVTVGNDDWTLSSLSETFDSFANGVDDAASRTGFQA
QYQAITAQGQQDMLDAAKMQNALNRTQMLAKLMEAGPKAAKD
LIS*

FIG. 5A SEQ ID NO: 8

>T3SS Blocking element 4
MGLQQGLVTWFVGVLFLSTLLLSNAMAGVPKPNTTNTT
STTSTFQSFANGVDDAASRTGFQAQYQAITAQGQQDML
DAAKMQNALNRTQMLAKLMEAGPKAAKDLISGGQMLA
KLMEAGPKAAKDLIS*

FIG. 6A SEQ ID NO: 10

>T3SS Blocking element 5
MESFRRFSLLSFIALLAYFAFLASAMAGVPKPNTTNTTSTTS
TFQSFANGVDDAASRTPFQAQYQAITAQGQQDMLDAAKMQNA
LNRTQMLAKLMEAGPKAAKDLIS*

FIG. 6C SEQ ID NO: 12

>T3SS Blocking element 6
MGLQQGLVTWFVGVLFLSTLLLSNAMAGVPKPNTTNTT
STTSTFQSFANGVDDAASRTGFQAQYQAITAQGQQDML
DAAKMQNALNRTQMLAKLMEAPPKAAKDLIS*

FIG. 7A
Mutated HrpY - Pilus interference
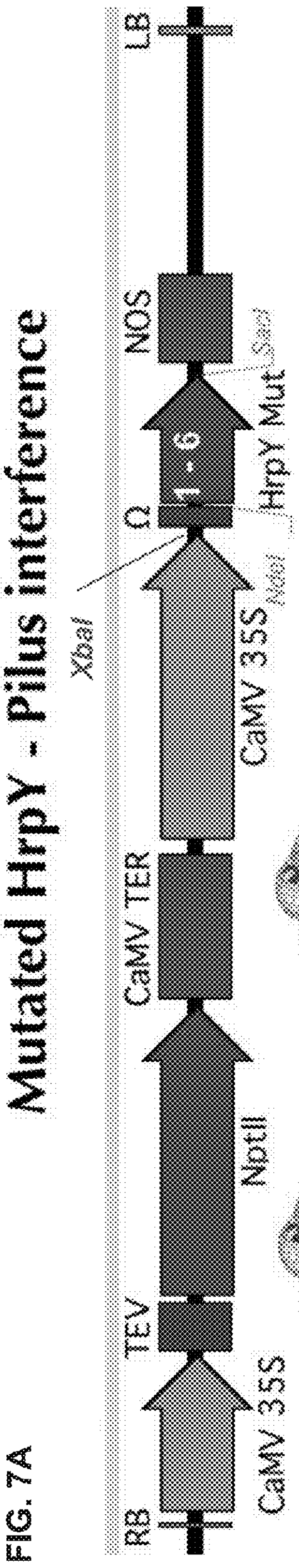
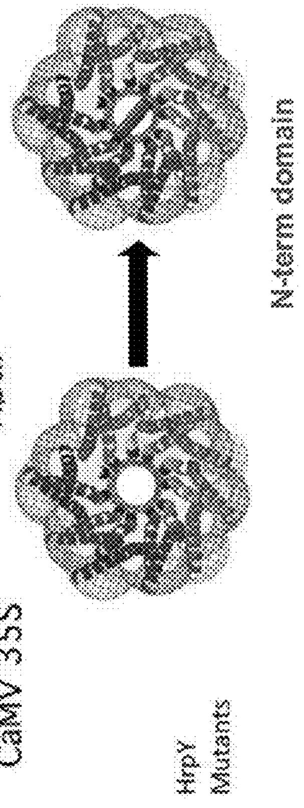
FIG. 7B

FIG. 7C

HrpY Mutants Leader fusion N-domain Original peptide

1 MESFRRFSLLSFIALLAYFAFLASAEHHVHQFVITPMAGVPKPNTTNTTSTTSTFQSFANGVDDAASRTGFQAQYQAITAQGQQDML
DAAKMQNALNRTQMLAKLMEAGPKAAKDLIS
SEQ ID NO: 2

2 MGLQQGLVTWFVGVLFLSTLLLSNADVHHYEFFVRPNGVDDAASRTGFQAQYQAITAQGQQDMLDAAKMQNALNRTQMLAKLM
EAGPKAAKDLIS
SEQ ID NO: 4

3 MESFRRFSLLSFIALLAYFAFLASAMAGVPKPNTTNTTSTTSTFQSVTVGNDDWTLSSLSETFDSFANGVDDAASRTGFQAQYQAITAQGQQDML
DAAKMQNALNRTQMLAKLMEAGPKAAKDLIS
SEQ ID NO: 6

4 MGLQQGLVTWFVGVLFLSTLLLSNAMAGVPKPNTTNTTSTTSTFQSFANGVDDAASRTGFQAQYQAITAQGQQDMLDAAKMQNALNRTQMLAK
LMEAGPKAAKDLISGGQMLAKLMEAGPKAAKDLIS
SEQ ID NO: 8

5 MESFRRFSLLSFIALLAYFAFLASAMAGVPKPNTTNTTSTTSTFQSFANGVDDAASRTPFQAQYQAITAQGQQDMLDAAKMQNALNRTQM
LAKLMEAGPKAAKDLIS
SEQ ID NO: 10

6 MGLQQGLVTWFVGVLFLSTLLLSNAMAGVPKPNTTNTTSTTSTFQSFANGVDDAASRTGFQAQYQAITAQGQQDMLDAAKM
QNALNRTQMLAKLMEAPPKAAKDLIS
SEQ ID NO: 12

SEQ ID NOs: 18 and 19

Genomic PCR sqRT-PCR, Target gene: WiltR HrpYmutant6 Product length: 281bp

Control – minus RT

Genomic PCR

Target gene:
WiltR HrpYmutant1
Product length: 252bp sqRT-PCR, Target gene: WiltR HrpYmutant1 Product length: 252 bp Control – minus RT

BACTERIAL RESISTANT TRANSGENIC PLANTS HAVING DYSFUNCTIONAL T3SS PROTEINS

RELATED APPLICATIONS

This application is a continuation of U.S. patent application Ser. No. 14/002,751, filed on Sep. 3, 2013, which is a National Phase of PCT Patent Application No. PCT/IL2012/050069 having International Filing Date of Mar. 1, 2012, which claims the benefit of priority of U.S. Provisional Patent Application No. 61/448,223 filed on Mar. 2, 2011. The contents of the above applications are all incorporated by reference as if fully set forth herein in their entirety.

SEQUENCE LISTING STATEMENT

The ASCII file, entitled 69894SequenceListing.txt, created on May 21, 2017, comprising 64,507 bytes, submitted concurrently with the filing of this application is incorporated herein by reference.

FIELD AND BACKGROUND OF THE INVENTION

The present invention, in some embodiments thereof, relates to bacterial resistant plants and methods of generating same.

*Ralstonia solanacearum* (Rs), a widely distributed, Gram-negative, soil-borne pathogen belonging to the β-subdivision of Proteobacteria, causes a lethal wilting disease of more than 200 plant species including economically important crops such as tomato, potato and banana. The bacterium enters plant roots through wounds, invades the xylem vessels and spreads rapidly to aerial parts of the plant through the vascular system. Rapidly, populations of more than $10^{10}$ cells per cm of stem are found. The main virulence factor of Rs is exopolysaccharide (EPS), a long (more than 106 Da) sugar polymer that clogs the xylem and causes wilting symptoms and eventually plant death.

Rs displays a remarkable ability for protein secretion of more than 100 proteins. For example, the Type II secretion system (T2SS) secretes factors including the plant cell wall-degrading pectinases, endo-glucanases, and later, the virulence EPS (FIGS. 1A-C). Type III secretion system (T3SS) secretes infection-promoting effector proteins (T3Es) into host cells to optimize the host environment and suppress plant defense responses following invasion (FIGS. 1A-1C).

The Type III secretion system (T3SS) is a sophisticated molecular machinery of Gram-negative bacteria used to 'inject' (translocate) bacterial proteins (effectors) into eukaryotic cells. For this, the T3SS has to assemble into a multi-protein complex, which is comprised of distinct parts; a basal body spanning the two bacterial membranes connected with a cytoplasmic bulb, an attached needle structure resembling a molecular syringe (injectisome/pilus), and a distal needle tip structure that reorganizes into a 'translocon', which is a protein complex that inserts into the host cellular membrane. The pilus is built from only one protein subunit. Multiple subunits oligomerize into the pilus structure. This needle structure allows bacterial proteins to be transported through the inner channel, the conduit, of the needle on their way to the host cell (FIGS. 1A-1C).

Thus, the major extracellular component of the T3SS is the needle that extends from the outer-membrane portion of the apparatus and through which runs a 25-Å channel forming the secretion conduit (the helical parameters of the needle are 5.5 subunits per turn; 4.6-Å axial rise per subunit). The needle is formed by a helical assembly of multiple copies (on the order of 100-150) of a single, small (9 kDa) protein. Though there is little homology between the primary sequence of the pilus building blocks of most of the Gram negative bacteria, it is believed that most share some structural homology. In plant pathogenic bacteria, T3SSs are encoded by hrp (hypersensitive response and pathogenicity) genes, which are so named because they are required for bacteria to cause disease in susceptible plants and to elicit the hypersensitive response in resistant plants. Hrp genes were found in almost all major gram-negative bacterial plant pathogens (e.g. *Pseudomonas syringae, Xanthomonas* spp., *Ralstonia solanacearum*, and *Erwinia* spp.), illustrating a central role of the T3SS in mediating diverse plant-bacteria interactions. Thus, typically, the T3SS extracellular pilus is assembled through the stepwise polymerization of a major component (e.g. HrpY in *R. solanacearum*, HrpA in *P. syringae* and *E. amylovora*, HrpE in *Xanthomonas campestris*, MxiH in *Shigella*, PrgI in *Salmonella* and YscF in *Yersinia*).

As mentioned, although the primary function of type III effectors is to promote plant susceptibility, some effectors are recognized by plant resistance proteins which trigger defense responses, including the hypersensitive response. One method proposed to overcome plant lethal infection by gram-negative bacteria comprises enhancing plant immunity against such pathogens.

U.S. Patent Application Publication No. 20090258825 (He et al.) discloses compositions and methods for enhancing plant defenses against pathogens (e.g. bacterial pathogens). According to their teachings, enhancing plant immunity against the *Pseudomonas syringae* virulence protein HopM1 is effected by increasing the activity of an ATMIN associated plant protection protein, such as ATMIN7.

U.S. Patent Application Publication No. 20090044296 (Beer et al.) discloses methods of increasing plant growth or imparting disease resistance in plants by the use of nucleic acid molecules configured to increase or decrease expression of a nucleic acid molecule that encodes a HrpN-interacting protein (e.g. HIPM). Deletion analysis disclosed therein showed that the 198-aa N-terminal region of HrpN (harpin) of *Erwinia amylovora*, the first cell-free elicitor of the hypersensitive response which plays a critical role in the virulence of this pathogen, is required for interaction with HIPM.

Moreover, bacterial wilt is difficult to control because of the soil borne nature of its causal organism. In plants infected by Rs, disease development depends on the action of the Type II and Type III protein secretion systems and mutations in one of these systems leads to non-pathogenic bacteria [Poueymiro et al., Curr. Opin. Microbiol. (2009) 12:44-52].

Roine et al. [Roine et al., FEBS Letters (1997) 417(2): 168-172] showed that once purified, HrpA, the structural protein of *Pseudomonas syringae* pv. tomato DC3000 pili, alone is sufficient for formation of filament structures undergoing self-assembly.

Taira et al. [Taira et al., Mol Microbiol. (1999) 34(4):737-44] generated insertion mutations in the hrpA gene (e.g. pentapeptide insertions) and created mutated bacteria expressing same. According to their teachings, the carboxy-terminus region of hrpA is crucial for pilus assembly and for bacterial interaction with the affected plant. Moreover, Wei et al. [Wei et al., PNAS (2000) 97(5):2247-2252] identified three single amino acid mutations at the HrpA carboxyl terminus which affect the secretion or regulatory function of the HrpA protein. These results demonstrated an essential role of the Hrp pilus structural gene in protein secretion and coordinate regulation of the type III secretion system in *Pseudomonas syringae*. Furthermore, Lee et al. [Lee et al., J. Bio. Chem. (2005) 280: 21409-17] disclosed that several pentapeptide-induced nonfunctional HrpA proteins, when expressed in bacteria, exert a strong dominant-negative effect on the function of the wild-type HrpA protein blocking the ability of *Pseudomonas syringae* to elicit host responses and cause a disease in-vivo. The dominant-negative HrpA mutants were also able to interfere with the self-assembly of wild-type HrpA into pilus in vitro.

Weber at al. [Weber and Koebnik, J. Bacteriology (2005) 187(17): 6175-6186] described hydrophobicity plot analyses of several Hrp pilin proteins, such as HrpE and HrpA from *Xanthomonas campestris* pv. *vesicatoria* and HrpY from *R. solanacearum*, and revealed a common domain organization. These findings suggest that plant-pathogenic bacteria, challenged with the task of overcoming the barrier of a plant cell wall, independently evolved structurally similar proteins. Weber et al. further disclose that pentapeptide insertion mutants in the C-terminal region of HrpE inhibit Hrp pilus assembly in *X. campestris* pv. *Vesicatoria*. Morphology studies revealed insertion mutants with shortened Hrp pili. This dominant-negative effect suggests that the mutant variant may interfere with the assembly of the Hrp pilus. U.S. Patent Application Publication No. 20100249234 (Yang et al.) discloses methods of reducing virulence in a bacterium, such as a HrpX/HrpY-type system or a T3SS-type system. The method comprises contacting the bacterium with an effective amount of a phenylpropanoid-type inhibitory compound.

U.S. Patent Application Publication No. 20100099674 (Elofsson et al.) discloses methods for decreasing bacterial virulence in a plant by inhibition of the Type III secretion system using an N-substituted 7-quinolylmethyl amine, in particular one that is further substituted in 5- and 8-position on the quinoline ring.

Additional background art includes U.S. Patent Application Publication No. 20050076406.

SUMMARY OF THE INVENTION

According to an aspect of some embodiments of the present invention there is provided a nucleic acid expression vector comprising a nucleic acid sequence encoding a dominant negative T3SS protein and a cis acting regulatory element capable of driving transcription of the nucleic acid sequence in a plant cell, the dominant negative T3SS protein mediates assembly of a dysfunctional needle complex.

According to an aspect of some embodiments of the present invention there is provided an isolated polynucleotide comprising a nucleic acid sequence encoding SEQ ID NO: 2, 4, 6, 8, 10 or 12.

According to an aspect of some embodiments of the present invention there is provided a nucleic acid expression vector comprising an isolated polynucleotide comprising a nucleic acid sequence encoding SEQ ID NO: 2, 4, 6, 8, 10 or 12.

According to an aspect of some embodiments of the present invention there is provided a host cell comprising the nucleic acid expression vector.

According to an aspect of some embodiments of the present invention there is provided a genetically modified plant comprising the nucleic acid expression vector.

According to an aspect of some embodiments of the present invention there is provided a genetically modified plant expressing an exogenous polynucleotide encoding a dominant negative T3SS protein as set forth in SEQ ID NO: 2, 4, 6, 8, 10 or 12.

According to an aspect of some embodiments of the present invention there is provided a method of generating a plant comprising enhanced resistance to a bacterial pathogen compared to a non modified plant, the method comprising introducing into a plant or plant cell the nucleic acid expression vector, thereby generating the plant comprising enhanced resistance to the bacterial pathogen compared to the non modified plant.

A method of evaluating resistance of a plant to a bacterial pathogen, the method comprising: (a) expressing within the plant an exogenous nucleic acid sequence encoding a dominant negative T3SS protein and a cis acting regulatory element capable of driving transcription of the nucleic acid sequence in a plant cell; (b) subjecting the plant to a bacterial pathogen; and (c) comparing the disease in the plant to a wild-type plant grown and infected with the bacterial pathogen under the same conditions, thereby evaluating resistance of the plant to the bacterial pathogen.

According to some embodiments of the invention, the nucleic acid sequence comprises SEQ ID NO: 1, 3, 5, 7, 9 or 11.

According to some embodiments of the invention, the pentapeptide sequence is as set forth in SEQ ID NOs: 20-65.

According to some embodiments of the invention, the nucleic acid sequence encodes for the polypeptide set forth in SEQ ID NO: 2, 4, 6, 8, 10 or 12.

According to some embodiments of the invention, the nucleic acid expression vector further comprises an additional nucleic acid sequence encoding an endoplasmic reticulum signal peptide upstream of the nucleic acid sequence.

According to some embodiments of the invention, the cis acting regulatory element comprises a promoter sequence.

According to some embodiments of the invention, the promoter sequence is a constitutive promoter.

According to some embodiments of the invention, the constitutive promoter is CaMV 35S promoter.

According to some embodiments of the invention, the dominant negative T3SS protein is generated by introduction of a mutation selected from the group consisting of an insertion mutation, a deletion mutation and a substitution mutation.

According to some embodiments of the invention, the insertion mutation comprises an intercalating blocking element.

According to some embodiments of the invention, the T3SS protein is a T3SS structural protein.

According to some embodiments of the invention, the T3SS structural protein is a HRP protein.

According to some embodiments of the invention, the T3SS protein is selected from the group consisting of a *Ralstonia solanacearum* HrpY protein, a *Pseudomonas syringae* HrpA protein, a *Erwinia amylovora* HrpA protein, a *Xanthomonas campestris* HrpE protein, a *Erwinia pyrifoliae* HrpA protein and a *Xanthomonas oryzae* HrpE protein.

According to some embodiments of the invention, the T3SS protein is a *Ralstonia solanacearum* translocon protein.

According to some embodiments of the invention, the *Ralstonia solanacearum* translocon protein is selected from the group consisting of PopF1 and PopF2.

According to some embodiments of the invention, the host cell being a plant cell. According to some embodiments of the invention, the plant comprises enhanced resistance to a bacterial pathogen compared to a non modified plant.

According to some embodiments of the invention, the bacterial pathogen is a gram-negative bacteria.

According to some embodiments of the invention, the gram-negative bacteria is selected from the group consisting of a *Ralstonia solanacearum*, a *Pseudomonas syringae*, a *Erwinia amylovora*, a *Xanthomonas campestris* and a *Xanthomonas oryzae*.

According to some embodiments of the invention, the gram-negative bacteria is a Proteobacteria species.

According to some embodiments of the invention, the Proteobacteria is *Ralstonia solanacearum.*

According to some embodiments of the invention, the plant is selected from the group consisting of a crop plant, a decorative plant, and a tree.

According to some embodiments of the invention, the plant is a Solanaceae plant.

According to some embodiments of the invention, the plant is selected from the group consisting of a tomato plant, a potato plant, an eggplant plant, a banana plant, a sweet pepper plant, an olive plant, an apple plant, a pear plant, a firethorn plant, a flowering crabapple plant, a hawthorn plant, a *cotoneaster* plant, a quince plant, a mountain ash plant, an *arabidopsis* plant, a *geranium*, a ginger plant, a tobacco plant and a *eucalyptus* plant.

According to some embodiments of the invention, the plant is a tomato plant.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1A:
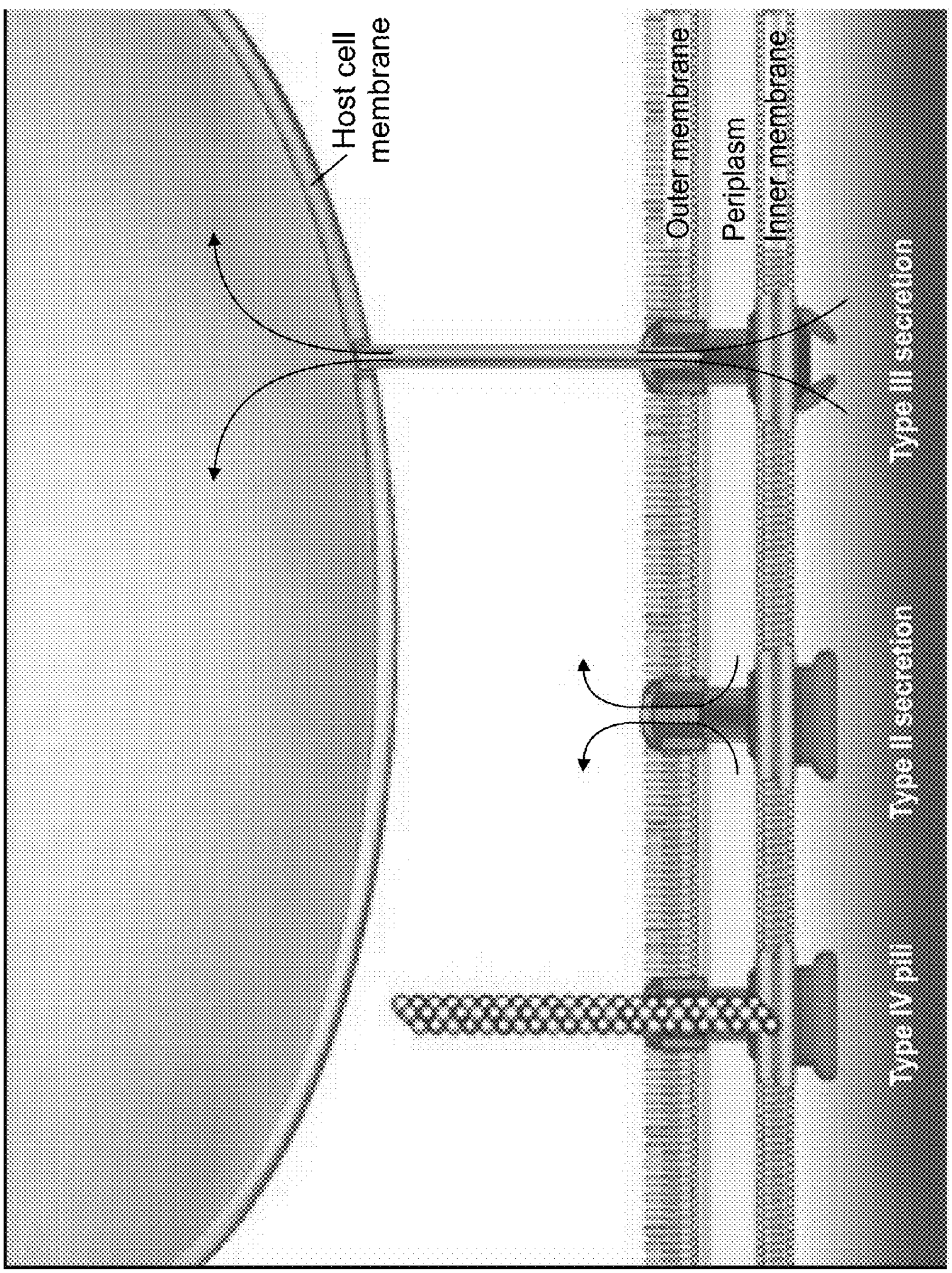

FIG. 1A is a picture illustrating Type II secretion system (T2SS), Type III secretion system (T3SS) and Type IV pili in gram-negative bacteria. The picture was adapted from Donnenberg M. S., Nature (2000) 406: 768-774.

Figure 1B:
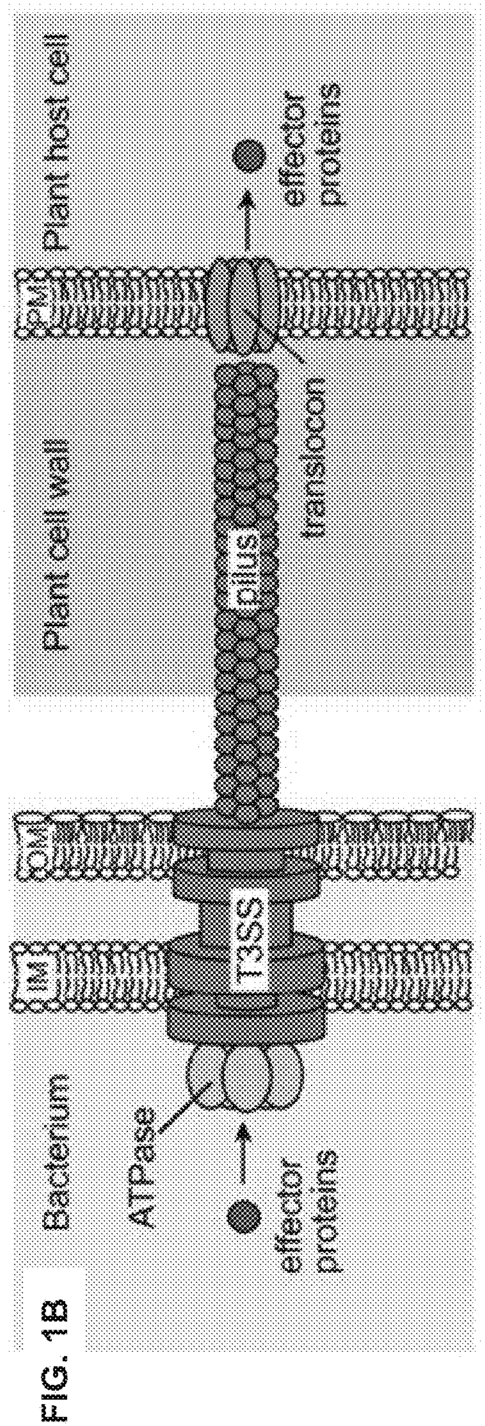
Figure 1C:
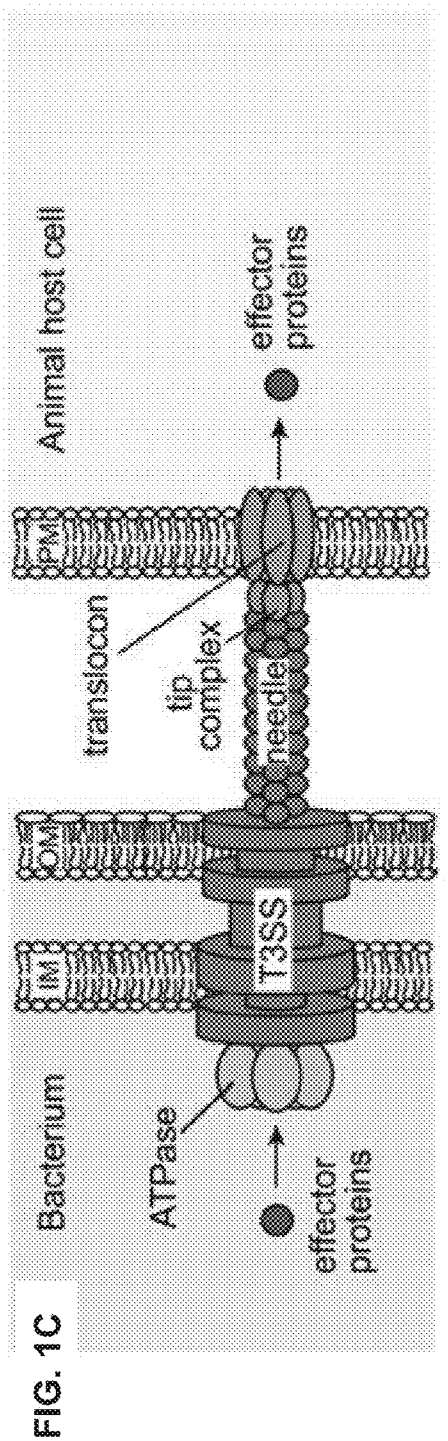

FIGS. 1B-1C are pictures adapted from Buttner and He, Plant Physiology (2009) 150: 1656-64 illustrating the T3SS complex in plant (FIG. 1B) and animal (FIG. 1C) pathogenic bacteria. The secretion apparatus spans both bacterial membranes and is associated with a cytoplasmic ATPase. Plant pathogenic bacteria share a pilus that presumably spans the plant cell wall. Animal pathogenic bacteria has a short needle which is linked via the so-called tip complex (missing in plant pathogens) to the translocon. The translocon forms a channel in the host plasma membrane and allows transport of effector proteins into the host cell cytosol.

Figures 2A, 2B, 2C, 2D, 2E, 2F:
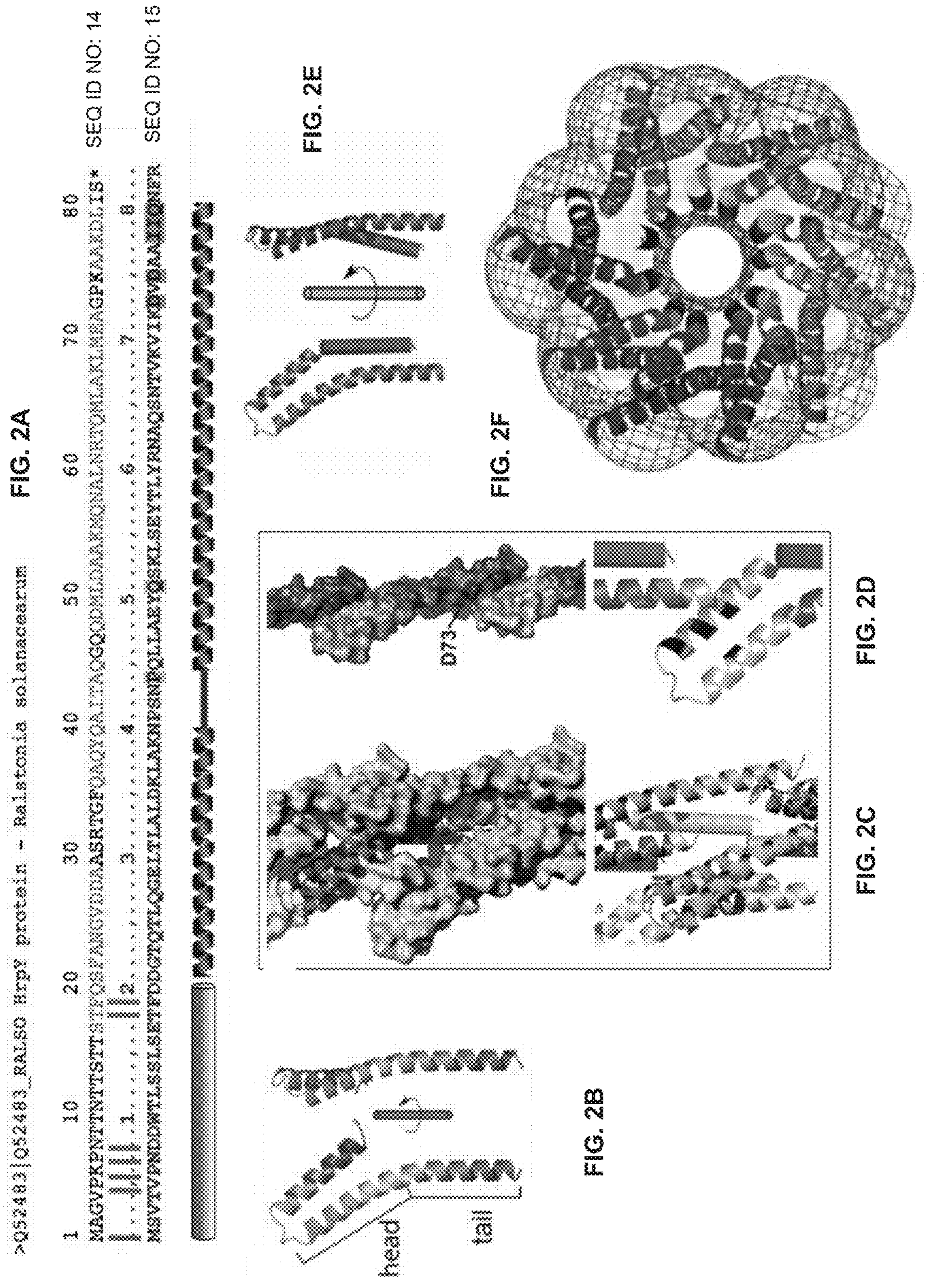

FIGS. 2A-2F are pictures illustrating *Ralstonia solanacearum* (Rs) HrpY protein (SEQ ID NO: 14) aligned with *Shigella* T3SS needle monomer MxiH (SEQ ID NO: 15, FIG. 2A), structural models of *Shigella* MxiH (FIGS. 2B-2E) and overall needle structure (FIG. 2F). Pictures of MxiH and needle structures were adapted from Deane et al., PNAS 2006 103: 12529-33.

FIGS. 3A-3E are pictures illustrating the dominant negative proteins T3SS Intercalating Blocking Elements 1 (FIG. 3A, SEQ ID NO: 2) and 2 (FIG. 3C, SEQ ID NO: 4), the predicted model of the structure of T3SS IBEs 1 and 2 (FIGS. 3B and 3D, respectively), a model of interaction with the needle and needle conduit (FIG. 3E) and plant secretion signals from sp|Q56YT0|LAC3_At Laccase or the tr|Q6TDS6|Q6TDS6_GOSAR Secretory laccase *Gossypium arboreum* (SEQ ID NOs: 16 and 17, respectively). Pictures 3B, 3D and 3E were adapted from Deane et al., PNAS 2006 103: 12529-33.

Figure 4B:
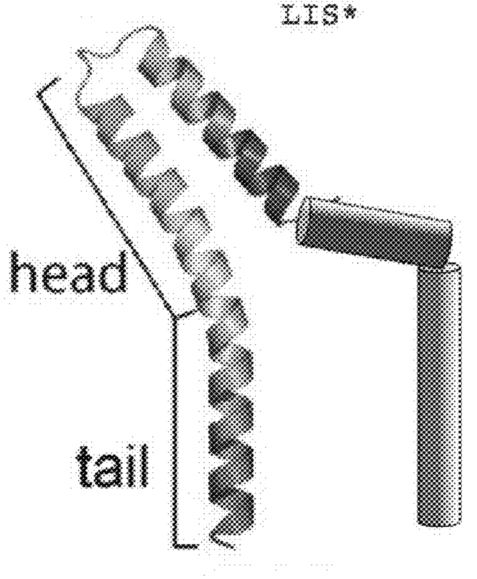
Figure 4C:
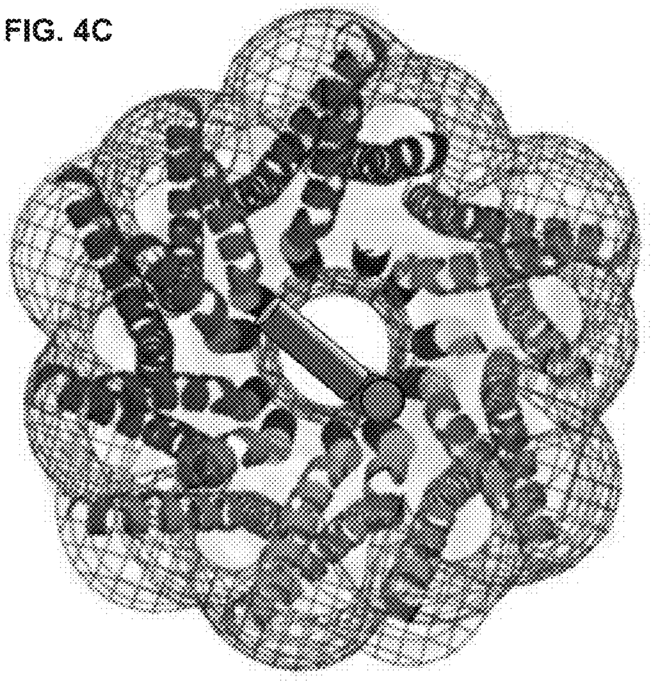

FIGS. 4A-4C are pictures illustrating the dominant negative protein T3SS Intercalating Blocking Element 3 (FIG. 4A, SEQ ID NO: 6), the predicted model of the structure of T3SS IBE 3 (FIG. 4B) and model of interaction with the needle (FIG. 4C). Pictures 4B and 4C were adapted from Deane et al., PNAS 2006 103: 12529-33.

Figure 5B:
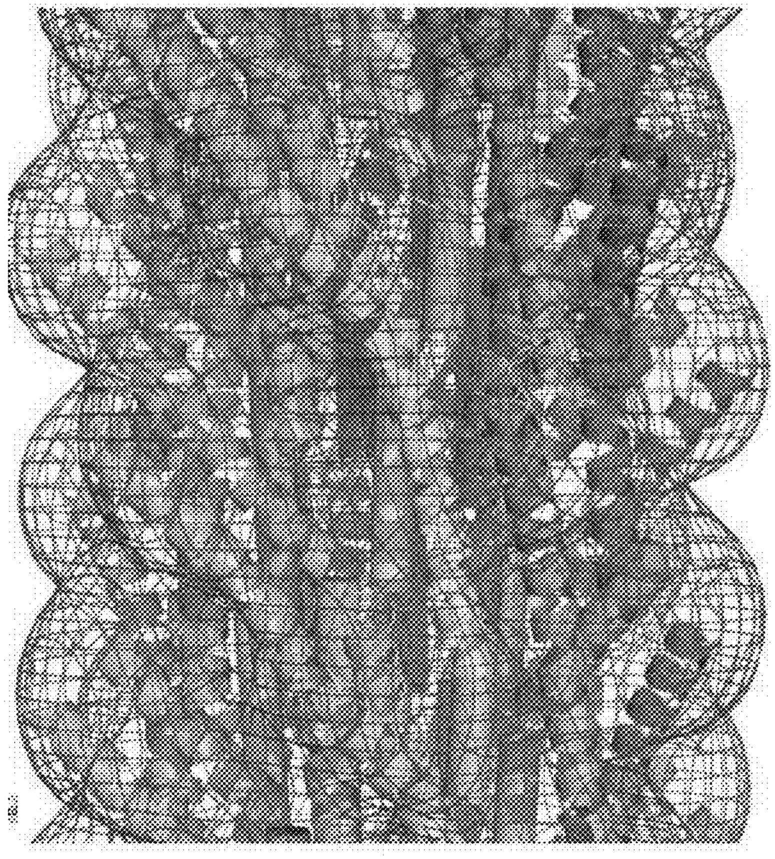
Figure 5C:
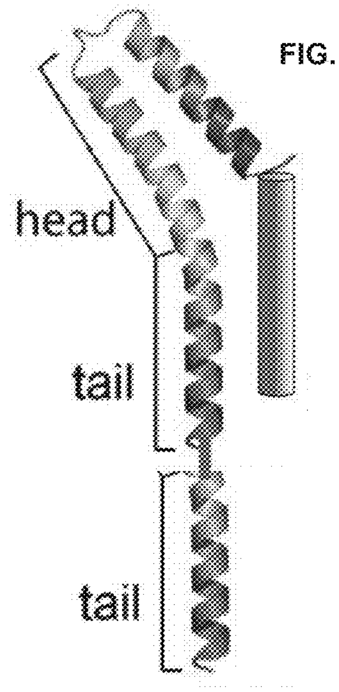

FIGS. 5A-5C are pictures illustrating the dominant negative protein T3SS Intercalating Blocking Element 4 (FIG. 5A, SEQ ID NO: 8), the predicted model of the blocking element (FIG. 5C) and the needle (FIG. 5B). Pictures 5B and 5C were adapted from Deane et al., PNAS 2006 103: 12529-33. Of note, duplicated tail may interact with different monomers disrupting and blocking the needle channel.

Figure 6B:
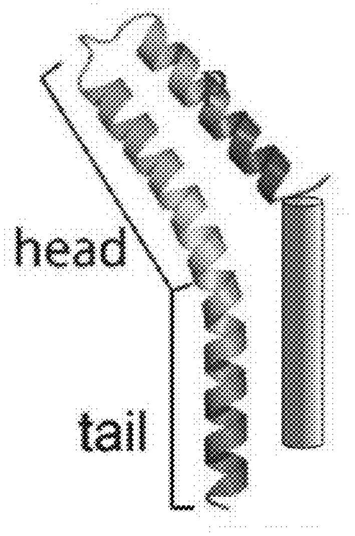
Figure 6D:
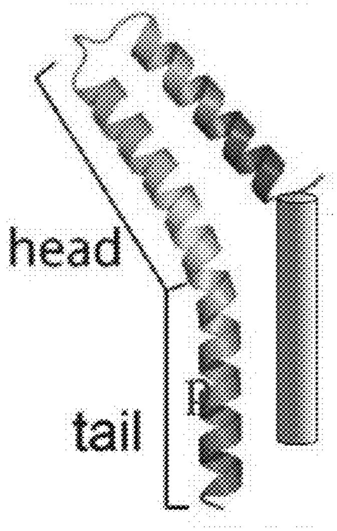

FIGS. 6A-6D are pictures illustrating the dominant negative proteins T3SS Intercalating Blocking Elements 5 (FIG. 6A, SEQ ID NO: 10) and 6 (FIG. 6C, SEQ ID NO: 12) and the predicted model of the structure of the T3SS Intercalating Blocking Elements 5 & 6 (FIGS. 6B and 6D respectively). Of note, HrpY head and tail alpha-helices are disrupted by prolines and such deformations may block the needle channel and disrupt functionality of the needle. Pictures 6B and 6D were adapted from Deane et al., PNAS 2006 103: 12529-33.

FIGS. 7A-7C are pictures illustrating the different *Ralstonia solanacearum* (Rs) HrpY dominant negative proteins. FIG. 7A shows the T-DNA cloning map. Each Intercalating Blocking Element (IBE) was cloned downstream to CaMV 35S promoter and upstream to NOS terminator using XbaI and SacI sites. FIG. 7B shows the model of interaction with the needle; and FIG. 7C shows the different HrpY mutants (SEQ ID NOs: 2, 4, 6, 8, 10 and 12). Picture 7B was adapted from Deane et al., PNAS 2006 103: 12529-33.

Figure 8:
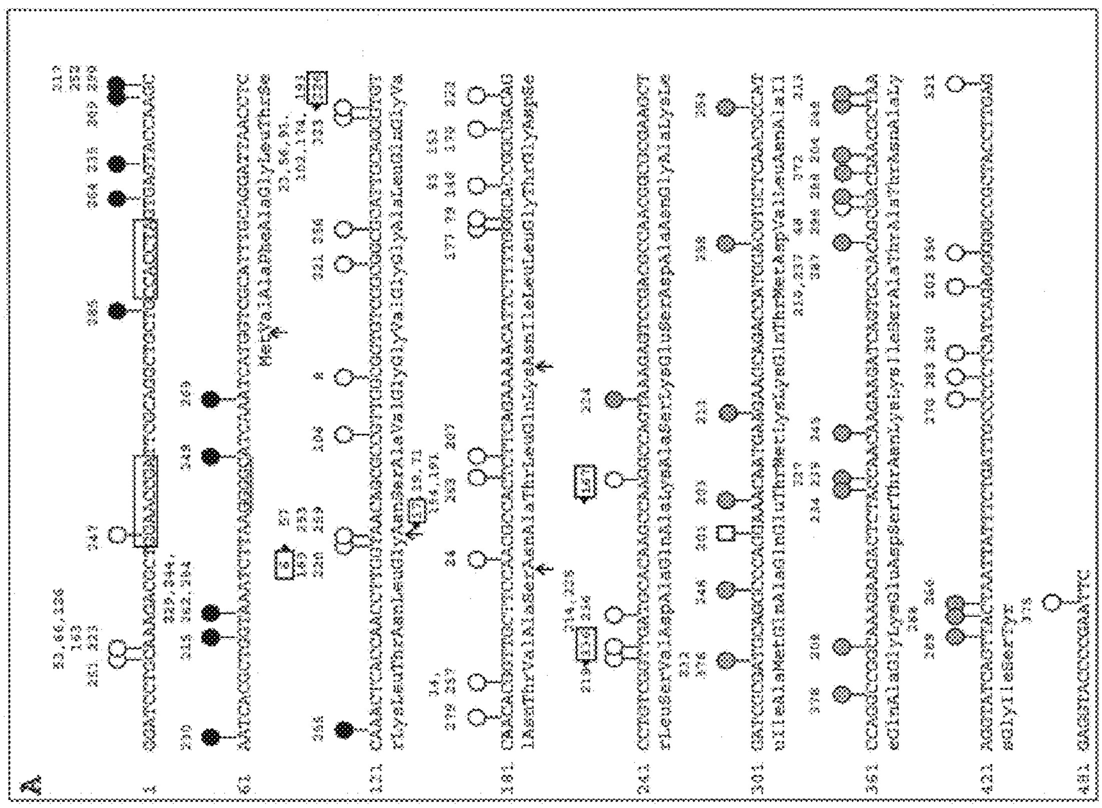

FIG. 8 is a picture adapted from Taira et al., Mol Microbiol. (1999) 34(4):737-44 illustrating insertion mutations and their location in the hrpA gene (SEQ ID NO: 18). In short, location of the insertions in the 496 bp BamHI±EcoRI fragment encoding the HrpA pilus are marked as lollipops with mutant numbers above. Each insertion consists of 10 transposon-derived basepairs and 5 bp upstream of the insertion label duplicated distal to the 10 bp. The amino acid sequence (SEQ ID NO: 19) is written below the nucleotide sequence. The Hrp boxes in the promoter are boxed; the putative ribosome binding site is underlined. Amino-terminal protein processing sites are marked with arrows below the amino acid sequence. The boxed mutation numbers with arrowheads indicate the start and end points of four deletion mutations.

Figure 9:
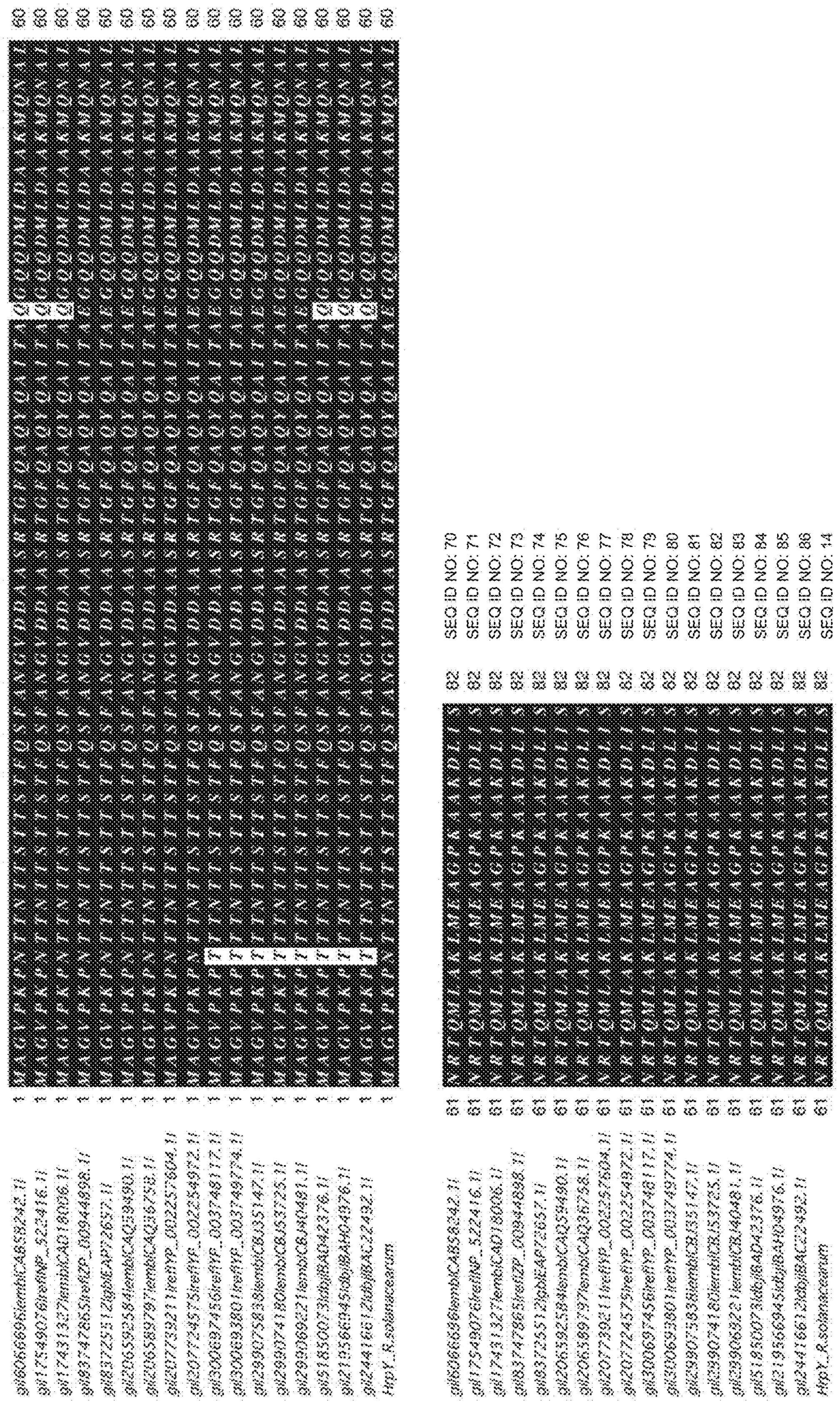

FIG. 9 is an alignment of the *Ralstonia solanacearum* HrpY polypeptide variants (i.e. slight sequence changes between strains, SEQ ID NOs: 14 and 70-86).

Figure 10A:
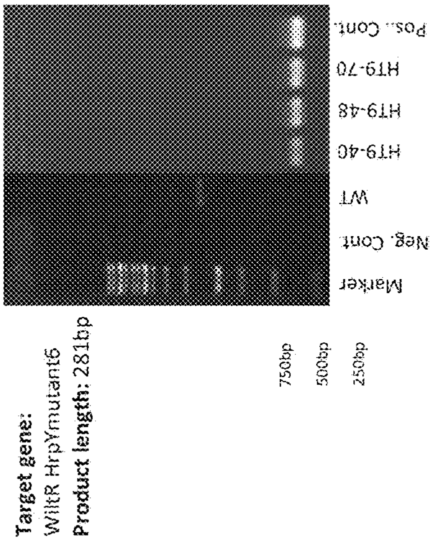
Figure 10B:
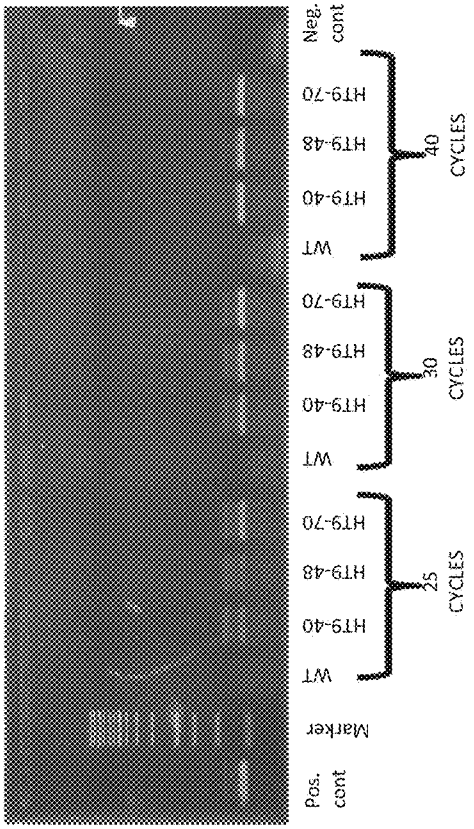
Figure 10C:
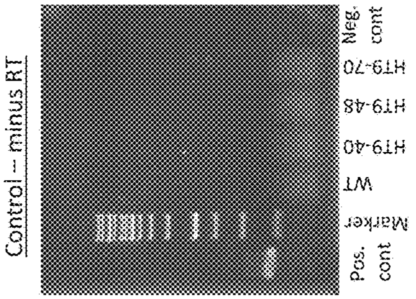

FIGS. 10A-10C are pictures illustrating PCR and sqRT-PCR analysis of tomato plants expressing wilt resistant (WiltR) HrpY mutant 6. Tomato plants were transformed with constructs carrying HrpY mutant 6 and plants were further analyzed by genomic PCR and semi-quantitative RT-PCR. Events expressing these HrpY mutants were detected.

Figure 11A:
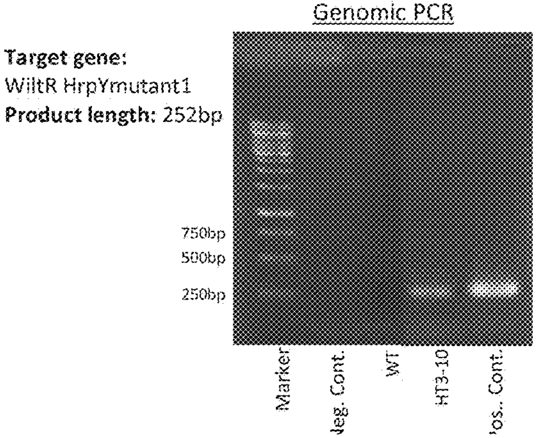
Figure 11B:
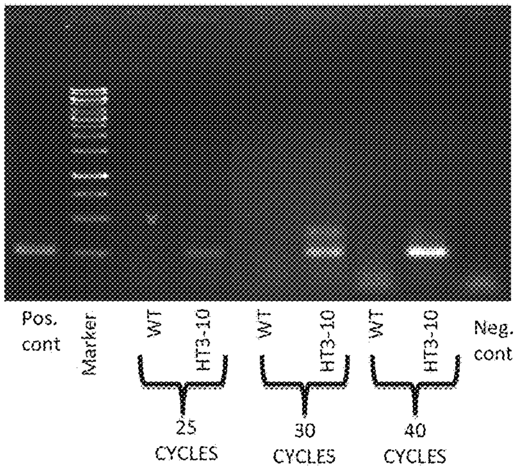
Figure 11C:
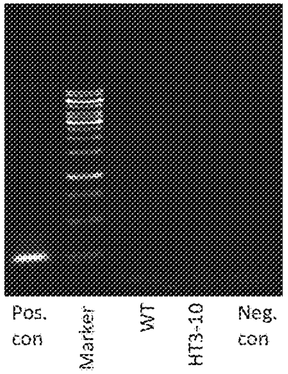

FIGS. 11A-11C are pictures illustrating PCR and sqRT-PCR analysis of tomato plants expressing wilt resistant (WiltR) HrpY mutant 1. Tomato plants were transformed with constructs carrying HrpY mutant 1 and plants were further analyzed by genomic PCR and semi-quantitative RT-PCR. Events expressing these HrpY mutants were detected.

Figure 12A:
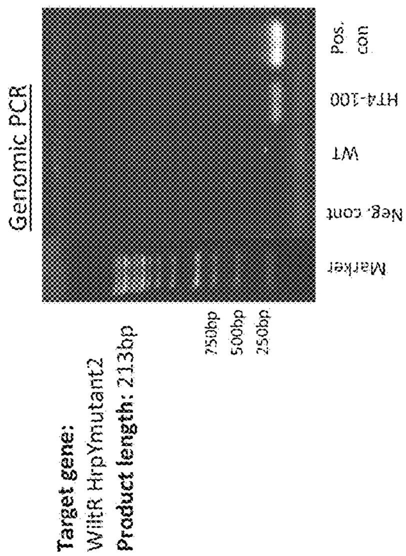
Figure 12B:
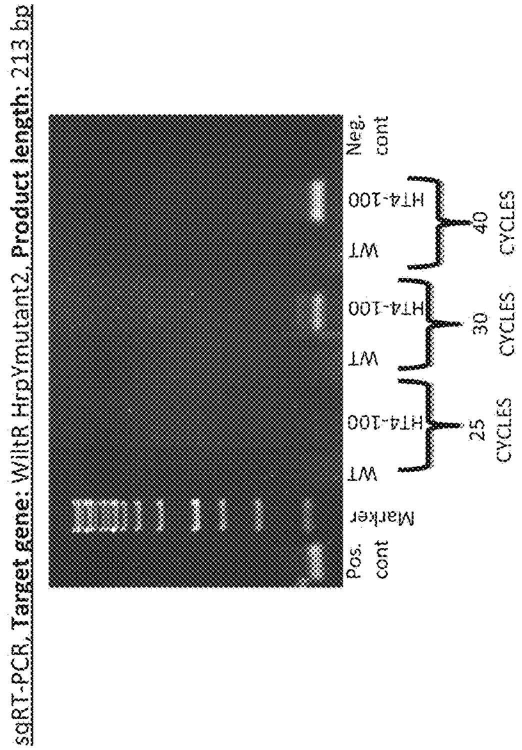
Figure 12C:
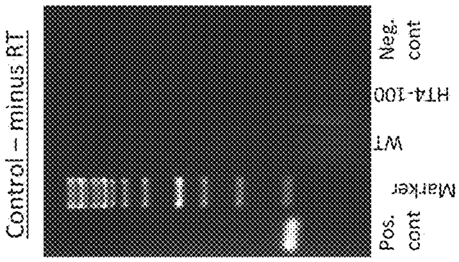

FIGS. 12A-12C are pictures illustrating PCR and sqRT-PCR analysis of tomato plants expressing wilt resistant (WiltR) HrpY mutant 2. Tomato plants were transformed with constructs carrying HrpY mutant 2 and plants were further analyzed by genomic PCR and semi-quantitative RT-PCR. Events expressing these HrpY mutants were detected.

DESCRIPTION OF SPECIFIC EMBODIMENTS OF THE INVENTION

The present invention, in some embodiments thereof, relates to bacterial resistant plants and methods of generating same.

The principles and operation of the present invention may be better understood with reference to the drawings and accompanying descriptions.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

While reducing some embodiments of the present invention to practice, the present inventors have generated dominant negative bacterial type III protein secretion system (T3SS) proteins, which are expressed in plant cells and secreted therefrom. The novel dominant negative T3SS proteins of the present invention intercalate within the T3SS needle structure during its assembly and block the bacterial needle channel, thereby protecting plants from bacterial infection.

The design of the dominant negative T3SS proteins of the present invention is based on preserving and utilizing the native T3SS protein (e.g. HrpY) subunit-subunit interaction sites while incorporating translationally fused channel-blocking peptides or deforming structures of the T3SS protein (e.g. HrpY alpha-helices) which prevent bacterial effectors from being secreted from the bacteria into the plant cells. Plant secretion signals added thereto enable the expression of the dominant negative proteins in the plant cells, secretion from the plant cells and accessibility of the dominant negative T3SS proteins during bacterial pilus assembly in close proximity to the plant cell wall. Thus, for example and as shown in the Examples section which follows, the present inventors have generated intercalating blocking elements of T3SS needle channel (T3SS-IBEs) of gram-negative bacteria. T3SS-IBEs of *Ralstonia solanacearum* (SEQ ID NOs: 2, 4, 6, 8, 10 and 12) were generated using structural modifications of HrpY protein (SEQ ID NO: 14), the building block monomer of the Rs needle. The present inventors have further generated expression vectors comprising these T3SS-IBEs for transformation of plant cells. Moreover, the present inventors have illustrated transformation of tomato plants with *Ralstonia solanacearum* HrpY mutants 1, 2 or 6 and expression of same (see FIGS. 11A-11C, 12A-12C and 10A-10C, respectively). Additionally, the present inventors have contemplated over-expression of modified Rs translocon proteins (PopF1) in transgenic plants. Over-expression of these proteins leads to an arrest in T3SS assembly due to interactions with a premature needle and, thus, deactivation thereof. Thus, modified PopF1 proteins are incorporated into the translocon gate and block it. Taken together, the present teachings may serve as powerful tools in the field of agriculture transgenic technologies for generation of bacterial resistant plants.

Thus, according to one aspect of the present invention there is provided a method of generating a plant comprising enhanced resistance to a bacterial pathogen compared to a non modified plant, the method comprising introducing into a plant or plant cell the nucleic acid expression vector, thereby generating the plant comprising enhanced resistance to the bacterial pathogen compared to the non modified plant.

The term "plant" as used herein encompasses whole plants, ancestors and progeny of the plants and plant parts, including seeds, shoots, stems, roots (including tubers), and plant cells, tissues and organs. The plant may be in any form including suspension cultures, embryos, meristematic regions, callus tissue, leaves, gametophytes, sporophytes, pollen, and microspores. Plants that are particularly useful in the methods of the invention include all plants which belong to the superfamily Viridiplantee, in particular monocotyledonous and dicotyledonous plants including a fodder or forage legume, ornamental plant, food crop, tree, or shrub selected from the list comprising *Acacia* spp., *Acer* spp., *Actinidia* spp., *Aesculus* spp., *Agathis australis, Albizia amara, Alsophila tricolor, Andropogon* spp., *Arachis* spp, *Areca catechu, Astelia fragrans, Astragalus cicer, Baikiaea plurijuga, Betula* spp., *Brassica* spp., *Bruguiera gymnorrhiza, Burkea africana, Butea frondosa, Cadaba farinosa, Calliandra* spp, *Camellia sinensis, Canna indica, Capsicum* spp., *Cassia* spp., *Centroema pubescens, Chacoomeles* spp., *Cinnamomum cassia, Coffea arabica, Colophospermum mopane, Coronillia varia, Cotoneaster serotina, Crataegus* spp., *Cucumis* spp., *Cupressus* spp., *Cyathea dealbata, Cydonia oblonga, Cryptomeria japonica, Cymbopogon* spp., *Cynthea dealbata, Cydonia oblonga, Dalbergia monetaria, Davallia divaricata, Desmodium* spp., *Dicksonia squarosa, Dibeteropogon amplectens, Dioclea* spp, *Dolichos* spp., *Dorycnium* rectum, *Echinochloa pyramidalis, Ehraffia* spp., *Eleusine coracana, Eragrestis* spp., *Erythrina* spp., *Eucalyptus* spp., *Euclea schimperi, Eulalia vi/losa, Pagopyrum* spp., *Feijoa sellowlana, Fragaria* spp., *Flemingia* spp, *Freycinetia banksli, Geranium thunbergii, GinAgo biloba, Glycine javanica, Gliricidia* spp, *Gossypium hirsutum, Grevillea* spp., *Guibourtia coleosperma, Hedysarum* spp., *Hemaffhia altissima, Heteropogon contoffus, Hordeum vulgare, Hyparrhenia rufa, Hypericum erectum, Hypeffhelia dissolute, Indigo incamata, Iris* spp., *Leptarrhena pyrolifo-* lia, *Lespediza* spp., *Lettuca* spp., *Leucaena leucocephala, Loudetia simplex, Lotonus bainesli, Lotus* spp., *Macrotyloma axillare, Malus* spp., *Manihot esculenta, Medicago saliva, Metasequoia glyptostroboides, Musa sapientum, Nicotianum* spp., *Onobrychis* spp., *Ornithopus* spp., *Oryza* spp., *Peltophorum africanum, Pennisetum* spp., *Persea gratissima, Petunia* spp., *Phaseolus* spp., *Phoenix canariensis, Phormium cookianum, Photinia* spp., *Picea glauca, Pinus* spp., *Pisum sativam, Podocarpus totara, Pogonarthria fleckii, Pogonaffhria squarrosa, Populus* spp., *Prosopis cineraria, Pseudotsuga menziesii, Pterolobium stellatum, Pyrus communis, Quercus* spp., *Rhaphiolepsis umbellata, Rhopalostylis sapida, Rhus natalensis, Ribes grossularia, Ribes* spp., *Robinia pseudoacacia, Rosa* spp., *Rubus* spp., *Salix* spp., *Schyzachyrium sanguineum, Sciadopitys vefficillata, Sequoia sempervirens, Sequoiadendron giganteum, Sorghum bicolor, Spinacia* spp., *Sporobolus fimbriatus, Stiburus alopecuroides, Stylosanthos humilis, Tadehagi* spp, *Taxodium distichum, Themeda triandra, Trifolium* spp., *Triticum* spp., *Tsuga heterophylla, Vaccinium* spp., *Vicia* spp., *Vitis vinifera, Watsonia pyramidata, Zantedeschia aethiopica, Zea mays,* amaranth, artichoke, asparagus, broccoli, Brussels sprouts, cabbage, canola, carrot, cauliflower, celery, collard greens, flax, kale, lentil, oilseed rape, okra, onion, potato, rice, soybean, straw, sugar beet, sugar cane, sunflower, tomato, squash tea, trees. Alternatively algae and other non-Viridiplantae can be used for the methods of the present invention.

According to a specific embodiment the plant is a Solanaceae plant.

According to a specific embodiment the plant is a *Solanum* plant.

According to another specific embodiment, the *Solanum* plant is a tomato (*Lycopersicum esculentum*).

According to another specific embodiment the plant comprises a potato (*Solanum tuberosum*); a tomato (*Lycopersicum esculentum*); an aubergine (egg plant) (*Solanum melongena*); a banana, (*Musa* spp); a *geranium* (common name) (*Pelargonium*); a ginger (*Zingiber officinale*); a tobacco (*Nicotiana tabacum*); a sweet pepper (*Capsicum* spp); an olive (*Olea europea*) an *arabidopsis* plant, a *eucalyptus*, an apple, a flowering crabapple, a pear, a firethorn, a hawthorn, a *cotoneaster*, a quince or a mountain ash plant.

As used herein the term “bacterial pathogen” refers to any type of virulent bacterial species or strains which infects plants and include, without being limited to, *Pseudomonas* spp., *Erwinia*-related strains, *Ralstonia solanacearum* and *Xanthomonas campestris*. The bacterium may be a *Pseudomonas* spp including *P. aureofaciens, P. chlororaphis, P. fluorescens, P. marginalis, Pseudomonas syringae, P. tolaasii, P. agarici* and *P. viridiflava*. The bacterium may be an *Erwinia*-related strain including *Dickeya dadantii* (*Erwinia chrysanthemi*), *Erwinia carotovora, Erwinia atroseptica* and *Erwinia amylovora*. The bacterium may be a *Xanthomonas campestris*-related strain including *Xanthomonas campestris* pv. *campestris* (Xcc) and *Xanthomonas oryzae*.

According to an embodiment of the present invention, the bacteria is a gram-negative bacteria.

According to a specific embodiment, the gram-negative bacteria is a Proteobacteria species.

According to another specific embodiment, the Proteobacteria is *Ralstonia solanacearum.*

According to another specific embodiment, the gram-negative bacteria is selected from the group consisting of *Ralstonia solanacearum, Pseudomonas syringae, Erwinia amylovora, Erwinia Psidii, Erwinia pyrifoliae, Xanthomonas campestris* and *Xanthomonas oryzae.*

As used herein the phrase “enhanced resistance” refers to reducing the virulence of the bacteria and hence reducing susceptibility of the host plant as compared to a non modified plant infected with the same bacterial pathogen. Reducing bacterial virulence according to the present teachings is effected by expression of dominant negative proteins associated with bacterial virulence (e.g. needle complex, as described in further detail hereinbelow) and may affect any step of the bacterial life cycle when it is associated with a host, including without limitation, the adherence, invasion, replication, evasion of host defenses and transmittal to a new host.

Enhanced resistance to bacterial pathogens may be manifested in the form of reduced symptoms in a host, and thus may be detected by monitoring the host for a reduced reaction to the bacteria associated therewith. Enhanced resistance may be at least about a 1% reduction, at least about a 5% reduction, at least about a 10% reduction, at least about a 20% reduction, at least about a 30% reduction, at least about a 40% reduction, at least about a 50% reduction, at least about a 60% reduction, at least about a 70% reduction, at least about a 80% reduction, at least about a 90% reduction, or at least about a 100% reduction of symptoms associated with a bacterial pathogen, as measured by any assay known to those of skill in the art, when measured against a suitable control (e.g. a non modified plant grown under the same conditions).

The methods of the present invention are effected by introducing into the plant a nucleic acid expression vector comprising a nucleic acid sequence encoding a dominant negative T3SS protein and a cis acting regulatory element capable of driving transcription of the nucleic acid sequence in a plant cell, the dominant negative T3SS protein mediates assembly of a dysfunctional needle complex.

The term “T3SS” as used herein refers to the type III secretion system (also named TTSS) of bacteria (e.g. gram negative bacteria) which typically functions as a needle-like structure to secrete proteins directly from the bacterial cell. The T3SS needle complex generally starts at the cytoplasm of the bacterium, crosses the two membranes and protrudes out of the cell (see e.g. FIG. 1A). The part anchored in the membrane is the base (or basal body) of the T3SS. The extracellular part is the needle (also named pilus). The final structure serving as the gate to the host cell cytoplasm is the translocon (see FIGS. 1B-1C). A so-called inner rod connects the needle to the base.

As used herein the term “T3SS protein” refers to a protein which makes up the T3SS secretion complex. These include the structural proteins, i.e. those which build the bases, the inner rod, the needle, the tip or the translocon. The needle itself is typically made out of many units of a single T3SS protein. Thus, the majority of the different T3SS proteins are those that build the base and those that are secreted into the host.

According to an embodiment of the present invention, the T3SS protein is a protein which makes up the T3SS needle structure such as HRP (hypersensitive response and pathogenicity) protein. Exemplary HRP proteins includes, without being limited to, *Ralstonia solanacearum* HrpY protein, *Pseudomonas syringae* HrpA protein, *Erwinia amylovora* HrpA protein, *Erwinia pyrifoliae* HrpA protein and *Xanthomonas campestris* HrpE protein (for exemplary proteins, see Table 1, below, incorporated herein from Buttner and He, Plant Physiology (2009) 150:1656-1664].

TABLE 1

| Exemplary T3SS proteins | | |
|---|---|---|
| Protein | Predicted protein function | Bacterial species |
| HrpA | Pilus protein | *Erwinia amylovora* |
| HrpK | Translocon protein | |
| HrpA | Pilus protein | *Pseudomonas syringae* pv *tomato* |
| HrpK1 | Translocon protein | |
| HrpY | Pilus protein | *Ralstonia solanacearum* |
| PopF1 | Translocon protein | |
| PopF2 | | |
| HrpExcv | Pilus protein | *Xanthomonas* spp. |
| HrpFxcv | Translocon protein | |
| HrpFxoo | | |
| HrpA | Pilus protein | *Erwinia pyrifoliae* |

Of note:
xcv—*X. campestris* pv *vesicatoria*, xoo—*X. oryzae* pv *oryzae*

According to a specific embodiment, the wild-type *Ralstonia solanacearum* HrpY polypeptide is as set in SEQ ID NO: 14.

According to another embodiment, the *Ralstonia solanacearum* HrpY polypeptide comprises variants as set forth in SEQ ID NO: 70-86.

According to a specific embodiment, the wild-type *Pseudomonas syringae* HrpA polypeptide is as set in SEQ ID NO: 19.

According to a specific embodiment, the wild-type *Erwinia amylovora* HrpA polypeptide is as set in SEQ ID NO: 88.

According to a specific embodiment, the wild-type *Xanthomonas campestris* HrpE polypeptide is as set in SEQ ID NO: 90.

According to a specific embodiment, the wild-type *Xanthomonas oryzae* HrpE polypeptide is as set in SEQ ID NO: 92.

According to another embodiment, the T3SS protein is a translocon protein such as the *Ralstonia solanacearum* translocon proteins PopF1 or PopF2 (SEQ ID NOs: 67 and 69, respectively).

According to a specific embodiment, the wild-type *Erwinia pyrifoliae* HrpA polypeptide is as set in SEQ ID NO: 100.

The phrase "dominant negative T3SS protein" as used herein refers to a T3SS protein which has a structurally altered gene product that interacts with the wild type T3SS protein secreted from the bacteria but mediates the formation of a dysfunctional needle complex (e.g. one which is not able to or comprises a reduced ability as compared to wild-type protein to penetrate a host cell or transport effector proteins into the host cell). The bacterial dysfunctional needle complex may be structurally deformed (e.g. partially or fully blocked or distorted in such a way which renders it less capable of transferring effector proteins to a host cell) or may partially assemble or not assemble at all. Typically the dominant negative T3SS protein of the present invention reduces infectivity and pathogenicity of the bacteria. Methods of measuring infectivity are well known in the art.

Thus, the dominant negative T3SS protein reduces the assembly and/or functionality of the needle complex and consequently the infectivity of the pathogenic bacteria by about 5%, by about 10%, by about 20%, by about 30%, by about 40%, by about 50%, by about 60%, by about 70%, by about 80%, by about 90% or by about 100%, as compared to bacteria having a needle structure composed of wild type T3SS proteins.

Of note, according to a specific embodiment, the dominant negative protein is expressed exogenously to the bacteria by the plant cell.

Typically, the dominant negative T3SS protein is encoded by a gene comprising one or more mutations in the wild type protein coding sequence such as an insertion mutation, a deletion mutation or a substitution mutation. These mutations may comprise a single nucleic acid alteration in the wild type T3SS protein (e.g., inclusion of a beta breaker amino acid such as a proline or a synthetic mimetic thereof) or alternatively may comprise 2, 3, 4, 5, 6, 7, 8, 9, 10, 15, 20, 25 or more nucleic acid alterations. Alternatively, the mutation may comprise insertion of a single peptide (3, 4, 5, 10 amino acids in length) or of several peptides (e.g. pentapeptide insertion) into the T3SS protein.

Exemplary single amino acid mutations which may be implemented in the peptides of the present invention include replacement of glycine at location 23 of hrpA gene with alanine, replacement of alanine at location 54 of hrpA gene with glutamic acid, replacement of lysine at location 93 of hrpA gene with isoleucine, replacement of aspartic acid at location 95 of hrpA gene with serine, replacement of isoleucine at location 101 of hrpA gene with threonine, replacement of isoleucine at location 111 of hrpA gene with proline.

Exemplary pentapeptide insertions which may be inserted into the peptides of the present invention are set forth in SEQ ID NOs: 20-65 (see Table 2, below).

It will be appreciated that the mutations may be effected at any location in the T3SS gene which results in a dominant negative protein. Exemplary locations of nucleic acid insertions and deletions are depicted for HrpA gene, see FIG. 8 and in Table 2 below [incorporated herein from Taira et al., Mol Microbiol. (1999) 34(4):737-44].

As mentioned and according to a specific embodiment, the dominant negative T3SS protein of the present invention is one which maintains protein-protein interaction sites which allows it to bind with high affinity to the cognate wild-type bacterial protein and form a needle structure, however, due to the mutations in the dominant negative proteins, the resultant needle structure is dysfunctional.

Thus, the present invention contemplates any mutation in or to a T3SS gene which renders the needle complex dysfunctional.

According to an embodiment of the present invention, the insertion mutation comprises an intercalating blocking element (IBE). Dominant negative T3SS proteins comprising IBEs typically form subunit-subunit interactions with the cognate proteins while incorporating translationally fused channel-blocking elements (e.g. peptides) or deforming structures of the T3SS protein (e.g. HrpY alpha-helices) which prevent bacterial effectors from being secreted from the bacteria into the plant cells (see Example 1 of the Examples section which follows).

According to an embodiment of this aspect of the present invention, the nucleic acid sequence encodes for a peptide as set forth in SEQ ID NOs: 2, 4, 6, 8, 10 or 12.

According to another embodiment, the dominant-negative T3SS proteins are capable of arresting T3SS assembly due to interactions with a premature needle (e.g. the dominant negative translocon proteins interact with the needle ahead of time, thus, interfering with the T3SS assembly and deactivate it (see Example 3 of the Examples section which follows).

TABLE 2

| Exemplary pentapeptide insertions and locations for insertions and deletions of nucleic acids in the HrpA gene | | |
|---|---|---|
| | Pentapeptide | |
| | | Location of insertion |
| | | 8 |
| | | 9 |
| | | 19 |
| | | 39 |
| | | 49 |
| | | 52 |
| | | 58 |
| | | 59 |
| | | 61 |
| | | 70 |
| | | 72 |
| | | 86 |
| | | 91 |
| SEQ ID NO: 20 | MRPHS | 122 |
| SEQ ID NO: 21 | GAAAI | 138 |
| SEQ ID NO: 22 | CGRIG | 139 |
| SEQ ID NO: 23 | CGRSA | 148 |
| SEQ ID NO: 24 | GAAAV | 153 |
| SEQ ID NO: 25 | CGRIG | 163 |
| SEQ ID NO: 26 | CGRSG | 166 |
| SEQ ID NO: 27 | VRPQQ | 176 |
| SEQ ID NO: 28 | GAAAQ | 177 |
| SEQ ID NO: 29 | NAAAV | 183 |
| SEQ ID NO: 30 | TAAAN | 186 |
| SEQ ID NO: 31 | MRPHS | 197 |
| SEQ ID NO: 32 | TAAAA | 204 |
| SEQ ID NO: 33 | LRPHT | 206 |
| SEQ ID NO: 34 | CGRTF | 226 |
| SEQ ID NO: 35 | VRPHL | 227 |
| SEQ ID NO: 36 | MRPQG | 230 |
| SEQ ID NO: 37 | CGRTG | 235 |
| SEQ ID NO: 38 | CGRSD | 238 |
| SEQ ID NO: 39 | VRPQS | 248 |
| SEQ ID NO: 40 | VAAAS | 249 |
| SEQ ID NO: 41 | DAAAV | 252 |
| SEQ ID NO: 42 | NAAAA | 264 |

TABLE 2-continued

| Exemplary pentapeptide insertions and locations for insertions and deletions of nucleic acids in the HrpA gene | | |
|---|---|---|
| | Pentapeptide | |
| SEQ ID NO: 43 | CGRTS | 271 |
| SEQ ID NO: 44 | MRPHA | 308 |
| SEQ ID NO: 45 | VRPQQ | 314 |
| SEQ ID NO: 46 | CGRTQ | 319 |
| SEQ ID NO: 47 | CGRKE | 322 |
| SEQ ID NO: 48 | NAAAM | 330 |
| SEQ ID NO: 49 | DAAAM | 345 |
| SEQ ID NO: 50 | AAAAN | 357 |
| SEQ ID NO: 51 | VRPHQ | 365 |
| SEQ ID NO: 52 | AAAAG | 369 |
| SEQ ID NO: 53 | MRPHS | 383 |
| SEQ ID NO: 54 | TAAAS | 384 |
| SEQ ID NO: 55 | CGRTN | 388 |
| SEQ ID NO: 56 | AAAAT | 405 |
| SEQ ID NO: 57 | AAAAT | 408 |
| SEQ ID NO: 58 | CGRTA | 409 |
| SEQ ID NO: 59 | AAAAT | 411 |
| SEQ ID NO: 60 | MRPQT | 413 |
| SEQ ID NO: 61 | AAAAN | 417 |
| SEQ ID NO: 62 | CGRNA | 418 |
| SEQ ID NO: 63 | CGRIS | 430 |
| SEQ ID NO: 64 | YAAAS | 432 |
| SEQ ID NO: 65 | CGRSY | 433 |
| | | 451 |
| | | 453 |
| | | 455 |
| | | 461 |
| | | 464 |
| | | 479 |
| | | 493 |
| | | Location of deletion |
| | | 138-177 |
| | | 138-204 |
| | | 137-249 |
| | | 138-264 |

Nucleic acid sequences according to this aspect of the present invention can be a complementary polynucleotide sequence (cDNA), a genomic polynucleotide sequence and/or a composite polynucleotide sequences (e.g., a combination of the above).

As used herein the phrase "complementary polynucleotide sequence" refers to a sequence, which results from reverse transcription of messenger RNA using a reverse transcriptase or any other RNA dependent DNA polymerase. Such a sequence can be subsequently amplified in vivo or in vitro using a DNA dependent DNA polymerase.

As used herein the phrase "genomic polynucleotide sequence" refers to a sequence derived (isolated) from a chromosome and thus it represents a contiguous portion of a chromosome.

As used herein the phrase "composite polynucleotide sequence" refers to a sequence, which is at least partially complementary and at least partially genomic. A composite sequence can include some exonal sequences required to encode the polypeptide of the present invention, as well as some intronic sequences interposing therebetween. The intronic sequences can be of any source, including of other genes, and typically will include conserved splicing signal sequences. Such intronic sequences may further include cis acting expression regulatory elements, as described in further detail below.

According to a specific embodiment the nucleic acid sequence comprises an insertion such as set forth in SEQ ID NO: 1, 3, 5, 7, 9 and 11.

Constructs useful in the methods according to the present invention may be constructed using recombinant DNA technology well known to persons skilled in the art. The gene constructs may be inserted into vectors, which may be commercially available, suitable for transforming into plants and suitable for expression of the gene of interest in the transformed cells. The genetic construct can be an expression vector wherein the heterologous nucleic acid sequence is operably linked to a cis-acting regulatory element allowing expression in the plant cells.

As used herein, the phrase "cis acting regulatory element" refers to a polynucleotide sequence, preferably a promoter, which binds a trans acting regulator and regulates the transcription of a coding sequence located downstream thereto.

As used herein, the phrase "operably linked" refers to a functional positioning of the cis-regulatory element (e.g., promoter) so as to allow regulating expression of the selected nucleic acid sequence. For example, a promoter sequence may be located upstream of the selected nucleic acid sequence in terms of the direction of transcription and translation.

Preferably, the promoter in the nucleic acid construct of the present invention is a plant promoter which serves for directing expression of the heterologous nucleic acid molecule within plant cells.

It will be appreciated that novel nucleic acid sequences encoding intercalating elements such as set forth in SEQ ID NOs: 2, 4, 6 8 10 or 12 are contemplated per se or as part of a nucleic acid expression vector for expression in bacteria or plant cells.

As used herein the phrase "plant promoter" refers to a promoter sequence, including any additional regulatory elements added thereto or contained therein, is at least capable of inducing, conferring, activating or enhancing expression in a plant cell, tissue or organ, preferably a monocotyledonous or dicotyledonous plant cell, tissue, or organ. Such a promoter can be derived from a plant, bacterial, viral, fungal or animal origin. Such a promoter can be constitutive, i.e., capable of directing high level of gene expression in a plurality of plant tissues, tissue specific, i.e., capable of directing gene expression in a particular plant tissue or tissues, inducible, i.e., capable of directing gene expression under a stimulus, or chimeric, i.e., formed of portions of at least two different promoters.

Examples of constitutive plant promoters include, without being limited to, CaMV35S and CaMV19S promoters, FMV34S promoter, sugarcane bacilliform badnavirus promoter, CsVMV promoter, *Arabidopsis* ACT2/ACT8 actin promoter, *Arabidopsis* ubiquitin UBQ1 promoter, barley leaf thionin BTH6 promoter, and rice actin promoter.

According to a specific embodiment, the promoter is a constitutive promoter, such as a CaMV 35S promoter.

Other exemplary promoters useful for the methods of some embodiments of the invention are presented in Tables 3, 4, 5 and 6.

TABLE 3

Exemplary constitutive promoters for use in the performance of some embodiments of the invention

| Reference | Expression Pattern | Gene Source |
|---|---|---|
| McElroy etal, Plant Cell, 2: 163-171, 1990 | constitutive | Actin |
| Odell et al, Nature, 313: 810-812, 1985 | constitutive | CAMV 35S |
| Nilsson et al., Physiol. Plant 100: 456-462, 1997 | constitutive | CaMV 19S |
| de Pater et al, Plant J Nov; 2(6): 837-44, 1992 | constitutive | GOS2 |
| Christensen et al, Plant Mol. Biol. 18: 675-689, 1992 | constitutive | Ubiquitin |
| Bucholz et al, Plant Mol Biol. 25(5): 837-43, 1994 | constitutive | Rice cyclophilin |
| Lepetit et al, Mol. Gen. Genet. 231: 276-285, 1992 | constitutive | Maize H3 histone |
| An et al, Plant J. 10(1); 107-121, 1996 | constitutive | Actin 2 |

TABLE 4

Exemplary seed-preferred promoters for use in the performance of some embodiments of the invention

| Reference | Expression Pattern | Gene Source |
|---|---|---|
| Simon, et al., Plant Mol. Biol. 5. 191, 1985; Scofield, etal., J. Biol. Chem. 262: 12202, 1987.; Baszczynski, et al., Plant Mol. Biol. 14: 633, 1990. | Seed | Seed specific genes |
| Pearson' et al., Plant Mol. Biol. 18: 235-245, 1992. | Seed | Brazil Nut albumin |
| Ellis, et al. Plant Mol. Biol. 10: 203-214, 1988 | Seed | Legumin |
| Takaiwa, et al., Mol. Gen. Genet. 208: 15-22, 1986; Takaiwa, et al., FEBS Letts. 221: 43-47, 1987 | Seed | Glutelin (rice) |
| Matzke et al Plant Mol Biol, 143). 323-32 1990 | Seed | Zein |
| Stalberg, et al, Planta 199: 515-519, 1996 | Seed | napA |
| Mol Gen Genet 216: 81-90, 1989; NAR 17: 461-2, | Endosperm | wheat LMW and HMW, glutenin-1 |
| Albanietal, Plant Cell, 9: 171-184, 1997 | Seed | Wheat SPA |
| EMBO3: 1409-15, 1984 | Endosperm | wheat a, b and g gliadins |
| | Endosperm | Barley ltrl promoter |

TABLE 4-continued

Exemplary seed-preferred promoters for use in the performance of some embodiments of the invention

| Reference | Expression Pattern | Gene Source |
|---|---|---|
| Theor Appl Gen 98: 1253-62, 1999; Plant J 4: 343-55, 1993; Mol Gen Genet 250: 750-60, 1996 | Endosperm | barley B1, C, D hordein |
| Mena et al, The Plant Journal, 116(1): 53-62, 1998 | Endosperm | Barley DOF |
| EP99106056.7 | Endosperm | Biz2 |
| Vicente-Carbajosa et al., Plant J. 13: 629-640, 1998 | Endosperm | Synthetic promoter |
| Wu et al, Plant Cell Physiology 39(8) 885-889, 1998 | Endosperm | rice prolamin NRP33 |
| Wu et al, Plant Cell Physiology 398) 885-889, 1998 | Endosperm | rice -globulin Glb-1 |
| Sato et al, Proc. Nati. Acad. Sci. USA, 93: 8117-8122 | Embryo | rice OSH1 |
| Nakase et al. Plant Mol. Biol. 33: 513-S22, 1997 | Endosperm | rice alpha-globulin REB/OHP-1 |
| Trans Res 6: 157-68, 1997 | Endosperm | rice ADP-glucose PP |
| Plant J 12: 35-46, 1997 | Endosperm | maize ESR gene family |
| PMB 32: 1029-35, 1996 | Endosperm | sorgum gamma- kafirin |
| Postma-Haarsma ef al, Plant Mol. Biol. 39: 257-71, 1999 | Embryo | KNOX |
| Wu et at, J. Biochem., 123: 386, 1998 | Embryo and aleuton | rice oleosin |
| Cummins, etal., Plant Mol. Biol. 19: 873-876, 1992 | Seed (embryo and dry seed) | sunflower oleosin |

TABLE 5

Exemplary flower-specific promoters for use in the performance of the invention

| Reference | Expression Pattern | Gene Source |
|---|---|---|
| www.salus.medium.edu/mmg/tierney/html | Flowers | AtPRP4 |
| Van der Meer, et al., Plant Mol. Biol. 15, 95-109, 1990. | Flowers | chalene synthase (chsA) |
| Twell et al Mol. Gen Genet. 217: 240-245 (1989) | Anther | LAT52 |
| | Flowers | apetala- 3 |

TABLE 6

Alternative rice promoters for use in the performance of the invention

| expression | Gene | PRO # |
|---|---|---|
| transfer layer of embryo + calli | Metallothionein Mte | PR00001 |
| transfer layer of embryo | putative beta-amylase | PR00005 |
| Weak in roots | Putative cellulose synthase | PR00009 |
| | lipase (putative) | PR00012 |
| | Transferase (putative) | PR00014 |
| | peptidyl prolyl cis-trans isomerase (putative) | PR00016 |
| | Unknown | PR00019 |
| | prp protein (putative) | PR00020 |
| | noduline (putative) | PR00029 |

TABLE 6-continued

Alternative rice promoters for use in the performance of the invention

| expression | Gene | PRO # |
|---|---|---|
| seed | Proteinase inhibitor Rgpi9 | PR00058 |
| Weak in young flowers | beta expansine EXPB9 | PR00061 |
| young tissues + calli + embryo | Structural protein | PR00063 |
| | xylosidase (putative) | PR00069 |
| strong in endosperm | Prolamine 10 Kda | PR00075 |
| strong in endosperm | allergen RA2 | PR00076 |
| strong in endosperm | prolamine RP7 | PR00077 |
| | CBP80 | PR00078 |
| | starch branching enzyme I | PR00079 |
| transfer layer of embryo + calli | Metallothioneine-like ML2 | PR00080 |
| shoot | putative caffeoyl- CoA 3-0 methyltransferase | PR00081 |
| strong in endosperm | prolamine RM9 | PR00087 |
| strong in endosperm | prolamine RP6 | PR00090 |
| strong in endosperm | prolamine RP5 | PR00091 |
| | allergen RA5 | PR00092 |
| embryo | putative methionine aminopeptidase | PR00095 |
| | ras-related GTP binding protein | PR00098 |
| | beta expansine EXPB1 | PR00104 |
| | Glycine rich protein | PR00105 |
| | metallothionein like protein (putative) | PR00108 |
| | RCc3 strong root | PR00110 |
| weak discrimination center/shoot meristem | uclacyanin 3-like protein | PR00111 |
| very weak meristem specific | 26S proteasome regulatory particle non-ATPase subunit 11 | PR00116 |
| weak in endosperm | putative 40S ribosomal protein | PR00117 |
| very weak in shoot | chlorophyll a/lo-binding protein precursor (Cab27) | PR00122 |
| Strong leaves | putative protochlorophyllide reductase | PR00123 |
| strong discrimination center shoot meristem | metallothionein RiCMT | PR00126 |
| Strong constitutive | GOS2 | PR00129 |
| | GOS9 | PR00131 |
| very weak meristem specific | chitinase Cht-3 | PR00133 |
| Strong in endosperm | alpha- globulin | PR00135 |
| Weak in endosperm | alanine aminotransferase | PR00136 |
| | Cyclin A2 | PR00138 |
| | Cyclin D2 | PR00139 |
| | Cyclin D3 | PR00140 |
| Shoot and seed | Cyclophyllin 2 | PR00141 |
| medium constitutive | sucrose synthase SS1 (barley) | PR00146 |
| weak in endosperm | trypsin inhibitor ITR1 (barley) | PR00147 |
| strong constitutive | ubiquitine 2 with intron | PR00149 |
| Embryo and stress | WSI18 | PR00151 |
| | HVA22 homologue (putative) | PR00156 |
| | EL2 | PR00157 |
| medium constitutive in young plants | Aquaporine | PR00169 |
| Strong constitutive | High mobility group protein | PR00170 |
| weak constitutive | reversibly glycosylated protein RGP1 | PR00171 |
| shoot | cytosolic MDH | PR00173 |
| Embryo and stress | RAB21 | PR00175 |
| | CDPK7 | PR00176 |
| very weak in meristem | Cdc2-1 | PR00177 |
| | sucrose synthase 3 | PR00197 |
| | OsVP1 | PRO0198 |
| very weak in young plant meristem | OSH1 | PRO0200 |
| | putative chlorophyllase | PRO0208 |
| | OsNRT1 | PRO0210 |
| | EXP3 | PRO0211 |
| | phosphate transporter OjPT1 | PRO0216 |
| aleurone + embryo | oleosin 18 kd | PRO0218 |
| | ubiquitine 2 without intron | PRO0219 |
| | RFL | PRO0220 |

TABLE 6-continued

| Alternative rice promoters for use in the performance of the invention | | |
|---|---|---|
| expression | Gene | PRO # |
| not detected | maize UBI delta intron | PRO0221 |
| | glutelin-1 | PRO0223 |
| | fragment of prolamin RP6 promoter | PRO0224 |
| | 4xABRE | PRO0225 |
| | glutelin OSGLUA3 | PRO0226 |
| | BLZ-2_short (barley) | PRO0227 |
| | BLZ-2_long (barley) | PR00228 |

The nucleic acid construct of the present invention may also comprise an additional nucleic acid sequence encoding an endoplasmic reticulum signal peptide that allows transport of the dominant negative T3SS propeptide to the endoplasmic reticulum and through the secretory pathway. Such a signal peptide is typically linked in frame to the amino terminus of a polypeptide (i.e. upstream thereto) and directs the encoded polypeptide into a cell's secretory pathway and its final secretion therefrom (e.g. to the apoplast).

Exemplary secretion signal sequences which direct polypeptides via the ER to the extracellular space include the plant secretion leader peptide from sp|Q56YT0|LAC3_At Laccase (SEQ ID NO: 16) and the plant secretion leader peptide from tr|Q6TDS6|Q6TDS6_GOSAR (SEQ ID NO: 17).

Additional exemplary signal peptides that may be used herein include the tobacco pathogenesis related protein (PR-S) signal sequence (Sijmons et al., 1990, Bio/technology, 8:217-221), lectin signal sequence (Boehn et al., 2000, Transgenic Res, 9(6):477-86), signal sequence from the hydroxyproline-rich glycoprotein from *Phaseolus vulgaris* (Yan et al., 1997, Plant Phyiol. 115(3):915-24 and Corbin et al., 1987, Mol Cell Biol 7(12):4337-44), potato patatin signal sequence (Iturriaga, G et al., 1989, Plant Cell 1:381-390 and Bevan et al., 1986, Nuc. Acids Res. 41:4625-4638.) and the barley alpha amylase signal sequence (Rasmussen and Johansson, 1992, Plant Mol. Biol. 18(2):423-7).

According to an embodiment of the present invention, the nucleic acid construct of the present invention may further comprise a translation enhancer such as an omega translation enhancer.

Nucleic acid sequences of the polypeptides of some embodiments of the invention may be optimized for plant expression. Examples of such sequence modifications include, but are not limited to, an altered G/C content to more closely approach that typically found in the plant species of interest, and the removal of codons atypically found in the plant species commonly referred to as codon optimization.

The phrase "codon optimization" refers to the selection of appropriate DNA nucleotides for use within a structural gene or fragment thereof that approaches codon usage within the plant of interest. Therefore, an optimized gene or nucleic acid sequence refers to a gene in which the nucleotide sequence of a native or naturally occurring gene has been modified in order to utilize statistically-preferred or statistically-favored codons within the plant. The nucleotide sequence typically is examined at the DNA level and the coding region optimized for expression in the plant species determined using any suitable procedure, for example as described in Sardana et al. (1996, Plant Cell Reports 15:677-681). In this method, the standard deviation of codon usage, a measure of codon usage bias, may be calculated by first finding the squared proportional deviation of usage of each codon of the native gene relative to that of highly expressed plant genes, followed by a calculation of the average squared deviation. The formula used is: 1 SDCU=n=1 N [(Xn−Yn)/Yn] 2/N, where Xn refers to the frequency of usage of codon n in highly expressed plant genes, where Yn to the frequency of usage of codon n in the gene of interest and N refers to the total number of codons in the gene of interest. A table of codon usage from highly expressed genes of dicotyledonous plants is compiled using the data of Murray et al. (1989, Nuc Acids Res. 17:477-498).

One method of optimizing the nucleic acid sequence in accordance with the preferred codon usage for a particular plant cell type is based on the direct use, without performing any extra statistical calculations, of codon optimization tables such as those provided on-line at the Codon Usage Database through the NIAS (National Institute of Agrobiological Sciences) DNA bank in Japan (www(dot)kazusa(dot)or(dot)jp/codon/). The Codon Usage Database contains codon usage tables for a number of different species, with each codon usage table having been statistically determined based on the data present in Genbank.

By using the above tables to determine the most preferred or most favored codons for each amino acid in a particular species (for example, rice), a naturally-occurring nucleotide sequence encoding a protein of interest can be codon optimized for that particular plant species. This is effected by replacing codons that may have a low statistical incidence in the particular species genome with corresponding codons, in regard to an amino acid, that are statistically more favored. However, one or more less-favored codons may be selected to delete existing restriction sites, to create new ones at potentially useful junctions (5' and 3' ends to add signal peptide or termination cassettes, internal sites that might be used to cut and splice segments together to produce a correct full-length sequence), or to eliminate nucleotide sequences that may negatively effect mRNA stability or expression.

The naturally-occurring encoding nucleotide sequence may already, in advance of any modification, contain a number of codons that correspond to a statistically-favored codon in a particular plant species. Therefore, codon optimization of the native nucleotide sequence may comprise determining which codons, within the native nucleotide sequence, are not statistically-favored with regards to a particular plant, and modifying these codons in accordance with a codon usage table of the particular plant to produce a codon optimized derivative. A modified nucleotide sequence may be fully or partially optimized for plant codon usage provided that the protein encoded by the modified nucleotide sequence is produced at a level higher than the protein encoded by the corresponding naturally occurring or native gene. Construction of synthetic genes by altering the codon usage is described in for example PCT Patent Application No. 93/07278.

Thus, some embodiments of the invention encompasses nucleic acid sequences described hereinabove; fragments thereof, sequences hybridizable therewith, sequences homologous thereto, sequences orthologous thereto, sequences encoding similar polypeptides with different codon usage, altered sequences characterized by mutations, such as deletion, insertion or substitution of one or more nucleotides, either naturally occurring or man induced, either randomly or in a targeted fashion.

Plant cells may be transformed stably or transiently with the nucleic acid constructs of some embodiments of the invention. In stable transformation, the nucleic acid molecule of some embodiments of the invention is integrated into the plant genome and as such it represents a stable and inherited trait. In transient transformation, the nucleic acid molecule is expressed by the cell transformed but it is not integrated into the genome and as such it represents a transient trait.

There are various methods of introducing foreign genes into both monocotyledonous and dicotyledonous plants (Potrykus, I., Annu. Rev. Plant. Physiol., Plant. Mol. Biol. (1991) 42:205-225; Shimamoto et al., Nature (1989) 338: 274-276).

The principle methods of causing stable integration of exogenous DNA into plant genomic DNA include two main approaches:

(i) *Agrobacterium*-mediated gene transfer: Klee et al. (1987) Annu. Rev. Plant Physiol. 38:467-486; Klee and Rogers in Cell Culture and Somatic Cell Genetics of Plants, Vol. 6, Molecular Biology of Plant Nuclear Genes, eds. Schell, J., and Vasil, L. K., Academic Publishers, San Diego, Calif. (1989) p. 2-25; Gatenby, in Plant Biotechnology, eds. Kung, S. and Arntzen, C. J., Butterworth Publishers, Boston, Mass. (1989) p. 93-112.

(ii) direct DNA uptake: Paszkowski et al., in Cell Culture and Somatic Cell Genetics of Plants, Vol. 6, Molecular Biology of Plant Nuclear Genes eds. Schell, J., and Vasil, L. K., Academic Publishers, San Diego, Calif. (1989) p. 52-68; including methods for direct uptake of DNA into protoplasts, Toriyama, K. et al. (1988) Bio/Technology 6:1072-1074. DNA uptake induced by brief electric shock of plant cells: Zhang et al. Plant Cell Rep. (1988) 7:379-384. Fromm et al. Nature (1986) 319:791-793. DNA injection into plant cells or tissues by particle bombardment, Klein et al. Bio/Technology (1988) 6:559-563; McCabe et al. Bio/Technology (1988) 6:923-926; Sanford, Physiol. Plant. (1990) 79:206-209; by the use of micropipette systems: Neuhaus et al., Theor. Appl. Genet. (1987) 75:30-36; Neuhaus and Spangenberg, Physiol. Plant. (1990) 79:213-217; glass fibers or silicon carbide whisker transformation of cell cultures, embryos or callus tissue, U.S. Pat. No. 5,464,765 or by the direct incubation of DNA with germinating pollen, DeWet et al. in Experimental Manipulation of Ovule Tissue, eds. Chapman, G. P. and Mantell, S. H. and Daniels, W. Longman, London, (1985) p. 197-209; and Ohta, Proc. Natl. Acad. Sci. USA (1986) 83:715-719.

The *Agrobacterium* system includes the use of plasmid vectors that contain defined DNA segments that integrate into the plant genomic DNA. Methods of inoculation of the plant tissue vary depending upon the plant species and the *Agrobacterium* delivery system. A widely used approach is the leaf disc procedure which can be performed with any tissue explant that provides a good source for initiation of whole plant differentiation. Horsch et al. in Plant Molecular Biology Manual A5, Kluwer Academic Publishers, Dordrecht (1988) p. 1-9. A supplementary approach employs the *Agrobacterium* delivery system in combination with vacuum infiltration. The *Agrobacterium* system is especially viable in the creation of transgenic dicotyledonous plants.

There are various methods of direct DNA transfer into plant cells. In electroporation, the protoplasts are briefly exposed to a strong electric field. In microinjection, the DNA is mechanically injected directly into the cells using very small micropipettes. In microparticle bombardment, the DNA is adsorbed on microprojectiles such as magnesium sulfate crystals or tungsten particles, and the microprojectiles are physically accelerated into cells or plant tissues.

Following stable transformation plant propagation is exercised. The most common method of plant propagation is by seed. Regeneration by seed propagation, however, has the deficiency that due to heterozygosity there is a lack of uniformity in the crop, since seeds are produced by plants according to the genetic variances governed by Mendelian rules. Basically, each seed is genetically different and each will grow with its own specific traits. Therefore, it is preferred that the transformed plant be produced such that the regenerated plant has the identical traits and characteristics of the parent transgenic plant. Therefore, it is preferred that the transformed plant be regenerated by micropropagation which provides a rapid, consistent reproduction of the transformed plants.

Micropropagation is a process of growing new generation plants from a single piece of tissue that has been excised from a selected parent plant or cultivar. This process permits the mass reproduction of plants having the preferred tissue expressing the fusion protein. The new generation plants which are produced are genetically identical to, and have all of the characteristics of, the original plant. Micropropagation allows mass production of quality plant material in a short period of time and offers a rapid multiplication of selected cultivars in the preservation of the characteristics of the original transgenic or transformed plant. The advantages of cloning plants are the speed of plant multiplication and the quality and uniformity of plants produced.

Micropropagation is a multi-stage procedure that requires alteration of culture medium or growth conditions between stages. Thus, the micropropagation process involves four basic stages: Stage one, initial tissue culturing; stage two, tissue culture multiplication; stage three, differentiation and plant formation; and stage four, greenhouse culturing and hardening. During stage one, initial tissue culturing, the tissue culture is established and certified contaminant-free. During stage two, the initial tissue culture is multiplied until a sufficient number of tissue samples are produced to meet production goals. During stage three, the tissue samples grown in stage two are divided and grown into individual plantlets. At stage four, the transformed plantlets are transferred to a greenhouse for hardening where the plants' tolerance to light is gradually increased so that it can be grown in the natural environment.

Although stable transformation is presently preferred, transient transformation of leaf cells, meristematic cells or the whole plant is also envisaged by some embodiments of the invention.

Transient transformation can be effected by any of the direct DNA transfer methods described above or by viral infection using modified plant viruses.

Viruses that have been shown to be useful for the transformation of plant hosts include CaMV, TMV and BV. Transformation of plants using plant viruses is described in U.S. Pat. No. 4,855,237 (BGV), EP-A 67,553 (TMV), Japanese Published Application No. 63-14693 (TMV), EPA 194,809 (BV), EPA 278,667 (BV); and Gluzman, Y. et al., Communications in Molecular Biology: Viral Vectors, Cold Spring Harbor Laboratory, New York, pp. 172-189 (1988). Pseudovirus particles for use in expressing foreign DNA in many hosts, including plants, is described in WO 87/06261.

Construction of plant RNA viruses for the introduction and expression of non-viral exogenous nucleic acid sequences in plants is demonstrated by the above references as well as by Dawson, W. O. et al., Virology (1989) 172:285-292; Takamatsu et al. EMBO J. (1987) 6:307-311; French et al. Science (1986) 231:1294-1297; and Takamatsu et al. FEBS Letters (1990) 269:73-76.

When the virus is a DNA virus, suitable modifications can be made to the virus itself. Alternatively, the virus can first be cloned into a bacterial plasmid for ease of constructing the desired viral vector with the foreign DNA. The virus can then be excised from the plasmid. If the virus is a DNA virus, a bacterial origin of replication can be attached to the viral DNA, which is then replicated by the bacteria. Transcription and translation of this DNA will produce the coat protein which will encapsidate the viral DNA. If the virus is an RNA virus, the virus is generally cloned as a cDNA and inserted into a plasmid. The plasmid is then used to make all of the constructions. The RNA virus is then produced by transcribing the viral sequence of the plasmid and translation of the viral genes to produce the coat protein(s) which encapsidate the viral RNA.

Construction of plant RNA viruses for the introduction and expression in plants of non-viral exogenous nucleic acid sequences such as those included in the construct of some embodiments of the invention is demonstrated by the above references as well as in U.S. Pat. No. 5,316,931.

In one embodiment, a plant viral nucleic acid is provided in which the native coat protein coding sequence has been deleted from a viral nucleic acid, a non-native plant viral coat protein coding sequence and a non-native promoter, preferably the subgenomic promoter of the non-native coat protein coding sequence, capable of expression in the plant host, packaging of the recombinant plant viral nucleic acid, and ensuring a systemic infection of the host by the recombinant plant viral nucleic acid, has been inserted. Alternatively, the coat protein gene may be inactivated by insertion of the non-native nucleic acid sequence within it, such that a protein is produced. The recombinant plant viral nucleic acid may contain one or more additional non-native subgenomic promoters. Each non-native subgenomic promoter is capable of transcribing or expressing adjacent genes or nucleic acid sequences in the plant host and incapable of recombination with each other and with native subgenomic promoters. Non-native (foreign) nucleic acid sequences may be inserted adjacent the native plant viral subgenomic promoter or the native and a non-native plant viral subgenomic promoters if more than one nucleic acid sequence is included. The non-native nucleic acid sequences are transcribed or expressed in the host plant under control of the subgenomic promoter to produce the desired products.

In a second embodiment, a recombinant plant viral nucleic acid is provided as in the first embodiment except that the native coat protein coding sequence is placed adjacent one of the non-native coat protein subgenomic promoters instead of a non-native coat protein coding sequence.

In a third embodiment, a recombinant plant viral nucleic acid is provided in which the native coat protein gene is adjacent its subgenomic promoter and one or more non-native subgenomic promoters have been inserted into the viral nucleic acid. The inserted non-native subgenomic promoters are capable of transcribing or expressing adjacent genes in a plant host and are incapable of recombination with each other and with native subgenomic promoters. Non-native nucleic acid sequences may be inserted adjacent the non-native subgenomic plant viral promoters such that said sequences are transcribed or expressed in the host plant under control of the subgenomic promoters to produce the desired product.

In a fourth embodiment, a recombinant plant viral nucleic acid is provided as in the third embodiment except that the native coat protein coding sequence is replaced by a non-native coat protein coding sequence.

The viral vectors are encapsidated by the coat proteins encoded by the recombinant plant viral nucleic acid to produce a recombinant plant virus. The recombinant plant viral nucleic acid or recombinant plant virus is used to infect appropriate host plants. The recombinant plant viral nucleic acid is capable of replication in the host, systemic spread in the host, and transcription or expression of foreign gene(s) (isolated nucleic acid) in the host to produce the desired protein.

In addition to the above, the nucleic acid molecule of some embodiments of the invention can also be introduced into a chloroplast genome thereby enabling chloroplast expression.

A technique for introducing exogenous nucleic acid sequences to the genome of the chloroplasts is known. This technique involves the following procedures. First, plant cells are chemically treated so as to reduce the number of chloroplasts per cell to about one. Then, the exogenous nucleic acid is introduced via particle bombardment into the cells with the aim of introducing at least one exogenous nucleic acid molecule into the chloroplasts. The exogenous nucleic acid is selected such that it is integratable into the chloroplast's genome via homologous recombination which is readily effected by enzymes inherent to the chloroplast. To this end, the exogenous nucleic acid includes, in addition to a gene of interest, at least one nucleic acid stretch which is derived from the chloroplast's genome. In addition, the exogenous nucleic acid includes a selectable marker, which serves by sequential selection procedures to ascertain that all or substantially all of the copies of the chloroplast genomes following such selection will include the exogenous nucleic acid. Further details relating to this technique are found in U.S. Pat. Nos. 4,945,050; and 5,693,507 which are incorporated herein by reference. A polypeptide can thus be produced by the protein expression system of the chloroplast and become integrated into the chloroplast's inner membrane.

According to an additional aspect of the invention there is provided a host cell comprising the nucleic acid expression vector of the present invention.

A "host cell" of the present invention refers to a new individual cell arising as a result of the introduction into the cell of the nucleic acid expression vector comprising the nucleic acid sequence encoding a dominant negative T3SS protein. According to a specific embodiment, the host cell is a plant cell. The host cell may contain the nucleic acid construct as an extra-chromosomally (episomal) replicating molecule, or alternatively, may comprises the chimeric gene integrated in the nuclear or plastid genome of the host cell.

According to a further aspect of the invention there is provided a genetically modified plant comprising the nucleic acid expression vector of the present invention.

According to a further aspect of the invention there is provided a genetically modified plant expressing an exogenous polynucleotide encoding a dominant negative T3SS protein as set forth in SEQ ID NO: 2, 4, 6, 8, 10 or 12.

According to a specific embodiment, the genetically modified plant expressing the dominant negative T3SS protein comprises enhanced resistance to a bacterial pathogen compared to a non modified plant (as described in detail hereinabove).

It will be appreciated that when referring to a genetically modified plant or plant cell, the present inventors also refer to progeny arising therefrom.

Progeny resulting from breeding or from transforming plants can be selected, by verifying presence of exogenous mRNA and/or polypeptides by using nucleic acid or protein probes (e.g. antibodies). Alternatively, expression of the dominant negative T3SS proteins of the present invention may be verified by measuring enhanced resistance to bacterial pathogens by infecting the genetically modified plant and a wild-type (i.e. non-modified plant of the same type) and comparing the disease in the plant (e.g. observing the wilting of the plant).

The present invention further provides methods of evaluating resistance of a plant to a bacterial pathogen, the method comprising: (a) expressing within the plant an exogenous nucleic acid sequence encoding a dominant negative T3SS protein and a cis acting regulatory element capable of driving transcription of the nucleic acid sequence in a plant cell; (b) subjecting the plant to a bacterial pathogen; and (c) comparing the disease in the plant to a wild-type plant grown and infected with the bacterial pathogen under the same conditions.

The bacterial pathogens as described herein may cause a variety of diseases in plants. Thus, for example, *R. solanacearum* may cause wilting disease, *P. agarici* may cause drippy gill disease (e.g. in cultivated mushrooms), *P. tolaasii* may cause bacterial blotch (e.g. in cultivated mushrooms), *X. campestris* may causes black rot (e.g. in crucifers such as *Brassica* and *Arabidopsis*), *X. oryzae* may cause bacterial blight (e.g. in rice), *E. amylovora* may cause fireblight disease (e.g. in apples and pears), *E. carotovora* may cause bacterial soft rot disease.

Thus, for example, for wilting disease, symptoms are typically scored on a daily basis for 2 to 4 weeks by a rater (blind to treatment identity) on a 0 to 4 disease index, where 0 indicates no disease, 1 indicates 1 to 25% of leaves wilted, 2 indicates 25 to 50% of leaves wilted, 3 indicates 51 to 75% of leaves wilted, and 4 indicates 76 to 100% of leaves wilted.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Generation and Expression of Intercalating Blocking Elements of *Ralstonia solanacearum* Type III Secretion System (T3SS) Needle Channel in Plants Materials and Experimental Procedures Gene Synthesis, Codon Usage Expression:

T3SS-IBE variations were designed based on the 3D template of a T3SS needle from *Shigela flexneri* (MxiH) previously described [Deane et al., PNAS 2006 103: 12529-33] representing the hypothetical natural structure model of HrpY (FIGS. 2A-2F).

*Ralstonia solanacearum* (Rs) HrpY intercalating blocking element (hY-IBE) genes were synthetically synthesized and optimized for target plant codon usage. Plant specific secretion leader peptides were fused to the 5' of each hY-IBE to transport and localize the mature proteins in the apoplast or cell wall.

Cloning in Binary Vector and Transformation:

Synthetic fragments consisting of IBE's 1-6 coding regions with 5' untranslated enhancer were cloned downstream to a CaMV 35S constitutive promoter and upstream to a NOS terminator in a plant transformation vector based on pBI121 plasmid (NCBI genebank ID# AF485783) using XbaI and SacI restriction sites (FIG. 7A).

An agro-transformation protocol was used for Tomato plants, *Arabidopsis* plants and *Eucalyptus* plants as previously described for tobacco plants [see e.g. Svab, Z., P. Hajdukiewicz and P. Maliga. (1975) Transgenic tobacco plants by co-cultivation of leaf disks with pPZP *Agrobacterium* binary vectors. In "Methods in Plant Molecular Biology—A Laboratory Manual", P. Maliga, D. Klessig, A. Cashmore, W. Gruissem and J. Varner, eds. Cold Spring Harbor Press: 55-77] and for *eucalyptus* plants [Spokevicius A V., Van Beveren K., Leitch M A and Bossinger G. (2005) *Agrobacterium*-mediated in vitro transformation of wood-producing stem segments in eucalypts. Plant Cell Reports, Volume 23(9), 617-624].

Transformation of Tomato Plants

Tomato plants were transformed as previously described [Qiu et al., Scientia Horticulturae 112 (2007) 172-175]. In short:

Plant Material

Seeds of tomato, *L. esculentum* cv M82 were surface sterilized for 30 s in a 70% alcohol and washed with sterilized water for 10 s and then sterilized for 10 min in a 1% hypochlorite solution and washed two times with sterilized water for 30 min before sowing on Medium A (as described in Table 7 below). Seeds were sown in a Magenta box and germinated at 24° C. during a 16 h light period and 8 h dark period. Cotyledons of half upright seedling were used after 4-5 days of germination.

Media, Antibiotics and Hormones

The media MSBS (M0404) were obtained as powders from Sigma Chemical Co., and stored at 2-8° C. Sucrose and glucose were stored at room temperature. Kanamycin, carbenicillin, cefotaxime, rifamicin, ZR, IAA, IBA were further used in the plant mediums (as described in Table 7 below).

TABLE 7

Plant media used in the tomato transformation protocol (incorporated herein from Qiu et al., *Scientia Horticulturae* 112 (2007) 172-175)

Composition of the various media

| | Medium | | | | | |
|---|---|---|---|---|---|---|
| MSB5 salts | A, 0.5x | B, 1x | B1, 1x | C, 1x | D, 1x | E, 1x |
| Sucrose (%) | 1 | 3 | 3 | 3 | N | 1 |
| Glucose | N | N | N | N | 1% | N |
| Agar (Daichin) (%) | 0.60 | 0.60 | N | 0.60 | 0.60 | 0.60 |
| pH | 5.8 | 5.8 | 5.8 | 5.8 | 5.8 | 5.8 |
| IAA 0.1 mg/L | − | + | − | + | + | − |
| ZR 2 mg/L | − | + | − | + | + | − |
| IBA 0.1 mg/L | − | − | − | − | − | + |
| Cefotaxime 500 mg/L | − | − | − | + | + | + |
| Carbenicillin 500 mg/L | − | − | − | − | + | − |
| Kanamycin (mg/L) | − | − | − | − | 100 | 30 |

Bacterial Strains and Plasmids

For transformation experiments, *Agrobacterium* containing the gene of interest was used. The binary vector used in this study was pBI121 which contained the nptII gene as selection maker; The *Agrobacterium* strains used in this study harbored a rifampicin selection maker. Bacteria were grown overnight in LB medium with antibiotic (rifamicin 30 mg/L, kanamycin 100 mg/L), diluted to OD600=0.2 and grown to expected OD 600 in LB without antibiotics. Bacterial suspensions were centrifuged at 4000 rpm for 15 min in a 50 mL Falcon tube. Bacteria were resuspended in B1 medium, and used for cocultivation experiments.

Transformation Protocol

The cotyledons were prepared as follows: The excision of the cotyledons from the seedling was done extremely carefully to prevent the issue from bruising. Isolated cotyledons were cut on the basal and the lateral side only and placed upside up onto Medium B (as described in Table 7 above). Approximately 50 explants were placed on a single Petri dish and incubated overnight. The next day explants were carefully submerged in the *Agrobacterium* inoculum in a Petri dish for 20 min. They were blotted dry on sterile paper and transferred to the new Medium B. After 72 h, explants were transferred to plates containing Medium C (as described in Table 7 above). After incubation for another 72 h, the explants were transferred to selection Medium D (as described in Table 7 above). Every 3 weeks the explants were subcultured to the same medium. After approximately 6-8 weeks, shoots were excised and transferred to Medium E (as described in Table 7 above). Transformation frequency was expressed as the percentage of the number of cotyledons from which shoots were recovered, with regard to the total number of explants incubated.

Expression and Cloning Confirmation:

Plant genome integration and expression of T3SS-IBE's was analyzed using conventional molecular methods such as PCR, RT-PCR [as previously described, see e.g. Sambrook J. and Russell D W., Molecular Cloning: A Laboratory Manual, Cold Spring Harbor Laboratory Press; 3rd edition (Jan. 15, 2001)] with IBE's 1-6 specific primers and Western analysis with anti-IBE's polyclonal antibody. Specifically, the PCR primers used for HrpY mutant 1 were Forward primer: TCTCTTTGCTCTCCTTTATAGCCCTAC and Reverse primer: TCGCAGCGTCTAACATATCTTGTT-GTC (SEQ ID NOs: 95-96, respectively); the primers used for HrpY mutant 2 were Forward primer: GTCACATGGT-TCGTTGGTGTACTCTTC and Reverse primer: CATCTGGGTTCTATTCAGCGCATTTTG (SEQ ID NOs: 97-98, respectively); and the primers used for or HrpY mutant 6 were Forward primer: GTCTTGTTCCTGTCTAC-CTTGCTCC and Reverse primer: GAGATTAG-GTCTTTCGCAGCTTTGG (SEQ ID NOs: 93-94, respectively).

BioAssays:

Transgenic plants are subjected to a bioassay for testing the resistance level of each transgenic line compared to wild type (i.e. not expressing the IBE gene). Three bioassay methods are applied:

1. Soaked soil—Unwounded 19 to 21 day old plants are inoculated by pouring a bacterial suspension onto the soil to a final density of approximately $1\times10^8$ CFU/g soil, followed by incubation at 28° C. Control plants are mock-inoculated with sterile water. Symptoms are scored daily by a rater blind to treatment identity on a 0-to-4 disease index, where 0 indicates no disease, 1 indicates 1 to 25% of leaves wilted, 2 indicates 25 to 50% of leaves wilted, 3 indicates 51 to 75% of leaves wilted, and 4 indicates 76 to 100% of leaves wilted. Each experiment encompasses 16 plants per treatment, and experiments are repeated at least three times.

2. Petiole inoculation—Lower leaf of unwounded 19 to 21 day old plants are cut and 2 μl of bacteria suspension with a final density of approximately $1\times10^8$ CFU/ml is dropped on the open petiole. Control plants are mock-inoculated with sterile water. Symptoms are scored daily by a rater blind to treatment identity on a 0-to-4 disease index, where 0 indicates no disease, 1 indicates 1 to 25% of leaves wilted, 2 indicates 25 to 50% of leaves wilted, 3 indicates 51 to 75% of leaves wilted, and 4 indicates 76 to 100% of leaves wilted. Each experiment encompasses 16 plants per treatment, and experiments are repeated at least three times.

3. Stem inoculation—Unwounded 19 to 21 day old plants are inoculated by cutting the stem with a sterile knife vertically. The wound, 1 cm long and 0.5 cm deep is injected with 100 μl of bacteria suspension with a final density of approximately $1\times10^8$ CFU/ml. Control plants are mock-inoculated with sterile water. Symptoms are scored daily by a rater blind to treatment identity on a 0-to-4 disease index, where 0 indicates no disease, 1 indicates 1 to 25% of leaves wilted, 2 indicates 25 to 50% of leaves wilted, 3 indicates 51 to 75% of leaves wilted, and 4 indicates 76 to 100% of leaves wilted. Each experiment contained 16 plants per treatment, and experiments are repeated at least three times.

Results

The present inventors generated plant-expressed blocking elements of *Ralstonia solanacearum* (Rs) type III secretion system (T3SS) needle channel (Intercalating Blocking Elements of T3SS or T3SS-IBE), for protection of plants from wilt disease, using structural modifications of HrpY protein, the building monomer of the needle. The structurally modified HrpY (SEQ ID NOs: 2, 4, 6, 8, 10 and 12 and depicted in detail in FIGS. 2A-2F, 3A-3D, 4A-4C, 5A-5C and 6A-6D), expressed in transgenic plants (crops and woody), is incorporated into the native pilus of Rs, functionally deactivating it and preventing or decreasing Rs bacterial infection in the transgenic plant compared to wild type plants. The transgenic plant that expresses the T3SS-IBEs is designed to secrete the T3SS-IBE outside of the cell where the T3SS-IBE is assembled into the pilus of the attacking Rs rendering the pilus non-functional or dysfunctional. Bacteria with structurally modified plant-derived protein intercalated in its pilus will render the T3SS nonfunctional and thus are not able to overcome the plant's natural defense. Such transgenic resistant plants are able to resist infection by Rs.

T3SS-IBE variations were designed based on the 3D template of a T3SS needle from *Shigela flexneri* (MxiH) previously described [Deane et al., PNAS 2006 103: 12529-33]. Based on this model, structural modifications of Rs HrpY were planned generating modified T3SS needle monomers that intercalate within the needle structure and block the needle channel, the conduit, in which plant cell wall-degrading pectinases, endo-glucanases, and virulence EPS and effector proteins are translocated into or through the host cell wall (FIGS. 1A-1C). Thus, the structurally modified pilus comprises protein domains which are located in the conduit of the pilus and thus are understood to functionally and physically block the conduit. Such structurally unstable pilus also terminate their assembly early resulting in relatively short pili further damaging their functionality and ability to transfer proteins to the plant. This rational design is based on preserving and utilizing the native HrpY subunit-subunit interaction sites while incorporating translationally fused channel-blocking peptide and/or deforming structures of alpha-helices. Plant secretion signals were included in these T3SS-IBEs to enable secretion from the plant cell to the extracellular space.

As described in the 'Materials and Experimental Procedures' section above, wilt resistant (WiltR) tomato plants were generated by transforming the tomato plants with constructs carrying *Ralstonia solanacearum* HrpY mutants 1, 2 or 6 (SEQ ID NOs: 1, 3 and 11, respectively). These plants were further analyzed by genomic PCR and semi-quantitative RT-PCR using specific primers for HrpY mutant 1 (SEQ ID NOs: 95-96), HrpY mutant 2 (SEQ ID NOs: 97-98) or HrpY mutant 6 (SEQ ID NOs: 93-94). Expression of the HrpY mutants 1, 2 or 6 was determined (see FIGS. 11A-11C, 12A-12C and 10A-10C, respectively) in the transformed tomato plants.

Example 2

Generation and Expression of T3SS-IBEs of Different Bacteria in Plants

In addition to the IBEs described in Example 1 above, other IBEs are being developed and identified for other gram negative bacteria using the methods described above. For example, IBEs are developed by mapping binding regions of pilus building block proteins, identifying candidate peptides that bind and integrate into the native pilus during its in vivo formation, modifying the candidate peptide to render the conduit incapable of secreting effector proteins and producing modified candidate IBEs.

Modifications may include those based on any of the following principles:

Conceptually the native proteins can be modified on the basis of one or more of several different approaches including the following:

1. Addition of a translation fusion to the N-terminal region of the native protein as in IBEs 1, 2 and 3 with (IBE 1&3) or without (IBE 2) and before (IBE 1) or after (IBE 3) the native N-terminal domain (see FIGS. 3A-3D, 4A-4C and 7C).

2. Addition of a translational fusion to the C-terminal region of the native protein as in IBE 4 with or without an amino acid bridge which allows rotational movement of the translational fusion fragment (see FIGS. 5A-5C and 7C). Such a bridge can be one or more glycine or alanine residues for example.

3. Addition of Proline amino acid to random points along the native building block sequence as in IBE 5 or 6 (see FIGS. 6A-6D and 7C).

4. Pentapeptide inserts.

Example 3

Generation and Expression of Modified *Ralstonia solanacearum* Translocon Proteins (PopF1) in Plants Another approach taken by the present inventors is to over-express wild-type (wt) and modified Rs translocon proteins (e.g. PopF1 or PopF2) in transgenic plants. PopF1 and PopF2 are building blocks of the needle gate and play an important role in virulence and hypersensitive response (HR) in plants Wt and modified PopF1/F2 proteins arrest T3SS assembly due to interactions with a premature needle. The bacterial controlled needle extension and the translocon proteins are normally extracted at the final stage of the process. Transgenic translocon proteins, which interact with the needle prematurely, interfere with the controlled sequential T3SS assembly and deactivate it. Thus, modified PopF1/F2 proteins are incorporated into the translocon gate and block it or structurally deform it to cause dysfunctionality. Taken together, the present teachings will enable exportation of the wt and modified PopF1 proteins to the apoplast/cell wall by the transgenic plants.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A nucleic acid expression vector comprising a nucleic acid sequence encoding a secreted dominant negative Type III secretion system (T3SS) protein and a heterologous cis acting regulatory element which drives transcription of said nucleic acid sequence in a plant cell, wherein said nucleic acid sequence encodes for the polypeptide set forth in SEQ ID NO: 2, 4, 6, 8, 10 or 12, said vector further comprising an additional nucleic acid sequence encoding a secretion signal peptide upstream to, and in frame with said nucleic acid sequence encoding said dominant negative T3SS protein for secretion of said nucleic acid sequence from said plant cell, and wherein said dominant negative T3SS protein mediates assembly of a dysfunctional needle complex.

2. A method of generating a plant comprising enhanced resistance to a *Ralstonia solanacearum* pathogen compared to a non modified plant, the method comprising introducing into a plant or plant cell the nucleic acid expression vector of claim 1, thereby generating the plant comprising enhanced resistance to the *Ralstonia solanacearum* compared to the non modified plant.

3. The nucleic acid expression vector of claim 1, wherein said nucleic acid sequence comprises SEQ ID NO: 1, 3, 5, 7, 9 or 11.

4. The nucleic acid expression vector of claim 1, wherein said heterologous cis acting regulatory element comprises a promoter sequence.

5. The nucleic acid expression vector of claim 4, wherein said promoter sequence is CaMV 35S promoter.

6. A genetically modified plant comprising the nucleic acid expression vector of claim 1.

7. The method of claim 2, wherein said plant is selected from the group consisting of a crop plant, a decorative plant, and a tree.

8. The method of claim 2, wherein said plant is a Solanaceae plant.

9. The method of claim 2, wherein said plant is selected from the group consisting of a tomato plant, a potato plant, an eggplant plant, a banana plant, a sweet pepper plant, an olive plant, an apple plant, a pear plant, a firethorn plant, a flowering crabapple plant, a hawthorn plant, a *cotoneaster* plant, a quince plant, a mountain ash plant, an *arabidopsis* plant, a *geranium*, a ginger plant, a tobacco plant and a *eucalyptus* plant.

* * * * *

SEQUENCE LISTING

```
<160> NUMBER OF SEQ ID NOS: 100

<210> SEQ ID NO 1
<211> LENGTH: 357
<212> TYPE: DNA
<213> ORGANISM: Artificial sequence
<220> FEATURE:
<223> OTHER INFORMATION: Nucleic acid sequence of T3SS-IBE 1

<400> SEQUENCE: 1

atggagagct tccgtcgatt ctctttgctc tcctttatag ccctactggc ttactttgct      60

tttcttgcct ccgctgaaca tcatgttcac caatttgtga tcactcccat ggctggagtt     120

cctaagccta atactacaaa cacgacatca acgacctcaa ccttccagtc tttcgctaac     180

ggtgtcgatg atgcagcttc aaggactggt ttccaggcac aatatcaagc aatcaccgcc     240

cagggacaac aagatatgtt agacgctgcg aagatgcaga acgctttgaa tcgaacacaa     300

atgcttgcca agctgatgga agctggccca aaagcagcga aagaccttat ttcctaa        357


<210> SEQ ID NO 2
<211> LENGTH: 118
<212> TYPE: PRT
<213> ORGANISM: Artificial sequence
<220> FEATURE:
<223> OTHER INFORMATION: Amino acid sequence of T3SS-IBE 1

<400> SEQUENCE: 2

Met Glu Ser Phe Arg Arg Phe Ser Leu Leu Ser Phe Ile Ala Leu Leu
1               5                   10                  15

Ala Tyr Phe Ala Phe Leu Ala Ser Ala Glu His His Val His Gln Phe
            20                  25                  30

Val Ile Thr Pro Met Ala Gly Val Pro Lys Pro Asn Thr Thr Asn Thr
        35                  40                  45

Thr Ser Thr Thr Ser Thr Phe Gln Ser Phe Ala Asn Gly Val Asp Asp
    50                  55                  60

Ala Ala Ser Arg Thr Gly Phe Gln Ala Gln Tyr Gln Ala Ile Thr Ala
65                  70                  75                  80
```

Gln Gly Gln Gln Asp Met Leu Asp Ala Ala Lys Met Gln Asn Ala Leu
85 90 95

Asn Arg Thr Gln Met Leu Ala Lys Leu Met Glu Ala Gly Pro Lys Ala
100 105 110

Ala Lys Asp Leu Ile Ser
115

<210> SEQ ID NO 3
<211> LENGTH: 288
<212> TYPE: DNA
<213> ORGANISM: Artificial sequence
<220> FEATURE:
<223> OTHER INFORMATION: Nucleic acid sequence of T3SS-IBE 2

<400> SEQUENCE: 3
atgggactcc agcaaggact tgtcacatgg ttcgttggtg tactcttcct ctctacccta 60
ttgcttagca atgctgacgt ccatcactac gaatttttcg tccgtcctaa cggagttgat 120
gatgctgcct caaggactgg gtttcaagca caatatcaag cgattactgc ccaaggacag 180
caagatatgc ttgacgctgc aaagatgcaa aatgcgctga atagaaccca gatgttggcc 240
aaacttatgg aggctggccc gaaggctgcc aaggatctga tcagttaa 288

<210> SEQ ID NO 4
<211> LENGTH: 95
<212> TYPE: PRT
<213> ORGANISM: Artificial sequence
<220> FEATURE:
<223> OTHER INFORMATION: Amino acid sequence of T3SS-IBE 2

<400> SEQUENCE: 4

Met Gly Leu Gln Gln Gly Leu Val Thr Trp Phe Val Gly Val Leu Phe
1 5 10 15

Leu Ser Thr Leu Leu Leu Ser Asn Ala Asp Val His His Tyr Glu Phe
20 25 30

Phe Val Arg Pro Asn Gly Val Asp Asp Ala Ala Ser Arg Thr Gly Phe
35 40 45

Gln Ala Gln Tyr Gln Ala Ile Thr Ala Gln Gly Gln Gln Asp Met Leu
50 55 60

Asp Ala Ala Lys Met Gln Asn Ala Leu Asn Arg Thr Gln Met Leu Ala
65 70 75 80

Lys Leu Met Glu Ala Gly Pro Lys Ala Ala Lys Asp Leu Ile Ser
85 90 95

<210> SEQ ID NO 5
<211> LENGTH: 381
<212> TYPE: DNA
<213> ORGANISM: Artificial sequence
<220> FEATURE:
<223> OTHER INFORMATION: Nucleic acid sequence of T3SS-IBE 3

<400> SEQUENCE: 5
atggagagct tccgtcgatt ctctttgctc tcctttattg ccctgcttgc ttactttgct 60
ttccttgctt ccgcgatggc tggagttcca aaacccaaca ctacgaatac cacaagcact 120
acttcgacct tccaaagtgt gaccgtcggc aatgatgatt ggaccctgtc ttcactctcg 180
gaaacctttg actcctttgc taacggtgtt gatgacgcag ctagccgaac aggcttccaa 240
gcacagtatc aggctataac ggcacaaggg cagcaagata tgttggatgc cgccaagatg 300
cagaatgccc tcaacagaac tcaaatgcta gccaaactca tggaggccgg acctaaggct 360

```
gcaaaggacc ttatctctta a                                           381


<210> SEQ ID NO 6
<211> LENGTH: 126
<212> TYPE: PRT
<213> ORGANISM: Artificial sequence
<220> FEATURE:
<223> OTHER INFORMATION: Amino acid sequence of T3SS-IBE 3

<400> SEQUENCE: 6

Met Glu Ser Phe Arg Arg Phe Ser Leu Leu Ser Phe Ile Ala Leu Leu
1               5                   10                  15

Ala Tyr Phe Ala Phe Leu Ala Ser Ala Met Ala Gly Val Pro Lys Pro
            20                  25                  30

Asn Thr Thr Asn Thr Thr Ser Thr Thr Ser Thr Phe Gln Ser Val Thr
        35                  40                  45

Val Gly Asn Asp Asp Trp Thr Leu Ser Ser Leu Ser Glu Thr Phe Asp
    50                  55                  60

Ser Phe Ala Asn Gly Val Asp Asp Ala Ala Ser Arg Thr Gly Phe Gln
65                  70                  75                  80

Ala Gln Tyr Gln Ala Ile Thr Ala Gln Gly Gln Gln Asp Met Leu Asp
                85                  90                  95

Ala Ala Lys Met Gln Asn Ala Leu Asn Arg Thr Gln Met Leu Ala Lys
            100                 105                 110

Leu Met Glu Ala Gly Pro Lys Ala Ala Lys Asp Leu Ile Ser
        115                 120                 125


<210> SEQ ID NO 7
<211> LENGTH: 387
<212> TYPE: DNA
<213> ORGANISM: Artificial sequence
<220> FEATURE:
<223> OTHER INFORMATION: Nucleic acid sequence of T3SS-IBE 4

<400> SEQUENCE: 7

atgggactcc agcaagggct tgtcacatgg ttcgttggag tccttttcct ctccaccttg      60

ttacttagca atgcgatggc tggtgttccc aaacctaaca ccacgaacac cactagcact     120

acttccacct ttcaaagttt cgcgaacggg gtagatgatg ctgcttcacg tacaggattt     180

caagcccaat accaggctat aacggcacaa ggtcagcaag atatgcttga cgctgccaag     240

atgcaaaatg ccctcaaccg cacacagatg cttgctaagc tgatggaagc cggccctaaa     300

gcagctaagg acttgatctc tggtggccag atgcttgcaa agctaatgga ggctggacca     360

aaagctgcaa aggacctgat tagctaa                                         387


<210> SEQ ID NO 8
<211> LENGTH: 128
<212> TYPE: PRT
<213> ORGANISM: Artificial sequence
<220> FEATURE:
<223> OTHER INFORMATION: Amino acid sequence of T3SS-IBE 4

<400> SEQUENCE: 8

Met Gly Leu Gln Gln Gly Leu Val Thr Trp Phe Val Gly Val Leu Phe
1               5                   10                  15

Leu Ser Thr Leu Leu Leu Ser Asn Ala Met Ala Gly Val Pro Lys Pro
            20                  25                  30

Asn Thr Thr Asn Thr Thr Ser Thr Thr Ser Thr Phe Gln Ser Phe Ala
        35                  40                  45
```

```
Asn Gly Val Asp Asp Ala Ala Ser Arg Thr Gly Phe Gln Ala Gln Tyr
    50                  55                  60

Gln Ala Ile Thr Ala Gln Gly Gln Gln Asp Met Leu Asp Ala Ala Lys
65                  70                  75                  80

Met Gln Asn Ala Leu Asn Arg Thr Gln Met Leu Ala Lys Leu Met Glu
                85                  90                  95

Ala Gly Pro Lys Ala Ala Lys Asp Leu Ile Ser Gly Gly Gln Met Leu
            100                 105                 110

Ala Lys Leu Met Glu Ala Gly Pro Lys Ala Ala Lys Asp Leu Ile Ser
        115                 120                 125


<210> SEQ ID NO 9
<211> LENGTH: 324
<212> TYPE: DNA
<213> ORGANISM: Artificial sequence
<220> FEATURE:
<223> OTHER INFORMATION: Nucleic acid sequence of T3SS-IBE 5

<400> SEQUENCE: 9

atggagagct tccgtcgatt ctccttgctc tctttcattg cgctcctggc ctactttgct     60

tttcttgctt cggcaatggc tggtgttcct aaaccgaaca ccacgaatac cacgagcact    120

acttcaacct ttcaatcctt tgcgaacggg gtagatgatg ctgctagtag gacaccattt    180

caagcccaat atcaggcgat aactgctcaa ggacagcaag atatgctaga cgccgccaag    240

atgcagaatg ccctcaaccg cacacagatg ttggcaaagc tgatggaagc aggacccaaa    300

gcagccaaag accttatctc ttaa                                           324


<210> SEQ ID NO 10
<211> LENGTH: 107
<212> TYPE: PRT
<213> ORGANISM: Artificial sequence
<220> FEATURE:
<223> OTHER INFORMATION: Amino acid sequence of T3SS-IBE 5

<400> SEQUENCE: 10

Met Glu Ser Phe Arg Arg Phe Ser Leu Leu Ser Phe Ile Ala Leu Leu
1               5                   10                  15

Ala Tyr Phe Ala Phe Leu Ala Ser Ala Met Ala Gly Val Pro Lys Pro
            20                  25                  30

Asn Thr Thr Asn Thr Thr Ser Thr Thr Ser Thr Phe Gln Ser Phe Ala
        35                  40                  45

Asn Gly Val Asp Asp Ala Ala Ser Arg Thr Pro Phe Gln Ala Gln Tyr
    50                  55                  60

Gln Ala Ile Thr Ala Gln Gly Gln Gln Asp Met Leu Asp Ala Ala Lys
65                  70                  75                  80

Met Gln Asn Ala Leu Asn Arg Thr Gln Met Leu Ala Lys Leu Met Glu
                85                  90                  95

Ala Gly Pro Lys Ala Ala Lys Asp Leu Ile Ser
            100                 105


<210> SEQ ID NO 11
<211> LENGTH: 324
<212> TYPE: DNA
<213> ORGANISM: Artificial sequence
<220> FEATURE:
<223> OTHER INFORMATION: Nucleic acid sequence of T3SS-IBE 6

<400> SEQUENCE: 11
```

```
atgggactgc aacaaggcct cgtaacctgg tttgtcggag tcttgttcct gtctaccttg      60

ctccttagca atgctatggc tggggttccg aaacctaaca ccactaacac cacaagcact     120

acttccactt tccaatcgtt cgcaaacggt gttgatgatg ctgcttcaag gacaggcttt     180

caagcccaat accaggctat aacggctcaa ggtcagcagg atatgctcga cgcagctaaa     240

atgcagaatg ccctaaaccg cacacagatg ctggctaagc tcatggaggc accacccaaa     300

gctgcgaaag acctaatctc ttaa                                            324


<210> SEQ ID NO 12
<211> LENGTH: 107
<212> TYPE: PRT
<213> ORGANISM: Artificial sequence
<220> FEATURE:
<223> OTHER INFORMATION: Amino acid sequence of T3SS-IBE 6

<400> SEQUENCE: 12

Met Gly Leu Gln Gln Gly Leu Val Thr Trp Phe Val Gly Val Leu Phe
1               5                   10                  15

Leu Ser Thr Leu Leu Leu Ser Asn Ala Met Ala Gly Val Pro Lys Pro
            20                  25                  30

Asn Thr Thr Asn Thr Thr Ser Thr Thr Ser Thr Phe Gln Ser Phe Ala
        35                  40                  45

Asn Gly Val Asp Asp Ala Ala Ser Arg Thr Gly Phe Gln Ala Gln Tyr
    50                  55                  60

Gln Ala Ile Thr Ala Gln Gly Gln Gln Asp Met Leu Asp Ala Ala Lys
65                  70                  75                  80

Met Gln Asn Ala Leu Asn Arg Thr Gln Met Leu Ala Lys Leu Met Glu
                85                  90                  95

Ala Pro Pro Lys Ala Ala Lys Asp Leu Ile Ser
            100                 105


<210> SEQ ID NO 13
<211> LENGTH: 249
<212> TYPE: DNA
<213> ORGANISM: Ralstonia solanacearum

<400> SEQUENCE: 13

atggcaggcg ttccgaaacc caacacgacg aacacgacga gcaccacctc cacgttccaa      60

tccttcgcca acggcgtcga cgacgctgcc tcccgtacgg gcttccaggc tcaataccaa     120

gccatcaccg ccgaaggcca gcaagacatg ctggacgcgg ccaagatgca gaacgccctg     180

aaccgcaccc agatgctggc caagctgatg gaagccggcc cgaaggcggc gaaggacctg     240

atcagctaa                                                             249


<210> SEQ ID NO 14
<211> LENGTH: 82
<212> TYPE: PRT
<213> ORGANISM: Ralstonia solanacearum

<400> SEQUENCE: 14

Met Ala Gly Val Pro Lys Pro Asn Thr Thr Asn Thr Thr Ser Thr Thr
1               5                   10                  15

Ser Thr Phe Gln Ser Phe Ala Asn Gly Val Asp Asp Ala Ala Ser Arg
            20                  25                  30

Thr Gly Phe Gln Ala Gln Tyr Gln Ala Ile Thr Ala Glu Gly Gln Gln
        35                  40                  45

Asp Met Leu Asp Ala Ala Lys Met Gln Asn Ala Leu Asn Arg Thr Gln
```

```
    50                  55                  60

Met Leu Ala Lys Leu Met Glu Ala Gly Pro Lys Ala Ala Lys Asp Leu
65                  70                  75                  80

Ile Ser


<210> SEQ ID NO 15
<211> LENGTH: 83
<212> TYPE: PRT
<213> ORGANISM: Shigella flexneri

<400> SEQUENCE: 15

Met Ser Val Thr Val Pro Asn Asp Asp Trp Thr Leu Ser Ser Leu Ser
1               5                   10                  15

Glu Thr Phe Asp Asp Gly Thr Gln Thr Leu Gln Gly Glu Leu Thr Leu
            20                  25                  30

Ala Leu Asp Lys Leu Ala Lys Asn Pro Ser Asn Pro Gln Leu Leu Ala
        35                  40                  45

Glu Tyr Gln Ser Lys Leu Ser Glu Tyr Thr Leu Tyr Arg Asn Ala Gln
    50                  55                  60

Ser Asn Thr Val Lys Val Ile Lys Asp Val Asp Ala Ala Ile Ile Gln
65                  70                  75                  80

Asn Phe Arg


<210> SEQ ID NO 16
<211> LENGTH: 25
<212> TYPE: PRT
<213> ORGANISM: Artificial sequence
<220> FEATURE:
<223> OTHER INFORMATION: Secretion leader peptide derived from
      Arabidopsis thaliana Laccase (UniProt no: Q56YT0)

<400> SEQUENCE: 16

Met Glu Ser Phe Arg Arg Phe Ser Leu Leu Ser Phe Ile Ala Leu Leu
1               5                   10                  15

Ala Tyr Phe Ala Phe Leu Ala Ser Ala
            20                  25


<210> SEQ ID NO 17
<211> LENGTH: 25
<212> TYPE: PRT
<213> ORGANISM: Artificial sequence
<220> FEATURE:
<223> OTHER INFORMATION: Secretion leader peptide derived from Gossypium
      arboreum Laccase (UniProt no: Q6TDS6)

<400> SEQUENCE: 17

Met Gly Leu Gln Gln Gly Leu Val Thr Trp Phe Val Gly Val Leu Phe
1               5                   10                  15

Leu Ser Thr Leu Leu Leu Ser Asn Ala
            20                  25


<210> SEQ ID NO 18
<211> LENGTH: 342
<212> TYPE: DNA
<213> ORGANISM: Pseudomonas syringae pv. tomato str. DC3000

<400> SEQUENCE: 18

atggtcgcat ttgcaggatt aacctccaaa ctcaccaacc ttggtaacag cgccgttggc      60

ggtgtcggcg gcgcattgca gggtgtcaac acggttgctt ccaacgccac tcttcagaaa     120

aacattcttt tgggcaccgg cgacagcctg tcggttgatg cacaagccaa ggccagtaaa     180
```

gagtccgacg ccaacggcgc gaagctgatc gcgatgcagg cccaggaaac aatgaagaag 240
cagaccatgg acgtgctcaa cgccatccag gccggcaaag aagactctac caacaagaag 300
atcagtgcca cagcgacgaa cgctaaaggt atcagttact aa 342

<210> SEQ ID NO 19
<211> LENGTH: 113
<212> TYPE: PRT
<213> ORGANISM: Pseudomonas syringae pv. tomato str. DC3000

<400> SEQUENCE: 19

Met Val Ala Phe Ala Gly Leu Thr Ser Lys Leu Thr Asn Leu Gly Asn
1 5 10 15

Ser Ala Val Gly Gly Val Gly Gly Ala Leu Gln Gly Val Asn Thr Val
20 25 30

Ala Ser Asn Ala Thr Leu Gln Lys Asn Ile Leu Leu Gly Thr Gly Asp
35 40 45

Ser Leu Ser Val Asp Ala Gln Ala Lys Ala Ser Lys Glu Ser Asp Ala
50 55 60

Asn Gly Ala Lys Leu Ile Ala Met Gln Ala Gln Glu Thr Met Lys Lys
65 70 75 80

Gln Thr Met Asp Val Leu Asn Ala Ile Gln Ala Gly Lys Glu Asp Ser
85 90 95

Thr Asn Lys Lys Ile Ser Ala Thr Ala Thr Asn Ala Lys Gly Ile Ser
100 105 110

Tyr

<210> SEQ ID NO 20
<211> LENGTH: 5
<212> TYPE: PRT
<213> ORGANISM: Artificial sequence
<220> FEATURE:
<223> OTHER INFORMATION: Exemplary pentapeptide insertions which may be inserted into the peptides of the present invention

<400> SEQUENCE: 20

Met Arg Pro His Ser
1 5

<210> SEQ ID NO 21
<211> LENGTH: 5
<212> TYPE: PRT
<213> ORGANISM: Artificial sequence
<220> FEATURE:
<223> OTHER INFORMATION: Exemplary pentapeptide insertions which may be inserted into the peptides of the present invention

<400> SEQUENCE: 21

Gly Ala Ala Ala Ile
1 5

<210> SEQ ID NO 22
<211> LENGTH: 5
<212> TYPE: PRT
<213> ORGANISM: Artificial sequence
<220> FEATURE:
<223> OTHER INFORMATION: Exemplary pentapeptide insertions which may be inserted into the peptides of the present invention

<400> SEQUENCE: 22

Cys Gly Arg Ile Gly
1 5

<210> SEQ ID NO 23
<211> LENGTH: 5
<212> TYPE: PRT
<213> ORGANISM: Artificial sequence
<220> FEATURE:
<223> OTHER INFORMATION: Exemplary pentapeptide insertions which may be inserted into the peptides of the present invention

<400> SEQUENCE: 23

Cys Gly Arg Ser Ala
1               5

<210> SEQ ID NO 24
<211> LENGTH: 5
<212> TYPE: PRT
<213> ORGANISM: Artificial sequence
<220> FEATURE:
<223> OTHER INFORMATION: Exemplary pentapeptide insertions which may be inserted into the peptides of the present invention

<400> SEQUENCE: 24

Gly Ala Ala Ala Val
1               5

<210> SEQ ID NO 25
<211> LENGTH: 5
<212> TYPE: PRT
<213> ORGANISM: Artificial sequence
<220> FEATURE:
<223> OTHER INFORMATION: Exemplary pentapeptide insertions which may be inserted into the peptides of the present invention

<400> SEQUENCE: 25

Cys Gly Arg Ile Gly
1               5

<210> SEQ ID NO 26
<211> LENGTH: 5
<212> TYPE: PRT
<213> ORGANISM: Artificial sequence
<220> FEATURE:
<223> OTHER INFORMATION: Exemplary pentapeptide insertions which may be inserted into the peptides of the present invention

<400> SEQUENCE: 26

Cys Gly Arg Ser Gly
1               5

<210> SEQ ID NO 27
<211> LENGTH: 5
<212> TYPE: PRT
<213> ORGANISM: Artificial sequence
<220> FEATURE:
<223> OTHER INFORMATION: Exemplary pentapeptide insertions which may be inserted into the peptides of the present invention

<400> SEQUENCE: 27

Val Arg Pro Gln Gln
1               5

<210> SEQ ID NO 28
<211> LENGTH: 5
<212> TYPE: PRT
<213> ORGANISM: Artificial sequence
<220> FEATURE:
<223> OTHER INFORMATION: Exemplary pentapeptide insertions which may be inserted into the peptides of the present invention

<400> SEQUENCE: 28

Gly Ala Ala Ala Gln
1 5

<210> SEQ ID NO 29
<211> LENGTH: 5
<212> TYPE: PRT
<213> ORGANISM: Artificial sequence
<220> FEATURE:
<223> OTHER INFORMATION: Exemplary pentapeptide insertions which may be inserted into the peptides of the present invention

<400> SEQUENCE: 29

Asn Ala Ala Ala Val
1 5

<210> SEQ ID NO 30
<211> LENGTH: 5
<212> TYPE: PRT
<213> ORGANISM: Artificial sequence
<220> FEATURE:
<223> OTHER INFORMATION: Exemplary pentapeptide insertions which may be inserted into the peptides of the present invention

<400> SEQUENCE: 30

Thr Ala Ala Ala Asn
1 5

<210> SEQ ID NO 31
<211> LENGTH: 5
<212> TYPE: PRT
<213> ORGANISM: Artificial sequence
<220> FEATURE:
<223> OTHER INFORMATION: Exemplary pentapeptide insertions which may be inserted into the peptides of the present invention

<400> SEQUENCE: 31

Met Arg Pro His Ser
1 5

<210> SEQ ID NO 32
<211> LENGTH: 5
<212> TYPE: PRT
<213> ORGANISM: Artificial sequence
<220> FEATURE:
<223> OTHER INFORMATION: Exemplary pentapeptide insertions which may be inserted into the peptides of the present invention

<400> SEQUENCE: 32

Thr Ala Ala Ala Ala
1 5

<210> SEQ ID NO 33
<211> LENGTH: 5
<212> TYPE: PRT
<213> ORGANISM: Artificial sequence
<220> FEATURE:
<223> OTHER INFORMATION: Exemplary pentapeptide insertions which may be inserted into the peptides of the present invention

<400> SEQUENCE: 33

Leu Arg Pro His Thr
1 5

<210> SEQ ID NO 34
<211> LENGTH: 5

<212> TYPE: PRT
<213> ORGANISM: Artificial sequence
<220> FEATURE:
<223> OTHER INFORMATION: Exemplary pentapeptide insertions which may be inserted into the peptides of the present invention

<400> SEQUENCE: 34

Cys Gly Arg Thr Phe
1 5

<210> SEQ ID NO 35
<211> LENGTH: 5
<212> TYPE: PRT
<213> ORGANISM: Artificial sequence
<220> FEATURE:
<223> OTHER INFORMATION: Exemplary pentapeptide insertions which may be inserted into the peptides of the present invention

<400> SEQUENCE: 35

Val Arg Pro His Leu
1 5

<210> SEQ ID NO 36
<211> LENGTH: 5
<212> TYPE: PRT
<213> ORGANISM: Artificial sequence
<220> FEATURE:
<223> OTHER INFORMATION: Exemplary pentapeptide insertions which may be inserted into the peptides of the present invention

<400> SEQUENCE: 36

Met Arg Pro Gln Gly
1 5

<210> SEQ ID NO 37
<211> LENGTH: 5
<212> TYPE: PRT
<213> ORGANISM: Artificial sequence
<220> FEATURE:
<223> OTHER INFORMATION: Exemplary pentapeptide insertions which may be inserted into the peptides of the present invention

<400> SEQUENCE: 37

Cys Gly Arg Thr Gly
1 5

<210> SEQ ID NO 38
<211> LENGTH: 5
<212> TYPE: PRT
<213> ORGANISM: Artificial sequence
<220> FEATURE:
<223> OTHER INFORMATION: Exemplary pentapeptide insertions which may be inserted into the peptides of the present invention

<400> SEQUENCE: 38

Cys Gly Arg Ser Asp
1 5

<210> SEQ ID NO 39
<211> LENGTH: 5
<212> TYPE: PRT
<213> ORGANISM: Artificial sequence
<220> FEATURE:
<223> OTHER INFORMATION: Exemplary pentapeptide insertions which may be inserted into the peptides of the present invention

<400> SEQUENCE: 39

Val Arg Pro Gln Ser 1 5

<210> SEQ ID NO 40
<211> LENGTH: 5
<212> TYPE: PRT
<213> ORGANISM: Artificial sequence
<220> FEATURE:
<223> OTHER INFORMATION: Exemplary pentapeptide insertions which may be inserted into the peptides of the present invention

<400> SEQUENCE: 40

Val Ala Ala Ala Ser
1 5

<210> SEQ ID NO 41
<211> LENGTH: 5
<212> TYPE: PRT
<213> ORGANISM: Artificial sequence
<220> FEATURE:
<223> OTHER INFORMATION: Exemplary pentapeptide insertions which may be inserted into the peptides of the present invention

<400> SEQUENCE: 41

Asp Ala Ala Ala Val
1 5

<210> SEQ ID NO 42
<211> LENGTH: 5
<212> TYPE: PRT
<213> ORGANISM: Artificial sequence
<220> FEATURE:
<223> OTHER INFORMATION: Exemplary pentapeptide insertions which may be inserted into the peptides of the present invention

<400> SEQUENCE: 42

Asn Ala Ala Ala Ala
1 5

<210> SEQ ID NO 43
<211> LENGTH: 5
<212> TYPE: PRT
<213> ORGANISM: Artificial sequence
<220> FEATURE:
<223> OTHER INFORMATION: Exemplary pentapeptide insertions which may be inserted into the peptides of the present invention

<400> SEQUENCE: 43

Cys Gly Arg Thr Ser
1 5

<210> SEQ ID NO 44
<211> LENGTH: 5
<212> TYPE: PRT
<213> ORGANISM: Artificial sequence
<220> FEATURE:
<223> OTHER INFORMATION: Exemplary pentapeptide insertions which may be inserted into the peptides of the present invention

<400> SEQUENCE: 44

Met Arg Pro His Ala
1 5

<210> SEQ ID NO 45
<211> LENGTH: 5
<212> TYPE: PRT
<213> ORGANISM: Artificial sequence
<220> FEATURE:
<223> OTHER INFORMATION: Exemplary pentapeptide insertions which may be inserted into the peptides of the present invention

<400> SEQUENCE: 45

Val Arg Pro Gln Gln
1 5

<210> SEQ ID NO 46
<211> LENGTH: 5
<212> TYPE: PRT
<213> ORGANISM: Artificial sequence
<220> FEATURE:
<223> OTHER INFORMATION: Exemplary pentapeptide insertions which may be inserted into the peptides of the present invention

<400> SEQUENCE: 46

Cys Gly Arg Thr Gln
1 5

<210> SEQ ID NO 47
<211> LENGTH: 5
<212> TYPE: PRT
<213> ORGANISM: Artificial sequence
<220> FEATURE:
<223> OTHER INFORMATION: Exemplary pentapeptide insertions which may be inserted into the peptides of the present invention

<400> SEQUENCE: 47

Cys Gly Arg Lys Glu
1 5

<210> SEQ ID NO 48
<211> LENGTH: 5
<212> TYPE: PRT
<213> ORGANISM: Artificial sequence
<220> FEATURE:
<223> OTHER INFORMATION: Exemplary pentapeptide insertions which may be inserted into the peptides of the present invention

<400> SEQUENCE: 48

Asn Ala Ala Ala Met
1 5

<210> SEQ ID NO 49
<211> LENGTH: 5
<212> TYPE: PRT
<213> ORGANISM: Artificial sequence
<220> FEATURE:
<223> OTHER INFORMATION: Exemplary pentapeptide insertions which may be inserted into the peptides of the present invention

<400> SEQUENCE: 49

Asp Ala Ala Ala Met
1 5

<210> SEQ ID NO 50
<211> LENGTH: 5
<212> TYPE: PRT
<213> ORGANISM: Artificial sequence
<220> FEATURE:
<223> OTHER INFORMATION: Exemplary pentapeptide insertions which may be inserted into the peptides of the present invention

<400> SEQUENCE: 50

Ala Ala Ala Ala Asn
1 5

<210> SEQ ID NO 51

<211> LENGTH: 5
<212> TYPE: PRT
<213> ORGANISM: Artificial sequence
<220> FEATURE:
<223> OTHER INFORMATION: Exemplary pentapeptide insertions which may be inserted into the peptides of the present invention

<400> SEQUENCE: 51

Val Arg Pro His Gln
1 5

<210> SEQ ID NO 52
<211> LENGTH: 5
<212> TYPE: PRT
<213> ORGANISM: Artificial sequence
<220> FEATURE:
<223> OTHER INFORMATION: Exemplary pentapeptide insertions which may be inserted into the peptides of the present invention

<400> SEQUENCE: 52

Ala Ala Ala Ala Gly
1 5

<210> SEQ ID NO 53
<211> LENGTH: 5
<212> TYPE: PRT
<213> ORGANISM: Artificial sequence
<220> FEATURE:
<223> OTHER INFORMATION: Exemplary pentapeptide insertions which may be inserted into the peptides of the present invention

<400> SEQUENCE: 53

Met Arg Pro His Ser
1 5

<210> SEQ ID NO 54
<211> LENGTH: 5
<212> TYPE: PRT
<213> ORGANISM: Artificial sequence
<220> FEATURE:
<223> OTHER INFORMATION: Exemplary pentapeptide insertions which may be inserted into the peptides of the present invention

<400> SEQUENCE: 54

Thr Ala Ala Ala Ser
1 5

<210> SEQ ID NO 55
<211> LENGTH: 5
<212> TYPE: PRT
<213> ORGANISM: Artificial sequence
<220> FEATURE:
<223> OTHER INFORMATION: Exemplary pentapeptide insertions which may be inserted into the peptides of the present invention

<400> SEQUENCE: 55

Cys Gly Arg Thr Asn
1 5

<210> SEQ ID NO 56
<211> LENGTH: 5
<212> TYPE: PRT
<213> ORGANISM: Artificial sequence
<220> FEATURE:
<223> OTHER INFORMATION: Exemplary pentapeptide insertions which may be inserted into the peptides of the present invention

<400> SEQUENCE: 56

```
Ala Ala Ala Ala Thr
1               5


<210> SEQ ID NO 57
<211> LENGTH: 5
<212> TYPE: PRT
<213> ORGANISM: Artificial sequence
<220> FEATURE:
<223> OTHER INFORMATION: Exemplary pentapeptide insertions which may be
      inserted into the peptides of the present invention

<400> SEQUENCE: 57

Ala Ala Ala Ala Thr
1               5


<210> SEQ ID NO 58
<211> LENGTH: 5
<212> TYPE: PRT
<213> ORGANISM: Artificial sequence
<220> FEATURE:
<223> OTHER INFORMATION: Exemplary pentapeptide insertions which may be
      inserted into the peptides of the present invention

<400> SEQUENCE: 58

Cys Gly Arg Thr Ala
1               5


<210> SEQ ID NO 59
<211> LENGTH: 5
<212> TYPE: PRT
<213> ORGANISM: Artificial sequence
<220> FEATURE:
<223> OTHER INFORMATION: Exemplary pentapeptide insertions which may be
      inserted into the peptides of the present invention

<400> SEQUENCE: 59

Ala Ala Ala Ala Thr
1               5


<210> SEQ ID NO 60
<211> LENGTH: 5
<212> TYPE: PRT
<213> ORGANISM: Artificial sequence
<220> FEATURE:
<223> OTHER INFORMATION: Exemplary pentapeptide insertions which may be
      inserted into the peptides of the present invention

<400> SEQUENCE: 60

Met Arg Pro Gln Thr
1               5


<210> SEQ ID NO 61
<211> LENGTH: 5
<212> TYPE: PRT
<213> ORGANISM: Artificial sequence
<220> FEATURE:
<223> OTHER INFORMATION: Exemplary pentapeptide insertions which may be
      inserted into the peptides of the present invention

<400> SEQUENCE: 61

Ala Ala Ala Ala Asn
1               5


<210> SEQ ID NO 62
<211> LENGTH: 5
<212> TYPE: PRT
<213> ORGANISM: Artificial sequence
<220> FEATURE:
```

<223> OTHER INFORMATION: Exemplary pentapeptide insertions which may be inserted into the peptides of the present invention

<400> SEQUENCE: 62

Cys Gly Arg Asn Ala
1 5

<210> SEQ ID NO 63
<211> LENGTH: 5
<212> TYPE: PRT
<213> ORGANISM: Artificial sequence
<220> FEATURE:
<223> OTHER INFORMATION: Exemplary pentapeptide insertions which may be inserted into the peptides of the present invention

<400> SEQUENCE: 63

Cys Gly Arg Ile Ser
1 5

<210> SEQ ID NO 64
<211> LENGTH: 5
<212> TYPE: PRT
<213> ORGANISM: Artificial sequence
<220> FEATURE:
<223> OTHER INFORMATION: Exemplary pentapeptide insertions which may be inserted into the peptides of the present invention

<400> SEQUENCE: 64

Tyr Ala Ala Ala Ser
1 5

<210> SEQ ID NO 65
<211> LENGTH: 5
<212> TYPE: PRT
<213> ORGANISM: Artificial sequence
<220> FEATURE:
<223> OTHER INFORMATION: Exemplary pentapeptide insertions which may be inserted into the peptides of the present invention

<400> SEQUENCE: 65

Cys Gly Arg Ser Tyr
1 5

<210> SEQ ID NO 66
<211> LENGTH: 2181
<212> TYPE: DNA
<213> ORGANISM: Ralstonia solanacearum

<400> SEQUENCE: 66
atgagtacca acatctctag cgcagcgagc ccgaccttgc cgttagccgg gccgggcgtc 60
aacgggccag ccgagggcaa atccgatatg ccgggttcgc tgttcttcca gttcgaccac 120
tccacgggca gcacccgtcc ggacctgccg accgacctgt tcttcagctt cggcgattcc 180
atctcgcgtg cggtgcagga cgcgtcgaat caatcgccgg agcaggctcc ggccgccgac 240
ccggctccgg ccagcccgga cggccaatcc tgccagccga gccagcccgc caccccgccc 300
gtcggcagcg acgtgacctg gaacggcggt acgctcaacg acacccagtt gcagatcatc 360
ggcatcctga acctgcacaa ggacaagggc gatatcagct gggacaagct gcaggacaag 420
atcaacgacc ccgacacgcc gcccgacctg aagtgggcac tgcaggcgct gtcgcaggat 480
ttcaacctgt tccaggcgat cggctcgcag ggcgacggcc gtttcggcgg caagatcaag 540
ggcaaggatc tggccgaatt cgccaagagc cattcgcagg tcctgacgtg gaacagcggc 600
acgctcaacg acagccagct ggagatcatg tccatcctgg cccgccacaa ggacaagatg 660

```
ccggtcgact ggagctcgat ccaggacaag atcaatgatc ccagcacgcc gtccgacctg    720

aaggccgcgc tgcaggcgct ggccaacgat ccggcgctgt tcttcgccat cggctcgcag    780

ggcgacggca actgcaaggg caagatcaag gccggcgacg tgagcaagtt cgcggacaac    840

cacccgcagg tggaggaata caaccgcaag aaggccgaag gctatgtgaa gaactacatc    900

ccgtccgacg cgaagccggg cgacaagcct tcggccatga cgcagaacga tgcgctgcgc    960

gagctgtacc gctactccga ctacctgccg aagaagctgg acatggaagc cttccagcgc   1020

atcgtcgacg gcgactcgga cgtcaagaag gcgccgccgc aggtgatcgc cgcggccgag   1080

tatttcctgc agaaccgcaa cgagtgggcg agcctgaaca agatggacga ccccgacaag   1140

cgggtgggca agtcggactt cctgcagcgc gccgcctcgg ccgtgcacct gagcaaggaa   1200

gatctgcaga ccgtgtcgac catcaacagc aatctcgacg tgttcttcaa ggacggccag   1260

aagatcaccc gcgaccggct ggcggcgatg tcgcaggacg agagcctgtc tccggccgtg   1320

cgcaacgcgg ccaagcagct gctgcaggat ccgctgctgt acgggctgat caacaacgcg   1380

aactcgggct acaagacgaa gaacggcttc ttcagcttcg gcggcccgac ggtggattcc   1440

ggcgtgatcg gcaagaagga cttcgagaag ttcatgtcga gcatgacgga cgccaacaag   1500

acggtccagg cgcgcaagac gcatccggcg aactcggagg ccagcaagag cgccgttgcc   1560

gacatgggca tgggcatgga agaccagccc gacatcaagg cggtcaagaa gagcggcggc   1620

gcgctgaaga aggccatgga caagatcctc accatctact cgaaggtgat ggacatcgcg   1680

tcgcaggtcg ttggtgcgct gggcgtgatt ccggggctgg gtgaaatcgc ggacgcgctg   1740

tcgatgggga tggccgccgg ggcctcggcg gccaaggtgc tgtcgaccct gctgaacggg   1800

ggcagcctca agaaggcgct ggcggaggcg ggcatcaacc tggcctccgc tgcgctgggg   1860

gccgtcgccg gaccggaggc gcgggtggcg ctcaagaacg gcctgaccaa gatgctcgtg   1920

gagaaggtgg ccaacaccgg catcgatctg gcggtcgaca aggcgaagtc gttcgtggat   1980

ggttacctgc aggacctgaa gggccgcctg caagccaccg cggccaacgc cgccaacacg   2040

gtcaacacca gcgtcaactg ggtgtcggac aagacgaagg acttcctgga gaacccggtg   2100

cagaacctga cgccccgtgt gaatatcccc ggcatcaccc cgtatcagcc gggctatccg   2160

atggtggcgg cggcggcctg a                                             2181
```

```
<210> SEQ ID NO 67
<211> LENGTH: 726
<212> TYPE: PRT
<213> ORGANISM: Ralstonia solanacearum

<400> SEQUENCE: 67

Met Ser Thr Asn Ile Ser Ser Ala Ala Ser Pro Thr Leu Pro Leu Ala
1               5                   10                  15

Gly Pro Gly Val Asn Gly Pro Ala Glu Gly Lys Ser Asp Met Pro Gly
            20                  25                  30

Ser Leu Phe Phe Gln Phe Asp His Ser Thr Gly Ser Thr Arg Pro Asp
        35                  40                  45

Leu Pro Thr Asp Leu Phe Phe Ser Phe Gly Asp Ser Ile Ser Arg Ala
    50                  55                  60

Val Gln Asp Ala Ser Asn Gln Ser Pro Glu Gln Ala Pro Ala Ala Asp
65                  70                  75                  80

Pro Ala Pro Ala Ser Pro Asp Gly Gln Ser Cys Gln Pro Ser Gln Pro
                85                  90                  95
```

-continued

```
Ala Thr Pro Pro Val Gly Ser Asp Val Thr Trp Asn Gly Gly Thr Leu
            100                 105                 110

Asn Asp Thr Gln Leu Gln Ile Ile Gly Ile Leu Asn Leu His Lys Asp
        115                 120                 125

Lys Gly Asp Ile Ser Trp Asp Lys Leu Gln Asp Lys Ile Asn Asp Pro
    130                 135                 140

Asp Thr Pro Pro Asp Leu Lys Trp Ala Leu Gln Ala Leu Ser Gln Asp
145                 150                 155                 160

Phe Asn Leu Phe Gln Ala Ile Gly Ser Gln Gly Asp Gly Arg Phe Gly
                165                 170                 175

Gly Lys Ile Lys Gly Lys Asp Leu Ala Glu Phe Ala Lys Ser His Ser
            180                 185                 190

Gln Val Leu Thr Trp Asn Ser Gly Thr Leu Asn Asp Ser Gln Leu Glu
        195                 200                 205

Ile Met Ser Ile Leu Ala Arg His Lys Asp Lys Met Pro Val Asp Trp
    210                 215                 220

Ser Ser Ile Gln Asp Lys Ile Asn Asp Pro Ser Thr Pro Ser Asp Leu
225                 230                 235                 240

Lys Ala Ala Leu Gln Ala Leu Ala Asn Asp Pro Ala Leu Phe Phe Ala
                245                 250                 255

Ile Gly Ser Gln Gly Asp Gly Asn Cys Lys Gly Lys Ile Lys Ala Gly
            260                 265                 270

Asp Val Ser Lys Phe Ala Asp Asn His Pro Gln Val Glu Glu Tyr Asn
        275                 280                 285

Arg Lys Lys Ala Glu Gly Tyr Val Lys Asn Tyr Ile Pro Ser Asp Ala
    290                 295                 300

Lys Pro Gly Asp Lys Pro Ser Ala Met Thr Gln Asn Asp Ala Leu Arg
305                 310                 315                 320

Glu Leu Tyr Arg Tyr Ser Asp Tyr Leu Pro Lys Lys Leu Asp Met Glu
                325                 330                 335

Ala Phe Gln Arg Ile Val Asp Gly Asp Ser Asp Val Lys Lys Ala Pro
            340                 345                 350

Pro Gln Val Ile Ala Ala Ala Glu Tyr Phe Leu Gln Asn Arg Asn Glu
        355                 360                 365

Trp Ala Ser Leu Asn Lys Met Asp Asp Pro Asp Lys Arg Val Gly Lys
    370                 375                 380

Ser Asp Phe Leu Gln Arg Ala Ala Ser Ala Val His Leu Ser Lys Glu
385                 390                 395                 400

Asp Leu Gln Thr Val Ser Thr Ile Asn Ser Asn Leu Asp Val Phe Phe
                405                 410                 415

Lys Asp Gly Gln Lys Ile Thr Arg Asp Arg Leu Ala Ala Met Ser Gln
            420                 425                 430

Asp Glu Ser Leu Ser Pro Ala Val Arg Asn Ala Ala Lys Gln Leu Leu
        435                 440                 445

Gln Asp Pro Leu Leu Tyr Gly Leu Ile Asn Asn Ala Asn Ser Gly Tyr
    450                 455                 460

Lys Thr Lys Asn Gly Phe Phe Ser Phe Gly Gly Pro Thr Val Asp Ser
465                 470                 475                 480

Gly Val Ile Gly Lys Lys Asp Phe Glu Lys Phe Met Ser Ser Met Thr
                485                 490                 495

Asp Ala Asn Lys Thr Val Gln Ala Arg Lys Thr His Pro Ala Asn Ser
            500                 505                 510

Glu Ala Ser Lys Ser Ala Val Ala Asp Met Gly Met Gly Met Glu Asp
```

```
        515                 520                 525

Gln Pro Asp Ile Lys Ala Val Lys Lys Ser Gly Gly Ala Leu Lys Lys
    530                 535                 540

Ala Met Asp Lys Ile Leu Thr Ile Tyr Ser Lys Val Met Asp Ile Ala
545                 550                 555                 560

Ser Gln Val Val Gly Ala Leu Gly Val Ile Pro Gly Leu Gly Glu Ile
                565                 570                 575

Ala Asp Ala Leu Ser Met Gly Met Ala Ala Gly Ala Ser Ala Ala Lys
            580                 585                 590

Val Leu Ser Thr Leu Leu Asn Gly Gly Ser Leu Lys Lys Ala Leu Ala
        595                 600                 605

Glu Ala Gly Ile Asn Leu Ala Ser Ala Ala Leu Gly Ala Val Ala Gly
    610                 615                 620

Pro Glu Ala Arg Val Ala Leu Lys Asn Gly Leu Thr Lys Met Leu Val
625                 630                 635                 640

Glu Lys Val Ala Asn Thr Gly Ile Asp Leu Ala Val Asp Lys Ala Lys
                645                 650                 655

Ser Phe Val Asp Gly Tyr Leu Gln Asp Leu Lys Gly Arg Leu Gln Ala
            660                 665                 670

Thr Ala Ala Asn Ala Ala Asn Thr Val Asn Thr Ser Val Asn Trp Val
        675                 680                 685

Ser Asp Lys Thr Lys Asp Phe Leu Glu Asn Pro Val Gln Asn Leu Thr
    690                 695                 700

Pro Arg Val Asn Ile Pro Gly Ile Thr Pro Tyr Gln Pro Gly Tyr Pro
705                 710                 715                 720

Met Val Ala Ala Ala Ala
                725
```

<210> SEQ ID NO 68
<211> LENGTH: 2214
<212> TYPE: DNA
<213> ORGANISM: Ralstonia solanacearum

<400> SEQUENCE: 68

```
atgagtacca acatttccag tgcggcaaga ccgactgtgc cagcgggcgg gtcggacgcc      60

agcggggctg ccacgaacaa ccccgacctt ccgtcctccc tgttcttcca gtacgaccat     120

tccacggggc cgagccggcc tgacctgccg cccgagctgt tcttcaagtt cgacgaatcc     180

gtttcgcgcg cggtgcagga cgcggcccag cagtcgcccg atccgtcggc gaatccggct     240

gccccgggag gccaaggctg ccagtgccag ccggcccccg ccgataacgc gccgccgcag     300

cagtgccagc ccagcgcccc gccggtcggc agcgatgtga cctggaacgg tggcacgctc     360

aatgacacgc agttgcaggt gctcggcatc ctgaacctgt acctgagcat tggcggcctg     420

ccgttcggtg agcgagcgat gacccgggat acgctcgaga aggcggccaa cagtgccgat     480

gcgccggccg acctgcgctg ggcggcgcag gcgatgctga acgatcccgc cctgtaccag     540

gccatcggcg gcgacgacgg aaagttcgcg cggaaagaca tcgcgaagtt tgccgggtac     600

cacccgcagg tcctgacctg gaacggcggc acgctcaacg acagccaact ggaaatcacc     660

tccatcctgg cccggcacaa ggacaagctg ccgctggact ggcagtcgat ccaggacaag     720

gccaacgatc ccagcacacc gcccgacctg aaggccgcgc tgcaggcgct ggccaacgat     780

cccgccctgt tcctcgccat cggctcgcag ggcgacggca agtgcggggg caagatcaag     840

gccggcgatg tgggcagctt catcgacaac cacccgcagg cggtcgagta caaccggaag     900
```

```
aaggccgaag gctatgtgaa ggactacatc ccgtccgacg cgaagccggg cgacaagccc    960

tccgccatga cgcagaacga cgcgctgcgc gagctgtacc gctactcgga ctatctgccg   1020

aagaagctgg acatggacgc actccagcac atcgtcgacg gcgactcgaa cgccaagaag   1080

acgccgccgc aggtcatcgc cgcggcccag tatttcctgc agaaccgcaa cgagtgggcc   1140

agcctgaaca agctggggga caacccccgac aagaaggtgg gcaaggcgga cttcctgcag   1200

cgcgccgcgt cgtccgtcca cctgaccaag gaagacctga agaccgtgtc gacgatcaat   1260

gacaatctcg acgtgttttt caaggacggc cagaagatca cgcgcgaccg gctggcggcc   1320

atgtcggagg acgagagcct gtcttccggt gtccgcgatg cggccaagca gttgctgcag   1380

gacccgctgc tgtacggcct gatcaacaac gcgaactcgg gctacaagac gaagaacggc   1440

ttcttcagct tcggcggccc gacggtggac tccggcgtga tcggcaagaa ggacttcgag   1500

aagttcatgt ccagcatgac ggacgccaac aagacggtcc aggagcgcaa gacgcatgcc   1560

gcgcactcgg aggccagcaa gagcgccgtg tcggacatgg gcatggggat ggaagaccag   1620

cccgacatca aggccgtgaa gaagagcggc ggcgccctga agaaggtcat ggacaaggtc   1680

ctcaccatct acgcgaaggt gatggacatt gcgtcgcagg tcgtcggtgc gctgggcgtg   1740

attccggggc tgggcgaaat cgcggacgca ctgtcgatcg ggatggccgc cggggcatcg   1800

gccgccaagg tcctgtcgac cctgctggac ggcggcaacc tcaagaaggc actggcggag   1860

gccggcatca acctggcatc cgctgcgctg ggggccatcg ccgggccgga ggcgcgggtg   1920

gcgctcaaga acggcctgac caagatgctc gtggagaagg tggccaacac cggcatcgat   1980

ctggcggtcg acaaggcgaa gtcgttcgtg gacggctacc tgcaggacct gaagggccgc   2040

ctgtacgcca acacggccaa cgccgtccac gcggtcaaca ccggcgtcaa ctgggtgtcc   2100

gacaagacgc aggacttgct gcagaacccc atgcagaacc tgacgacccg tttgaacatc   2160

cccggcgtga ctccgtatca accgggctat ccgatggtgg cgccggccgc ctga         2214
```

<210> SEQ ID NO 69
<211> LENGTH: 737
<212> TYPE: PRT
<213> ORGANISM: Ralstonia solanacearum

<400> SEQUENCE: 69

```
Met Ser Thr Asn Ile Ser Ser Ala Ala Arg Pro Thr Val Pro Ala Gly
1               5                   10                  15

Gly Ser Asp Ala Ser Gly Ala Ala Thr Asn Asn Pro Asp Leu Pro Ser
            20                  25                  30

Ser Leu Phe Phe Gln Tyr Asp His Ser Thr Gly Pro Ser Arg Pro Asp
        35                  40                  45

Leu Pro Pro Glu Leu Phe Phe Lys Phe Asp Glu Ser Val Ser Arg Ala
    50                  55                  60

Val Gln Asp Ala Ala Gln Gln Ser Pro Asp Pro Ser Ala Asn Pro Ala
65                  70                  75                  80

Ala Pro Gly Gly Gln Gly Cys Gln Cys Gln Pro Ala Pro Ala Asp Asn
                85                  90                  95

Ala Pro Pro Gln Gln Cys Gln Pro Ser Ala Pro Pro Val Gly Ser Asp
            100                 105                 110

Val Thr Trp Asn Gly Gly Thr Leu Asn Asp Thr Gln Leu Gln Val Leu
        115                 120                 125

Gly Ile Leu Asn Leu Tyr Leu Ser Ile Gly Gly Leu Pro Phe Gly Glu
    130                 135                 140
```

```
Arg Ala Met Thr Arg Asp Thr Leu Glu Lys Ala Ala Asn Ser Ala Asp
145                 150                 155                 160

Ala Pro Ala Asp Leu Arg Trp Ala Ala Gln Ala Met Leu Asn Asp Pro
                165                 170                 175

Ala Leu Tyr Gln Ala Ile Gly Gly Asp Asp Gly Lys Phe Ala Arg Lys
            180                 185                 190

Asp Ile Ala Lys Phe Ala Gly Tyr His Pro Gln Val Leu Thr Trp Asn
        195                 200                 205

Gly Gly Thr Leu Asn Asp Ser Gln Leu Glu Ile Thr Ser Ile Leu Ala
    210                 215                 220

Arg His Lys Asp Lys Leu Pro Leu Asp Trp Gln Ser Ile Gln Asp Lys
225                 230                 235                 240

Ala Asn Asp Pro Ser Thr Pro Pro Asp Leu Lys Ala Ala Leu Gln Ala
                245                 250                 255

Leu Ala Asn Asp Pro Ala Leu Phe Leu Ala Ile Gly Ser Gln Gly Asp
            260                 265                 270

Gly Lys Cys Gly Gly Lys Ile Lys Ala Gly Asp Val Gly Ser Phe Ile
        275                 280                 285

Asp Asn His Pro Gln Ala Val Glu Tyr Asn Arg Lys Lys Ala Glu Gly
    290                 295                 300

Tyr Val Lys Asp Tyr Ile Pro Ser Asp Ala Lys Pro Gly Asp Lys Pro
305                 310                 315                 320

Ser Ala Met Thr Gln Asn Asp Ala Leu Arg Glu Leu Tyr Arg Tyr Ser
                325                 330                 335

Asp Tyr Leu Pro Lys Lys Leu Asp Met Asp Ala Leu Gln His Ile Val
            340                 345                 350

Asp Gly Asp Ser Asn Ala Lys Lys Thr Pro Pro Gln Val Ile Ala Ala
        355                 360                 365

Ala Gln Tyr Phe Leu Gln Asn Arg Asn Glu Trp Ala Ser Leu Asn Lys
    370                 375                 380

Leu Gly Asp Asn Pro Asp Lys Lys Val Gly Lys Ala Asp Phe Leu Gln
385                 390                 395                 400

Arg Ala Ala Ser Ser Val His Leu Thr Lys Glu Asp Leu Lys Thr Val
                405                 410                 415

Ser Thr Ile Asn Asp Asn Leu Asp Val Phe Phe Lys Asp Gly Gln Lys
            420                 425                 430

Ile Thr Arg Asp Arg Leu Ala Ala Met Ser Glu Asp Glu Ser Leu Ser
        435                 440                 445

Ser Gly Val Arg Asp Ala Ala Lys Gln Leu Leu Gln Asp Pro Leu Leu
    450                 455                 460

Tyr Gly Leu Ile Asn Asn Ala Asn Ser Gly Tyr Lys Thr Lys Asn Gly
465                 470                 475                 480

Phe Phe Ser Phe Gly Gly Pro Thr Val Asp Ser Gly Val Ile Gly Lys
                485                 490                 495

Lys Asp Phe Glu Lys Phe Met Ser Ser Met Thr Asp Ala Asn Lys Thr
            500                 505                 510

Val Gln Glu Arg Lys Thr His Ala Ala His Ser Glu Ala Ser Lys Ser
        515                 520                 525

Ala Val Ser Asp Met Gly Met Gly Met Glu Asp Gln Pro Asp Ile Lys
    530                 535                 540

Ala Val Lys Lys Ser Gly Gly Ala Leu Lys Lys Val Met Asp Lys Val
545                 550                 555                 560

Leu Thr Ile Tyr Ala Lys Val Met Asp Ile Ala Ser Gln Val Val Gly
```

```
                565                 570                 575

Ala Leu Gly Val Ile Pro Gly Leu Gly Glu Ile Ala Asp Ala Leu Ser
            580                 585                 590

Ile Gly Met Ala Ala Gly Ala Ser Ala Ala Lys Val Leu Ser Thr Leu
        595                 600                 605

Leu Asp Gly Gly Asn Leu Lys Lys Ala Leu Ala Glu Ala Gly Ile Asn
    610                 615                 620

Leu Ala Ser Ala Ala Leu Gly Ala Ile Ala Gly Pro Glu Ala Arg Val
625                 630                 635                 640

Ala Leu Lys Asn Gly Leu Thr Lys Met Leu Val Glu Lys Val Ala Asn
                645                 650                 655

Thr Gly Ile Asp Leu Ala Val Asp Lys Ala Lys Ser Phe Val Asp Gly
            660                 665                 670

Tyr Leu Gln Asp Leu Lys Gly Arg Leu Tyr Ala Asn Thr Ala Asn Ala
        675                 680                 685

Val His Ala Val Asn Thr Gly Val Asn Trp Val Ser Asp Lys Thr Gln
    690                 695                 700

Asp Leu Leu Gln Asn Pro Met Gln Asn Leu Thr Thr Arg Leu Asn Ile
705                 710                 715                 720

Pro Gly Val Thr Pro Tyr Gln Pro Gly Tyr Pro Met Val Ala Pro Ala
                725                 730                 735

Ala


<210> SEQ ID NO 70
<211> LENGTH: 82
<212> TYPE: PRT
<213> ORGANISM: Ralstonia solanacearum

<400> SEQUENCE: 70

Met Ala Gly Val Pro Lys Pro Asn Thr Thr Asn Thr Thr Ser Thr Thr
1               5                   10                  15

Ser Thr Phe Gln Ser Phe Ala Asn Gly Val Asp Asp Ala Ala Ser Arg
            20                  25                  30

Thr Gly Phe Gln Ala Gln Tyr Gln Ala Ile Thr Ala Gln Gly Gln Gln
        35                  40                  45

Asp Met Leu Asp Ala Ala Lys Met Gln Asn Ala Leu Asn Arg Thr Gln
    50                  55                  60

Met Leu Ala Lys Leu Met Glu Ala Gly Pro Lys Ala Ala Lys Asp Leu
65                  70                  75                  80

Ile Ser


<210> SEQ ID NO 71
<211> LENGTH: 82
<212> TYPE: PRT
<213> ORGANISM: Ralstonia solanacearum GMI1000

<400> SEQUENCE: 71

Met Ala Gly Val Pro Lys Pro Asn Thr Thr Asn Thr Thr Ser Thr Thr
1               5                   10                  15

Ser Thr Phe Gln Ser Phe Ala Asn Gly Val Asp Asp Ala Ala Ser Arg
            20                  25                  30

Thr Gly Phe Gln Ala Gln Tyr Gln Ala Ile Thr Ala Gln Gly Gln Gln
        35                  40                  45

Asp Met Leu Asp Ala Ala Lys Met Gln Asn Ala Leu Asn Arg Thr Gln
    50                  55                  60
```

```
Met Leu Ala Lys Leu Met Glu Ala Gly Pro Lys Ala Ala Lys Asp Leu
65                  70                  75                  80

Ile Ser


<210> SEQ ID NO 72
<211> LENGTH: 82
<212> TYPE: PRT
<213> ORGANISM: Ralstonia solanacearum GMI1000

<400> SEQUENCE: 72

Met Ala Gly Val Pro Lys Pro Asn Thr Thr Asn Thr Thr Ser Thr Thr
1               5                   10                  15

Ser Thr Phe Gln Ser Phe Ala Asn Gly Val Asp Asp Ala Ala Ser Arg
            20                  25                  30

Thr Gly Phe Gln Ala Gln Tyr Gln Ala Ile Thr Ala Gln Gly Gln Gln
        35                  40                  45

Asp Met Leu Asp Ala Ala Lys Met Gln Asn Ala Leu Asn Arg Thr Gln
    50                  55                  60

Met Leu Ala Lys Leu Met Glu Ala Gly Pro Lys Ala Ala Lys Asp Leu
65                  70                  75                  80

Ile Ser


<210> SEQ ID NO 73
<211> LENGTH: 82
<212> TYPE: PRT
<213> ORGANISM: Ralstonia solanacearum UW551

<400> SEQUENCE: 73

Met Ala Gly Val Pro Lys Pro Asn Thr Thr Asn Thr Thr Ser Thr Thr
1               5                   10                  15

Ser Thr Phe Gln Ser Phe Ala Asn Gly Val Asp Asp Ala Ala Ser Arg
            20                  25                  30

Thr Gly Phe Gln Ala Gln Tyr Gln Ala Ile Thr Ala Glu Gly Gln Gln
        35                  40                  45

Asp Met Leu Asp Ala Ala Lys Met Gln Asn Ala Leu Asn Arg Thr Gln
    50                  55                  60

Met Leu Ala Lys Leu Met Glu Ala Gly Pro Lys Ala Ala Lys Asp Leu
65                  70                  75                  80

Ile Ser


<210> SEQ ID NO 74
<211> LENGTH: 82
<212> TYPE: PRT
<213> ORGANISM: Ralstonia solanacearum UW551

<400> SEQUENCE: 74

Met Ala Gly Val Pro Lys Pro Asn Thr Thr Asn Thr Thr Ser Thr Thr
1               5                   10                  15

Ser Thr Phe Gln Ser Phe Ala Asn Gly Val Asp Asp Ala Ala Ser Arg
            20                  25                  30

Thr Gly Phe Gln Ala Gln Tyr Gln Ala Ile Thr Ala Glu Gly Gln Gln
        35                  40                  45

Asp Met Leu Asp Ala Ala Lys Met Gln Asn Ala Leu Asn Arg Thr Gln
    50                  55                  60

Met Leu Ala Lys Leu Met Glu Ala Gly Pro Lys Ala Ala Lys Asp Leu
65                  70                  75                  80

Ile Ser
```

<210> SEQ ID NO 75
<211> LENGTH: 82
<212> TYPE: PRT
<213> ORGANISM: Ralstonia solanacearum IPO1609

<400> SEQUENCE: 75

```
Met Ala Gly Val Pro Lys Pro Asn Thr Thr Asn Thr Thr Ser Thr Thr
1               5                   10                  15

Ser Thr Phe Gln Ser Phe Ala Asn Gly Val Asp Asp Ala Ala Ser Arg
            20                  25                  30

Thr Gly Phe Gln Ala Gln Tyr Gln Ala Ile Thr Ala Glu Gly Gln Gln
        35                  40                  45

Asp Met Leu Asp Ala Ala Lys Met Gln Asn Ala Leu Asn Arg Thr Gln
    50                  55                  60

Met Leu Ala Lys Leu Met Glu Ala Gly Pro Lys Ala Ala Lys Asp Leu
65                  70                  75                  80

Ile Ser
```

<210> SEQ ID NO 76
<211> LENGTH: 82
<212> TYPE: PRT
<213> ORGANISM: Ralstonia solanacearum MolK2

<400> SEQUENCE: 76

```
Met Ala Gly Val Pro Lys Pro Asn Thr Thr Asn Thr Thr Ser Thr Thr
1               5                   10                  15

Ser Thr Phe Gln Ser Phe Ala Asn Gly Val Asp Asp Ala Ala Ser Arg
            20                  25                  30

Thr Gly Phe Gln Ala Gln Tyr Gln Ala Ile Thr Ala Glu Gly Gln Gln
        35                  40                  45

Asp Met Leu Asp Ala Ala Lys Met Gln Asn Ala Leu Asn Arg Thr Gln
    50                  55                  60

Met Leu Ala Lys Leu Met Glu Ala Gly Pro Lys Ala Ala Lys Asp Leu
65                  70                  75                  80

Ile Ser
```

<210> SEQ ID NO 77
<211> LENGTH: 82
<212> TYPE: PRT
<213> ORGANISM: Ralstonia solanacearum IPO1609

<400> SEQUENCE: 77

```
Met Ala Gly Val Pro Lys Pro Asn Thr Thr Asn Thr Thr Ser Thr Thr
1               5                   10                  15

Ser Thr Phe Gln Ser Phe Ala Asn Gly Val Asp Asp Ala Ala Ser Arg
            20                  25                  30

Thr Gly Phe Gln Ala Gln Tyr Gln Ala Ile Thr Ala Glu Gly Gln Gln
        35                  40                  45

Asp Met Leu Asp Ala Ala Lys Met Gln Asn Ala Leu Asn Arg Thr Gln
    50                  55                  60

Met Leu Ala Lys Leu Met Glu Ala Gly Pro Lys Ala Ala Lys Asp Leu
65                  70                  75                  80

Ile Ser
```

<210> SEQ ID NO 78
<211> LENGTH: 82

-continued

```
<212> TYPE: PRT
<213> ORGANISM: Ralstonia solanacearum MolK2

<400> SEQUENCE: 78

Met Ala Gly Val Pro Lys Pro Asn Thr Thr Asn Thr Thr Ser Thr Thr
1               5                   10                  15

Ser Thr Phe Gln Ser Phe Ala Asn Gly Val Asp Asp Ala Ala Ser Arg
            20                  25                  30

Thr Gly Phe Gln Ala Gln Tyr Gln Ala Ile Thr Ala Glu Gly Gln Gln
        35                  40                  45

Asp Met Leu Asp Ala Ala Lys Met Gln Asn Ala Leu Asn Arg Thr Gln
    50                  55                  60

Met Leu Ala Lys Leu Met Glu Ala Gly Pro Lys Ala Ala Lys Asp Leu
65                  70                  75                  80

Ile Ser


<210> SEQ ID NO 79
<211> LENGTH: 82
<212> TYPE: PRT
<213> ORGANISM: Ralstonia solanacearum CFBP2957

<400> SEQUENCE: 79

Met Ala Gly Val Pro Lys Pro Thr Thr Thr Asn Thr Thr Ser Thr Thr
1               5                   10                  15

Ser Thr Phe Gln Ser Phe Ala Asn Gly Val Asp Asp Ala Ala Ser Arg
            20                  25                  30

Thr Gly Phe Gln Ala Gln Tyr Gln Ala Ile Thr Ala Glu Gly Gln Gln
        35                  40                  45

Asp Met Leu Asp Ala Ala Lys Met Gln Asn Ala Leu Asn Arg Thr Gln
    50                  55                  60

Met Leu Ala Lys Leu Met Glu Ala Gly Pro Lys Ala Ala Lys Asp Leu
65                  70                  75                  80

Ile Ser


<210> SEQ ID NO 80
<211> LENGTH: 82
<212> TYPE: PRT
<213> ORGANISM: Ralstonia solanacearum PSI07

<400> SEQUENCE: 80

Met Ala Gly Val Pro Lys Pro Thr Thr Thr Asn Thr Thr Ser Thr Thr
1               5                   10                  15

Ser Thr Phe Gln Ser Phe Ala Asn Gly Val Asp Asp Ala Ala Ser Arg
            20                  25                  30

Thr Gly Phe Gln Ala Gln Tyr Gln Ala Ile Thr Ala Glu Gly Gln Gln
        35                  40                  45

Asp Met Leu Asp Ala Ala Lys Met Gln Asn Ala Leu Asn Arg Thr Gln
    50                  55                  60

Met Leu Ala Lys Leu Met Glu Ala Gly Pro Lys Ala Ala Lys Asp Leu
65                  70                  75                  80

Ile Ser


<210> SEQ ID NO 81
<211> LENGTH: 82
<212> TYPE: PRT
<213> ORGANISM: Ralstonia solanacearum PSI07

<400> SEQUENCE: 81
```

```
Met Ala Gly Val Pro Lys Pro Thr Thr Thr Asn Thr Thr Ser Thr Thr
1               5                   10                  15

Ser Thr Phe Gln Ser Phe Ala Asn Gly Val Asp Asp Ala Ala Ser Arg
            20                  25                  30

Thr Gly Phe Gln Ala Gln Tyr Gln Ala Ile Thr Ala Glu Gly Gln Gln
        35                  40                  45

Asp Met Leu Asp Ala Ala Lys Met Gln Asn Ala Leu Asn Arg Thr Gln
    50                  55                  60

Met Leu Ala Lys Leu Met Glu Ala Gly Pro Lys Ala Ala Lys Asp Leu
65                  70                  75                  80

Ile Ser


<210> SEQ ID NO 82
<211> LENGTH: 82
<212> TYPE: PRT
<213> ORGANISM: Ralstonia solanacearum CFBP2957

<400> SEQUENCE: 82

Met Ala Gly Val Pro Lys Pro Thr Thr Thr Asn Thr Thr Ser Thr Thr
1               5                   10                  15

Ser Thr Phe Gln Ser Phe Ala Asn Gly Val Asp Asp Ala Ala Ser Arg
            20                  25                  30

Thr Gly Phe Gln Ala Gln Tyr Gln Ala Ile Thr Ala Glu Gly Gln Gln
        35                  40                  45

Asp Met Leu Asp Ala Ala Lys Met Gln Asn Ala Leu Asn Arg Thr Gln
    50                  55                  60

Met Leu Ala Lys Leu Met Glu Ala Gly Pro Lys Ala Ala Lys Asp Leu
65                  70                  75                  80

Ile Ser


<210> SEQ ID NO 83
<211> LENGTH: 82
<212> TYPE: PRT
<213> ORGANISM: Ralstonia solanacearum CMR15

<400> SEQUENCE: 83

Met Ala Gly Val Pro Lys Pro Thr Thr Thr Asn Thr Thr Ser Thr Thr
1               5                   10                  15

Ser Thr Phe Gln Ser Phe Ala Asn Gly Val Asp Asp Ala Ala Ser Arg
            20                  25                  30

Thr Gly Phe Gln Ala Gln Tyr Gln Ala Ile Thr Ala Glu Gly Gln Gln
        35                  40                  45

Asp Met Leu Asp Ala Ala Lys Met Gln Asn Ala Leu Asn Arg Thr Gln
    50                  55                  60

Met Leu Ala Lys Leu Met Glu Ala Gly Pro Lys Ala Ala Lys Asp Leu
65                  70                  75                  80

Ile Ser


<210> SEQ ID NO 84
<211> LENGTH: 82
<212> TYPE: PRT
<213> ORGANISM: Ralstonia solanacearum

<400> SEQUENCE: 84

Met Ala Gly Val Pro Lys Pro Thr Thr Thr Asn Thr Thr Ser Thr Thr
1               5                   10                  15
```

```
Ser Thr Phe Gln Ser Phe Ala Asn Gly Val Asp Asp Ala Ala Ser Arg
            20                  25                  30

Thr Gly Phe Gln Ala Gln Tyr Gln Ala Ile Thr Ala Gln Gly Gln Gln
        35                  40                  45

Asp Met Leu Asp Ala Ala Lys Met Gln Asn Ala Leu Asn Arg Thr Gln
    50                  55                  60

Met Leu Ala Lys Leu Met Glu Ala Gly Pro Lys Ala Ala Lys Asp Leu
65                  70                  75                  80

Ile Ser


<210> SEQ ID NO 85
<211> LENGTH: 82
<212> TYPE: PRT
<213> ORGANISM: Ralstonia solanacearum

<400> SEQUENCE: 85

Met Ala Gly Val Pro Lys Pro Thr Thr Thr Asn Thr Thr Ser Thr Thr
1               5                   10                  15

Ser Thr Phe Gln Ser Phe Ala Asn Gly Val Asp Asp Ala Ala Ser Arg
            20                  25                  30

Thr Gly Phe Gln Ala Gln Tyr Gln Ala Ile Thr Ala Gln Gly Gln Gln
        35                  40                  45

Asp Met Leu Asp Ala Ala Lys Met Gln Asn Ala Leu Asn Arg Thr Gln
    50                  55                  60

Met Leu Ala Lys Leu Met Glu Ala Gly Pro Lys Ala Ala Lys Asp Leu
65                  70                  75                  80

Ile Ser


<210> SEQ ID NO 86
<211> LENGTH: 82
<212> TYPE: PRT
<213> ORGANISM: Ralstonia solanacearum

<400> SEQUENCE: 86

Met Ala Gly Val Pro Lys Pro Thr Thr Thr Asn Thr Thr Ser Thr Thr
1               5                   10                  15

Ser Thr Phe Gln Ser Phe Ala Asn Gly Val Asp Asp Ala Ala Ser Arg
            20                  25                  30

Thr Gly Phe Gln Ala Gln Tyr Gln Ala Ile Thr Ala Gln Gly Gln Gln
        35                  40                  45

Asp Met Leu Asp Ala Ala Lys Met Gln Asn Ala Leu Asn Arg Thr Gln
    50                  55                  60

Met Leu Ala Lys Leu Met Glu Ala Gly Pro Lys Ala Ala Lys Asp Leu
65                  70                  75                  80

Ile Ser


<210> SEQ ID NO 87
<211> LENGTH: 228
<212> TYPE: DNA
<213> ORGANISM: Erwinia amylovora

<400> SEQUENCE: 87

atgagcggca ttattacagg tatggcaggc agttcactta caagcgcaag cacttcagca      60

tccaagacgc tggaatcagc aatgggtcag tcactgaccg agtctgccaa tgctcaggcg     120

tctaaaatga agatggatac gcagaactcg atcctggatg gcaaaatgga ctccgcttct     180

aagtccataa actctggcca caacgcggct aaagctattc agttctga                 228
```

<210> SEQ ID NO 88
<211> LENGTH: 75
<212> TYPE: PRT
<213> ORGANISM: Erwinia amylovora

<400> SEQUENCE: 88

Met Ser Gly Ile Ile Thr Gly Met Ala Gly Ser Ser Leu Thr Ser Ala
1 5 10 15

Ser Thr Ser Ala Ser Lys Thr Leu Glu Ser Ala Met Gly Gln Ser Leu
20 25 30

Thr Glu Ser Ala Asn Ala Gln Ala Ser Lys Met Lys Met Asp Thr Gln
35 40 45

Asn Ser Ile Leu Asp Gly Lys Met Asp Ser Ala Ser Lys Ser Ile Asn
50 55 60

Ser Gly His Asn Ala Ala Lys Ala Ile Gln Phe
65 70 75

<210> SEQ ID NO 89
<211> LENGTH: 273
<212> TYPE: DNA
<213> ORGANISM: Xanthomonas campestris

<400> SEQUENCE: 89
atgctaaatt tacaatcgat agtgccgcga ttgggccagg ccagggatct gcttggatct 60
gacctttcaa gcagatttga caatcacact gccactcaga cctcggacaa tcagatggat 120
agtctgatgg gtggcattgg taaatcagcc gcagcacagg agcgcatgaa caactacctg 180
accgcgaaga agaacgaact tgacttcaac gtggcgctca acaaattcat cggcaaggca 240
ggcgacaacg cgaagcagct ggttggccag taa 273

<210> SEQ ID NO 90
<211> LENGTH: 90
<212> TYPE: PRT
<213> ORGANISM: Xanthomonas campestris

<400> SEQUENCE: 90

Met Leu Asn Leu Gln Ser Ile Val Pro Arg Leu Gly Gln Ala Arg Asp
1 5 10 15

Leu Leu Gly Ser Asp Leu Ser Ser Arg Phe Asp Asn His Thr Ala Thr
20 25 30

Gln Thr Ser Asp Asn Gln Met Asp Ser Leu Met Gly Gly Ile Gly Lys
35 40 45

Ser Ala Ala Ala Gln Glu Arg Met Asn Asn Tyr Leu Thr Ala Lys Lys
50 55 60

Asn Glu Leu Asp Phe Asn Val Ala Leu Asn Lys Phe Ile Gly Lys Ala
65 70 75 80

Gly Asp Asn Ala Lys Gln Leu Val Gly Gln
85 90

<210> SEQ ID NO 91
<211> LENGTH: 282
<212> TYPE: DNA
<213> ORGANISM: Xanthomonas oryzae

<400> SEQUENCE: 91
atggaaatac ttccgcaaat cagctcactt aattcgcgct tccaacaggg tatggatggc 60
tataccggag gtgtggccaa tggaatctcc ggtgcttctg cactctctgg ctcgaacggg 120
cagatgggtt cgttgctcgg cgacatgagt gcctcggacg aggctcagaa gtccatgaac 180
aacaagatca cgcagctcaa aaacgatctt gacttcaacg tggcactcaa caagttcatc 240
ggcaaggcgg gcgacaacgc taagcagctc gttggccagt aa 282

<210> SEQ ID NO 92
<211> LENGTH: 93
<212> TYPE: PRT
<213> ORGANISM: Xanthomonas oryzae

<400> SEQUENCE: 92

Met Glu Ile Leu Pro Gln Ile Ser Ser Leu Asn Ser Arg Phe Gln Gln
1 5 10 15

Gly Met Asp Gly Tyr Thr Gly Gly Val Ala Asn Gly Ile Ser Gly Ala
20 25 30

Ser Ala Leu Ser Gly Ser Asn Gly Gln Met Gly Ser Leu Leu Gly Asp
35 40 45

Met Ser Ala Ser Asp Glu Ala Gln Lys Ser Met Asn Asn Lys Ile Thr
50 55 60

Gln Leu Lys Asn Asp Leu Asp Phe Asn Val Ala Leu Asn Lys Phe Ile
65 70 75 80

Gly Lys Ala Gly Asp Asn Ala Lys Gln Leu Val Gly Gln
85 90

<210> SEQ ID NO 93
<211> LENGTH: 25
<212> TYPE: DNA
<213> ORGANISM: Artificial sequence
<220> FEATURE:
<223> OTHER INFORMATION: Forward PCR primer for WiltR_HrpY mutant 6

<400> SEQUENCE: 93
gtcttgttcc tgtctacctt gctcc 25

<210> SEQ ID NO 94
<211> LENGTH: 25
<212> TYPE: DNA
<213> ORGANISM: Artificial sequence
<220> FEATURE:
<223> OTHER INFORMATION: Reverse PCR primer for WiltR_HrpY mutant 6

<400> SEQUENCE: 94
gagattaggt ctttcgcagc tttgg 25

<210> SEQ ID NO 95
<211> LENGTH: 27
<212> TYPE: DNA
<213> ORGANISM: Artificial sequence
<220> FEATURE:
<223> OTHER INFORMATION: Forward PCR primer for WiltR_HrpY mutant 1

<400> SEQUENCE: 95
tctctttgct ctcctttata gccctac 27

<210> SEQ ID NO 96
<211> LENGTH: 27
<212> TYPE: DNA
<213> ORGANISM: Artificial sequence
<220> FEATURE:
<223> OTHER INFORMATION: Reverse PCR primer for WiltR_HrpY mutant 1

<400> SEQUENCE: 96
tcgcagcgtc taacatatct tgttgtc 27

<210> SEQ ID NO 97
<211> LENGTH: 27
<212> TYPE: DNA
<213> ORGANISM: Artificial sequence
<220> FEATURE:
<223> OTHER INFORMATION: Forward PCR primer for WiltR_HrpY mutant 2

<400> SEQUENCE: 97
gtcacatggt tcgttggtgt actcttc 27

<210> SEQ ID NO 98
<211> LENGTH: 27
<212> TYPE: DNA
<213> ORGANISM: Artificial sequence
<220> FEATURE:
<223> OTHER INFORMATION: Reverse PCR primer for WiltR_HrpY mutant 2

<400> SEQUENCE: 98
catctgggtt ctattcagcg cattttg 27

<210> SEQ ID NO 99
<211> LENGTH: 204
<212> TYPE: DNA
<213> ORGANISM: Erwinia pyrifoliae

<400> SEQUENCE: 99
atgagcggtc ttcttacaag cgcaagcagt tcagcatcta aaactcttga atcagcaatg 60
ggtcagtcac tgaccgagtc tgccaatgcg caggcgtcta aaatgaagat ggatacccag 120
aactccatcc ttgatggcaa aatggactct gcttctaagt ccttgaactc tggccacaac 180
gcggctaaag ctattcagtt ctga 204

<210> SEQ ID NO 100
<211> LENGTH: 67
<212> TYPE: PRT
<213> ORGANISM: Erwinia pyrifoliae

<400> SEQUENCE: 100

Met Ser Gly Leu Leu Thr Ser Ala Ser Ser Ser Ala Ser Lys Thr Leu
1 5 10 15

Glu Ser Ala Met Gly Gln Ser Leu Thr Glu Ser Ala Asn Ala Gln Ala
20 25 30

Ser Lys Met Lys Met Asp Thr Gln Asn Ser Ile Leu Asp Gly Lys Met
35 40 45

Asp Ser Ala Ser Lys Ser Leu Asn Ser Gly His Asn Ala Ala Lys Ala
50 55 60

Ile Gln Phe
65